US008889840B2

(12) United States Patent
Kwon et al.

(10) Patent No.: US 8,889,840 B2
(45) Date of Patent: Nov. 18, 2014

(54) VASCULAR LEAKAGE INHIBITOR

(75) Inventors: Young-Guen Kwon, Seoul (KR); Young-Ger Suh, Seoul (KR)

(73) Assignee: Industry-Academic Cooperation Foundation, Yonsei University, Seoul (KR)

( * ) Notice: Subject to any disclaimer, the term of this patent is extended or adjusted under 35 U.S.C. 154(b) by 0 days.

(21) Appl. No.: 13/504,368

(22) PCT Filed: Oct. 29, 2010

(86) PCT No.: PCT/KR2010/007533
§ 371 (c)(1),
(2), (4) Date: Apr. 26, 2012

(87) PCT Pub. No.: WO2011/053048
PCT Pub. Date: May 5, 2011

(65) Prior Publication Data
US 2012/0245110 A1    Sep. 27, 2012

(30) Foreign Application Priority Data
Oct. 29, 2009  (KR) .................. 10-2009-0103450

(51) Int. Cl.
| | | |
|---|---|---|
| *C07J 41/00* | (2006.01) | |
| *C07J 17/00* | (2006.01) | |
| *A01N 45/00* | (2006.01) | |
| *A61K 31/59* | (2006.01) | |
| *A61K 31/58* | (2006.01) | |
| *A61K 31/56* | (2006.01) | |
| *C07D 309/12* | (2006.01) | |
| *C07D 239/34* | (2006.01) | |
| *C07D 309/30* | (2006.01) | |
| *C07D 309/10* | (2006.01) | |
| *C07D 303/22* | (2006.01) | |

(52) U.S. Cl.
CPC ............ *C07D 309/12* (2013.01); *C07D 239/34* (2013.01); *C07D 309/30* (2013.01); *C07D 309/10* (2013.01); *C07D 303/22* (2013.01); *C07J 17/00* (2013.01)
USPC ................. 536/5; 540/118; 514/26; 514/167; 514/172; 514/182

(58) Field of Classification Search
None
See application file for complete search history.

(56) References Cited

U.S. PATENT DOCUMENTS 7,985,848 B2   7/2011   Woo et al.

FOREIGN PATENT DOCUMENTS

| EP | 0664129 A2 * | 7/1995 |
| WO | WO-97/18816 A2 | 5/1997 |

OTHER PUBLICATIONS

Merten et al. Circulation, 2001; 103:2032-2034.*
Kunimoto et al. Cell Stress & Chaperones (2000) 5 (1), 3-7.*
PubChem record for cholesteryl glucoside, downloaded from the internet Oct. 8, 2013.*
PubChem record for cholesteryl sulfate, downloaded from the internet Oct. 8, 2013.*
Kurokawa et al. Bulletin of the Chemical Society of Japan, vol. 52 (3), 959-960 (1979).*
Drugs.com, Ferric Chloride, downloaded from the internet Mar. 27, 2014.*
Bottin et al. Chemical Communications, 1971, pp. 1087-1088.*
Fouace et al. Bioorg. Med. Chem. Lett. 11 (2001) 3011-3014.*
Kim et al., "Ginsenoside Rg3 inhibits phenylephrine-induced vascular contraction through induction of nitric oxide synthase," *British Journal of Pharmacology* 140:661-670 (2003).
Kim et al., "Effects of Ginsenoside $Rg_3$ Epimers on Swine Coronary Artery Contractions," *J. Ginseng Res.* 29(3):119-125 (2005).
Kim et al., "Anti-tumor Activity of the Ginsenoside Rk1 in Human Hepatocellular Carcinoma Cells through Inhibition of Telomerase Activity and Induction of Apoptosis," *Biol. Pharm. Bull.* 31(5):826-830 (2008).
International Preliminary Report on Patentability for International Application No. PCT/KR2010/007533, issued May 1, 2012 (English Language Translation Provided) (17 pages).
International Search Report for International Application No. PCT/KR2010/007533, issued Jul. 19, 2011, mailed Jul. 20, 2011 (3 pages).
Written Opinion for International Application No. PCT/KR2010/007533, mailed Jul. 20, 2011 (8 pages).
Lim et al., "The Effect of Ginsenoside Rk1 in Junctional Protein of Severe Preeclamptic Placenta," *Korean Journal of Obstetrics and Gynecology* 52(8): 301-308, 2009. (See abstract).
Schimmel et al., "Synthesis of Saponins with Cholestanol, Cholesterol, and Friedelanol as Aglycones," *Eur. J. Org. Chem.* 1701-1721, 2006.

* cited by examiner

*Primary Examiner* — Layla Bland
(74) *Attorney, Agent, or Firm* — Clark & Elbing LLP

(57) ABSTRACT

The present disclosure relates to a novel vascular leakage inhibitor. The novel vascular leakage inhibitor of the present disclosure inhibits the apoptosis of vascular endothelial cells, inhibits the formation of actin stress fibers induced by VEGF, enhances the cortical actin ring structure, and improves the stability of the tight junctions (TJs) between vascular cells, thereby inhibiting vascular leakage. The vascular leakage inhibitor of the present disclosure has the activity of not only reducing vascular permeability but also recovering the integrity of damaged blood vessels. Accordingly, the vascular leakage inhibitor of the present disclosure can prevent or treat various diseases caused by vascular leakage. Since the vascular leakage inhibitor of the present disclosure is synthesized from commercially available or easily synthesizable cholesterols, it has remarkably superior feasibility of commercial synthesis.

5 Claims, 42 Drawing Sheets

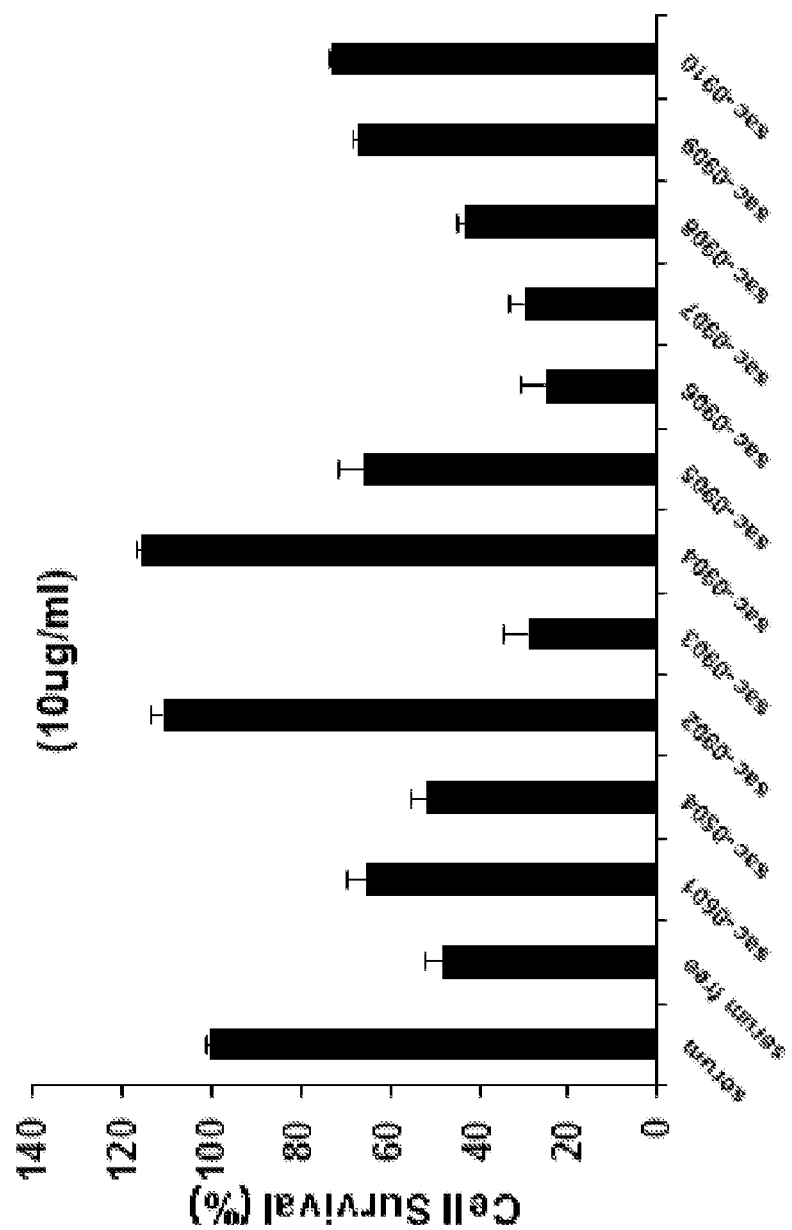

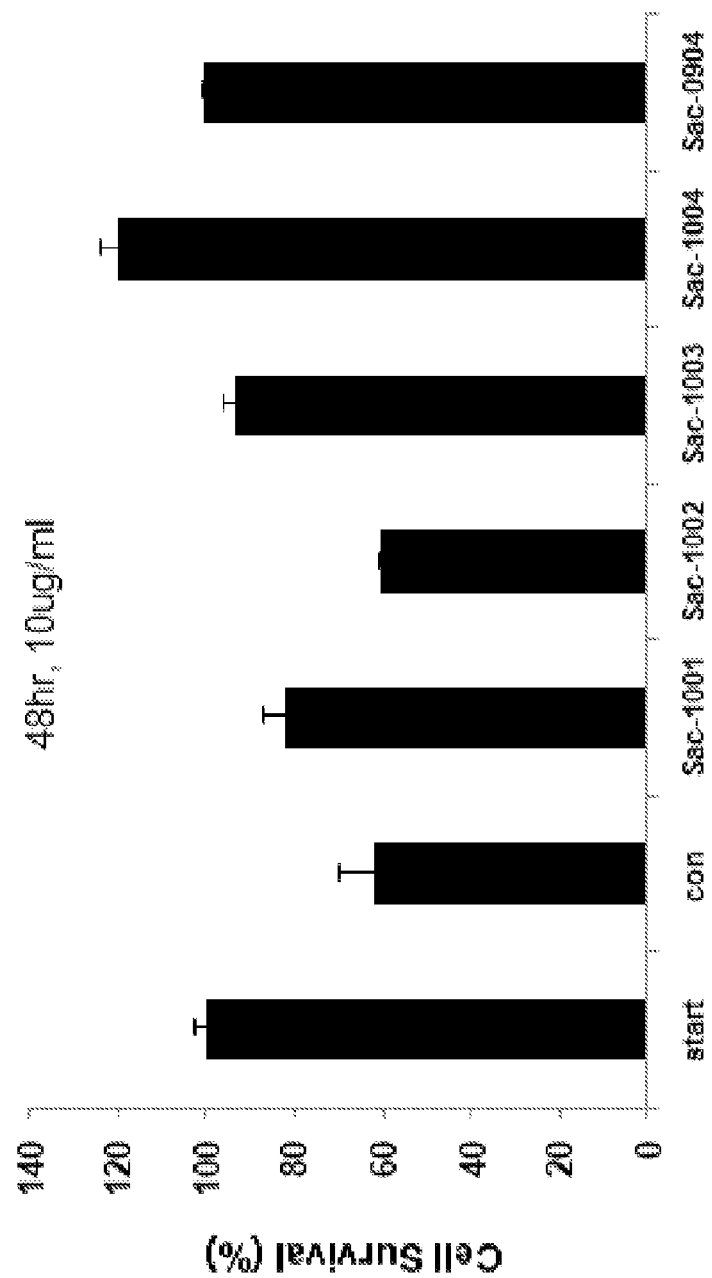

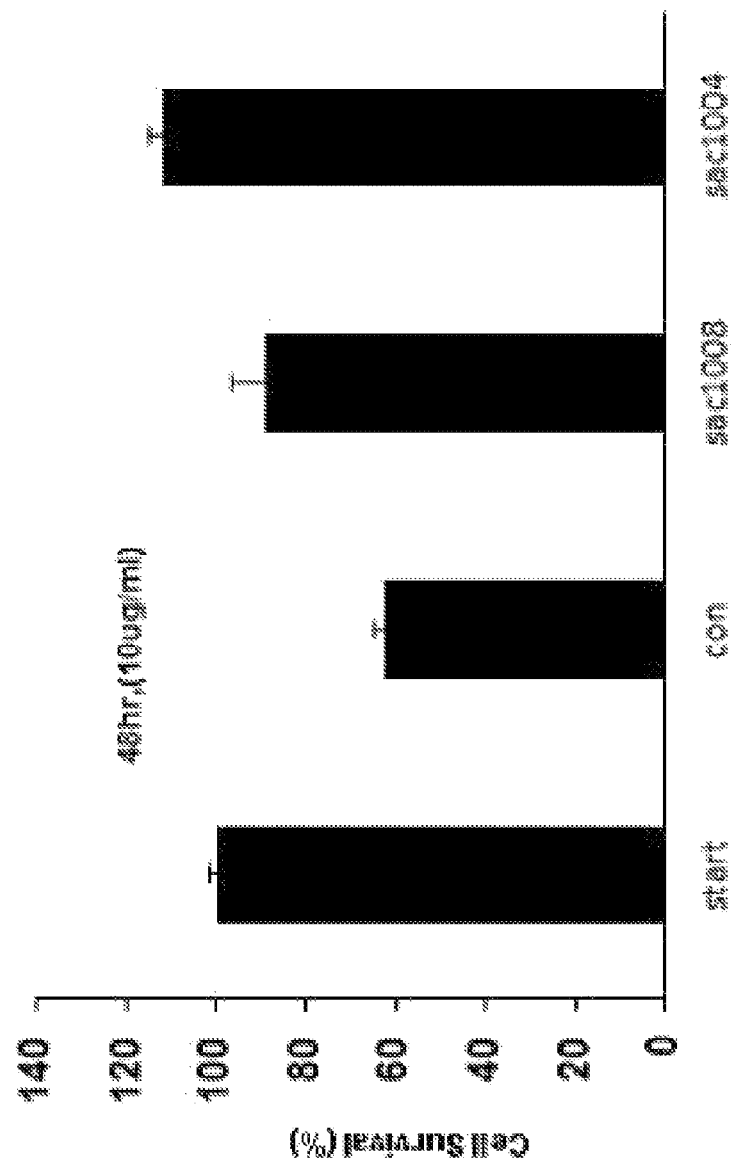

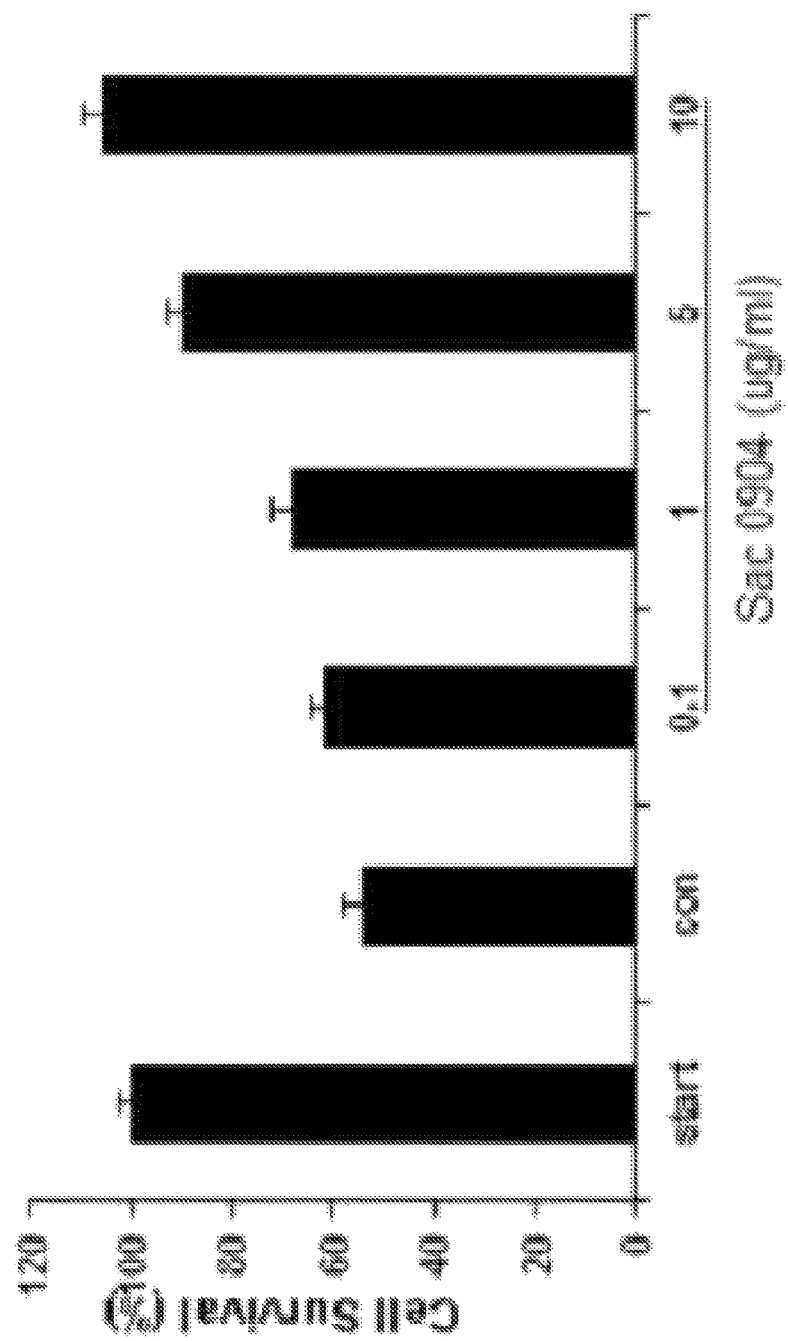

(Sac 0504 (ug/ml))

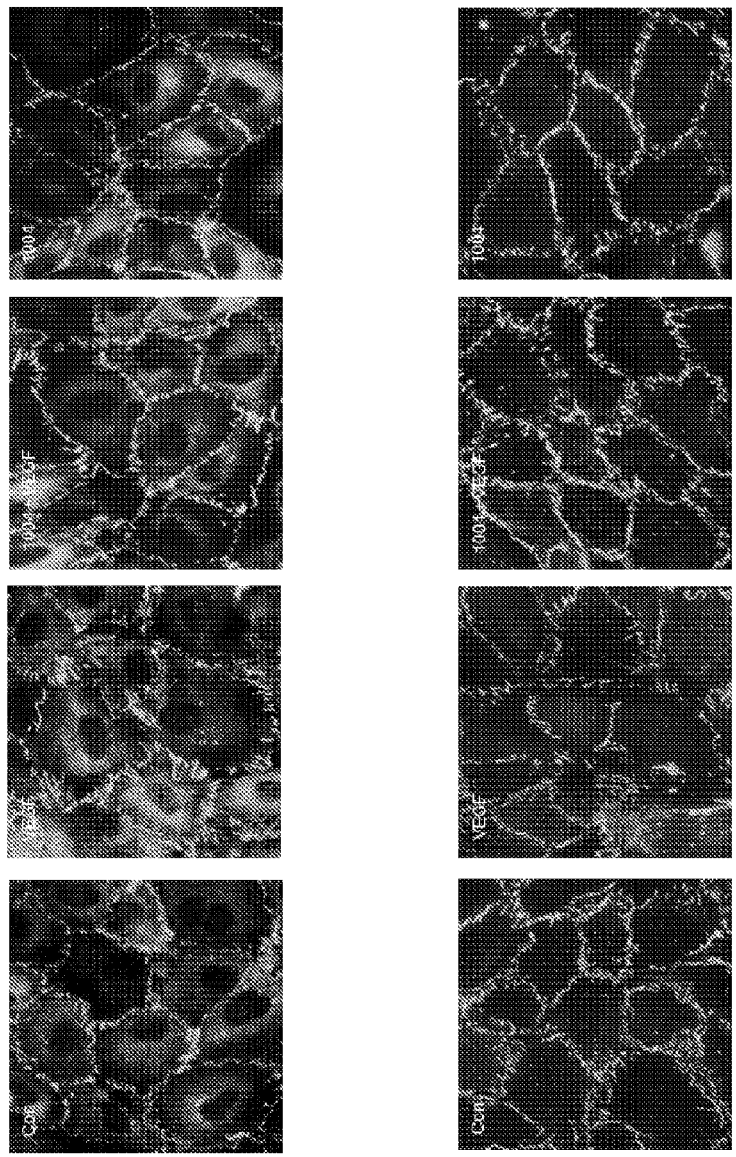

OCCLUDIN

ACTIN

VASCULAR LEAKAGE INHIBITOR

CROSS-REFERENCE TO RELATED APPLICATIONS

This application is the U.S. national stage filing under 35 U.S.C. §371 of international application PCT/KR2010/007533, filed Oct. 29, 2010, which claims benefit of Korean Patent Application 10-2009-0103450, filed Oct. 29, 2009.

BACKGROUND OF THE INVENTION

1. Field of the Invention

The present disclosure relates to a novel vascular leakage inhibitor.

2. Description of the Related Art

The disruption of endothelial barrier integrity leading to increased vascular permeability contributes to many pathological processes, including various inflammatory diseases, acute lung injury, and diabetic retinopathy [1, 2]. Endothelial permeability is tightly controlled by cell-cell junctions, including adherens junctions (AJs) and tight junctions (TJs), between neighboring endothelial cells [3, 4]. TJs consist of a number of proteins, including occludin, claudins, junctional adhesion molecules (JAMs), and zonula occludens (ZOs). Occludin, claudins, and JAMs are major integral transmembrane proteins with adhesive properties, and are believed to be responsible for the formation of a tight seal between two opposing endothelial membranes of adjacent cells [3]. Occludin and claudins form homodimeric bridges, and ZOs and cingulin connect these integral transmembrane proteins to actin filaments [5-7]. Dynamic regulation of perijunctional actin has been suggested to control paracellular permeability by affecting the stability of TJs closely connected to the actin cytoskeleton, either directly or indirectly [8, 9]. In fact, there are ample ultrastructural evidences to implicate the temporal expression, dynamic organization, and spatial distribution of the actin cytoskeleton in the alteration of TJ complexes under various conditions [10]. Therefore, actin is likely to play a critical role in modulating the integrity of TJs, and thus, endothelial permeability.

The reorganization of the actin cytoskeleton into the cortical actin ring and the concomitant redistribution of TJ proteins to the cell periphery is an inevitable event in endothelial barrier enhancement. Several molecules have been suggested to be important for the formation of the cortical actin ring [11]. Phosphorylated myosin light chain (p-MLC), and its kinase, myosin light chain kinase (MLCK), were observed to be distributed in the cortical region during EC barrier enhancement induced by sphingosine-1-phosphate (S1P) [12, 13], suggesting a potential role for spatially defined MLCK activation in regulating endothelial barrier function. MLC phosphorylation at the cortical region may promote the interaction of actin filaments and myosin, stabilizing the cortical actin ring structures, and thereby increasing the stability of TJ protein complexes in the cell periphery [11]. Cortactin, an F-actin binding protein, has also been implicated in cortical actin rearrangement [14]. Cortactin tyrosine phosphorylation and its translocation to the cortical actin have been associated with enhanced endothelial barrier function [13]. Furthermore, phosphorylated cortactin binds to MLCK via its SH3-domain in the cortical ring, implicating that cortactin-MLCK interaction at the site of cortical actin polymerization enhances barrier function by localizing the acto-myosin interaction at an optimal location [13].

Diabetic retinopathy (DR) is one of the most common vascular retinopathies and a leading cause of legal blindness in working-age adults [15]. The earliest sign of DR is leakage from retinal vessels due to breakdown of the blood-retinal barrier (BRB), which is followed by retinal edema and finally endothelial cell proliferation [16]. The BRB is a selective endothelial barrier of well-differentiated microvessels of the eye. The disruption of the BRB occurs during the earliest period of vascular retinopathy, which can be recovered before the irreversible angiogenesis characteristic of proliferative vascular retinopathy [17]. VEGF is known to play an important role in BRB breakdown by altering tight junction integrity and the cytoskeleton organization of endothelial cells, leading to increased permeability during the pathogenesis of DR [18, 19]. Therapies targeting this early and reversible stage of BRB breakdown remain to be developed.

Throughout this application, various publications and patents are referred and citations are provided in parentheses. The disclosures of these publications and patents in their entities are hereby incorporated by references into this application in order to fully describe the present disclosure and the state of the art to which this disclosure pertains.

SUMMARY OF THE INVENTION

The inventors of the present disclosure have studied and made efforts to develop substances capable of preventing or treating diseases caused by vascular leakage owing to damaged vascular integrity. As a result (they have synthesized substances having a molecular skeleton similar to that of ginsenosides Rk1 and Rg3, which have already been demonstrated to prevent vascular endothelial cell damage by the inventors of the present disclosure, and identified that these substances can prevent or treat diseases associated with vascular leakage by inhibiting apoptosis of vascular endothelial cells, inhibiting formation of actin stress fibers induced by VEGF, enhancing the cortical actin ring structure and improving the stability of tight junctions (TJs) between vascular endothelial cells.

The present disclosure is directed to providing a novel ginsenoside Rk1 and/or Rg3 analog.

The present disclosure is also directed to providing a pharmaceutical composition for preventing or treating diseases associated with vascular leakage.

The present disclosure is also directed to providing a food composition for preventing or treating diseases associated with vascular leakage.

The present disclosure is also directed to providing a method for preventing or treating diseases associated with vascular leakage.

Other features and aspects will be apparent from the following detailed description, drawings and claims.

DETAILED DESCRIPTION OF THIS INVENTION

In one general aspect, the present disclosure provides a compound represented by Chemical Formula 1 as a ginsenoside Rk1 or Rg3 analog:

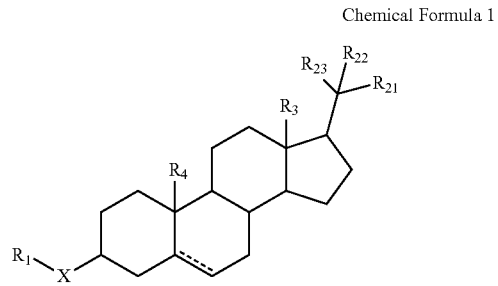

Chemical Formula 1 wherein X is oxygen or sulfur; $R_1$ is hydrogen, halo, $C_{1-30}$ alkyl, $C_{3-10}$ cycloalkyl, $C_{2-30}$ alkenyl, $C_{3-10}$ cycloalkenyl, $C_{2-15}$ heterocycloalkyl containing oxygen, sulfur or nitrogen as a heteroatom, $C_{3-15}$ heterocycloalkylalkyl containing oxygen, sulfur or nitrogen as a heteroatom, $C_{2-30}$ alkoxyalkyl, $C_{3-30}$ alkoxyalkoxyalkyl, heterocycloalkenyl containing oxygen, sulfur or nitrogen as a heteroatom, $C_{1-20}$ alcohol, $C_{1-20}$ alkenol, $C_{2-30}$ acyl, amide, $C_{1-10}$ amine, $C_{2-15}$ ester, sulfate, carboxyl, $C_{3-20}$ carboxyalkyl, $C_{3-20}$ carboxyalkenyl, $C_{3-20}$ alkylcarboxyl, $C_{3-20}$ alkenylcarboxyl, $C_{3-20}$ alkylcarboxyalkyl, $C_{3-20}$ alkylcarboxyalkenyl, $C_{3-20}$ alkenylcarboxyalkyl, $C_{4-20}$ alkenylcarboxyalkenyl, $C_{6-30}$ aryl, $C_{6-30}$ aralkyl, $C_{6-30}$ alkaryl, $C_{3-30}$ heteroaryl or $C_{6-30}$ arylcarbonyl containing nitrogen as a heteroatom; $R_{21}$ is $C_{2-30}$ alkyl, $C_{3-10}$ cycloalkyl, $C_{2-30}$ alkenyl, $C_{3-10}$ cycloalkenyl, $C_{2-30}$ carboxyalkyl, $C_{2-30}$ alkylcarboxyl, $C_{3-30}$ carboxyalkenyl, $C_{3-30}$ alkenylcarboxyl, $C_{3-30}$ alkylcarboxyalkyl, $C_{3-30}$ alkylcarboxyalkenyl, $C_{3-30}$ alkenylcarboxyalkyl, $C_{4-30}$ alkenylcarboxyalkenyl, $C_{2-10}$ heterocycloalkyl containing oxygen, sulfur or nitrogen as a heteroatom, $C_{3-10}$ heterocycloalkylalkyl containing oxygen, sulfur or nitrogen as a heteroatom, $C_{2-30}$ alkoxyalkyl, $C_{3-30}$ alkoxyalkoxyalkyl, heterocycloalkenyl containing oxygen, sulfur or nitrogen as a heteroatom, $C_{1-20}$ alcohol, $C_{1-20}$ alkenol, $C_{2-30}$ acyl, $C_{1-40}$ amide, $C_{1-10}$ amine or $C_{2-15}$ ester; $R_{22}$ is hydrogen, hydroxy, halo or $C_{1-10}$ alkyl; $R_{23}$ is hydrogen, hydroxy or $C_{1-10}$ alkyl; $R_{21}$ may form a double bond with the carbon to which $R_{22}$ and $R_{23}$ are bonded together; $R_{23}$ may form a double bond with the carbon to which $R_{21}$ and $R_{22}$ are bonded together; $R_{22}$ is nonexistent when $R_{21}$ or $R_{23}$ forms a double bond with the carbon; $R_3$ and $R_4$ are independently hydrogen or $C_{1-10}$ alkyl; and ------- is a single bond or a double bond.

In an exemplary embodiment of the present disclosure, the ginsenoside Rk1 or Rg3 analog of the present disclosure is represented by Chemical Formula 2:

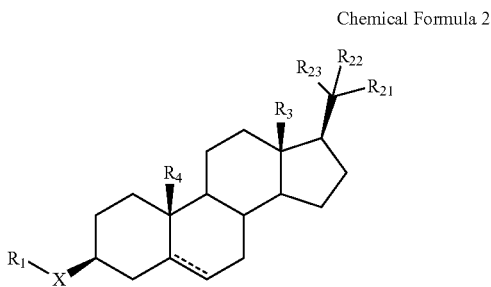

Chemical Formula 2 wherein X, $R_1$, $R_{21}$, $R_{22}$, $R_{23}$, $R_3$ and $R_4$ are the same as defined in Chemical Formula 1.

More specifically, the ginsenoside Rk1 or Rg3 analog of the present disclosure may be represented by Chemical Formula 3:

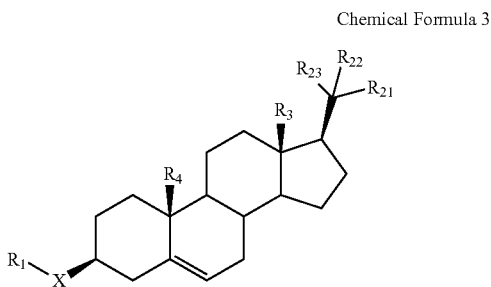

Chemical Formula 3 wherein X, $R_1$, $R_{21}$, $R_{22}$, $R_{23}$, $R_3$ and $R_4$ are the same as defined in Chemical Formula 1.

In another general aspect, the present disclosure provides a pharmaceutical composition for preventing or treating diseases associated with vascular leakage containing: (a) a pharmaceutically effective amount of the ginsenoside Rk1 or Rg3 analog; and (b) a pharmaceutically acceptable salt.

In another general aspect, the present disclosure provides a food composition for preventing or treating diseases associated with vascular leakage containing the ginsenoside Rk1 or Rg3 analog as an active ingredient.

In another general aspect, the present disclosure provides a method for preventing or treating diseases associated with vascular leakage including a step of administering the pharmaceutical composition to a subject in need thereof.

The inventors of the present disclosure have studied and made efforts to develop substances capable of preventing or treating diseases caused by vascular leakage owing to danged vascular integrity. As a result, they have synthesized substances having a molecular skeleton similar to that of ginsenosides Rk1 and Rg3, which have already been demonstrated to prevent vascular endothelial cell damage by the inventors of the present disclosure, and identified that these substances can prevent or treat diseases associated with vascular leakage by inhibiting apoptosis of vascular endothelial cells, inhibiting formation of actin stress fibers induced by VEGF, enhancing the cortical actin ring structure and improving the stability of tight junctions (TJs) between vascular cells.

The compound of the present disclosure represented by Chemical Formula 1 is chemically synthesized by mimicking the structure of ginsenosides Rk1 and Rg3, which have already been demonstrated to prevent vascular endothelial cell damage by the inventors of the present disclosure. Since ginsenosides Rk1 and Rg3 are extracted and isolated from expensive ginseng, they are not easily available. Thus, the inventors have made efforts to solve this problem and develop substances exhibiting improved physiological activity and pharmacological profile over ginsenosides Rk1 and Rg3. As a result, they have designed and synthesized the compound of the present disclosure.

The inventors have selected cholesterol, which has a molecular skeleton similar to that of ginsenosides Rk1 and Rg3, is easily commercially available and allows good synthetic approach, as a parent molecule and designed and synthesized various derivatives therefrom.

As used herein, the term "halo" used to define the ginsenoside Rk1 or Rg3 analog of Chemical Formula 1 refers to a halogen element and includes (for example, fluoro, chloro, bromo and iodo.

The term "alkyl" refers to a linear or branched, unsubstituted or substituted, saturated hydrocarbon group and includes; for example, methyl, ethyl, propyl, isobutyl, pentyl, hexyl, heptyl, octyl, nonyl, decyl, undecyl, tridecyl, pentadecyl, heptadecyl, etc. $C_{1-30}$ alkyl means an alkyl group having an alkyl unit of 1 to 30 carbons, excluding the number of carbons of a substituent when the $C_{1-30}$ alkyl is substituted, in Chemical Formula 1, the $C_{1-30}$ alkyl at $R_1$ may be specifically $C_{1-20}$ alkyl, more specifically $C_{1-15}$ alkyl, further more specifically $C_{1-10}$ alkyl, most specifically $C_{1-5}$ alkyl, in Chemical Formula 1, the $C_{2-15}$ alkyl at $R_{21}$ may be specifically $C_{3-10}$ alkyl, more specifically $C_{4-8}$ alkyl, most specifically branched $C_6$ alkyl. In Chemical Formula 1, the $C_{1-5}$ alkyl at $R_{22}$ may be specifically $C_{1-3}$ alkyl, more specifically $C_{1-2}$ alkyl. In Chemical Formula 1, the $C_{1-10}$ alkyl at $R_{23}$ may be specifically $C_{1-5}$ alkyl, more specifically $C_{1-3}$ alkyl, further more specifically $C_{1-2}$, alkyl. In Chemical Formula 1, the $C_{1-10}$ alkyl at $R_3$ or $R_4$ may be specifically $C_{1-5}$ alkyl, more specifically $C_{1-3}$ alkyl, further more specifically $C_{1-2}$ alkyl.

The term "cycloalkyl" refers to a cyclic hydrocarbon radical and includes cyclopropyl, cyclobutyl and cyclopentyl. $C_{3-10}$ cycloalkyl means cycloalkyl having 3-10 cyclic carbon atoms, excluding the number of carbons of a substituent when the $C_{3-10}$ cycloalkyl is substituted. In Chemical Formula 1, the cycloalkyl at $R_1$ may be specifically $C_{3-10}$ cycloalkyl, more specifically $C_{3-8}$ cycloalkyl. In Chemical Formula 1, the cycloalkyl at $R_{21}$ may be specifically $C_{3-10}$ cycloalkyl, more specifically $C_{3-8}$ cycloalkyl.

The term "alkenyl" refers to linear or branched, unsubstituted or substituted, unsaturated hydrocarbon group having given number of carbons and includes, for example, for example, ethenyl, vinyl, propenyl; allyl, isopropenyl, butenyl, isobutenyl, t-butenyl, n-pentenyl and n-hexenyl. $C_{2-30}$ alkenyl means an alkenyl group having an alkenyl unit of 1 to 30 carbons, excluding the number of carbons of a substituent when the $C_{2-30}$ alkenyl is substituted. In Chemical Formula 1, the $C_{2-30}$ alkenyl at $R_1$ may be specifically $C_{2-20}$ alkenyl, more specifically $C_{2-15}$ alkenyl, further more specifically $C_{2-10}$ alkenyl, most specifically $C_{2-5}$ alkenyl. In Chemical Formula 1, the $C_{2-15}$ alkenyl at $R_{21}$ may be specifically $C_{3-10}$ alkyl, more specifically $C_{4-8}$ alkyl, most specifically branched $C_6$ alkyl.

The term "cycloalkenyl" refers to a cyclic hydrocarbon group having at least one double bond and includes, for example, for example cyclopentene, cyclohexene and cyclohexadiene. $C_{3-10}$ cycloalkenyl means cycloalkenyl having 3-10 cyclic carbon atoms, excluding the number of carbons of a substituent when the $C_{3-10}$ cycloalkenyl is substituted. In Chemical Formula 1, the $C_{3-10}$ cycloalkenyl at $R_1$ may be specifically $C_{3-8}$ cycloalkenyl. In Chemical Formula 1, the cycloalkenyl at $R_{21}$ may be specifically $C_{3-8}$ cycloalkenyl.

The term "heterocycloalkyl containing oxygen, sulfur or nitrogen as a heteroatom" refers to a non-aromatic cyclic hydrocarbon group containing carbon, hydrogen and at least one heteroatom (oxygen, sulfur or nitrogen). The heteroatom may be specifically oxygen or sulfur, most specifically oxygen. The number of the heteroatom may be specifically 1-4, more specifically 1-3, further more specifically 1-2, most specifically 1. $C_{2-15}$ heterocycloalkyl means heterocycloalkyl having 2-15 cyclic carbon atoms. In Chemical Formula 1, the $C_{2-15}$ heterocycloalkyl at $R_1$ may be specifically $C_{2-10}$ heterocycloalkyl, more specifically $C_{3-8}$ heterocycloalkyl, further more specifically $C_{4-6}$ heterocycloalkyl, most specifically $C_5$ heterocycloalkyl. In Chemical Formula 1, the $C_{2-15}$ heterocycloalkyl at $R_{21}$ may be specifically $C_{2-10}$ heterocycloalkyl, more specifically $C_{3-8}$ heterocycloalkyl, further more specifically $C_{4-6}$ heterocycloalkyl, most specifically $C_5$ heterocycloalkyl.

The term "$C_{3-10}$ heterocycloalkylalkyl containing oxygen, sulfur or nitrogen as a heteroatom" refers to a non-aromatic cyclic hydrocarbon group containing carbon, hydrogen and at least one heteroatom (oxygen, sulfur or nitrogen). The heteroatom may be specifically oxygen or sulfur, most specifically oxygen. The number of the heteroatom may be specifically 1-4, more specifically 1-3, further more specifically 1-2, most specifically 1. $C_{3-15}$ heterocycloalkylalkyl means heterocycloalkylalkyl having 3-15 cyclic and acyclic carbon atoms. Specifically, it may have 1-5 acyclic carbon atoms. In an exemplary embodiment of the present disclosure, the alkyl moiety of the heterocycloalkylalkyl may be methylene. In Chemical Formula 1, the $C_{3-15}$ heterocycloalkylalkyl at $R_1$ may be specifically $C_{3-10}$ heterocycloalkylalkyl, more specifically $C_{3-6}$ heterocycloalkylalkyl. In Chemical Formula 1, the $C_{3-10}$ heterocycloalkylalkyl at $R_{21}$ may be specifically $C_{3-6}$ heterocycloalkylalkyl.

The term "alkoxyalkyl" refers to an alkyl group substituted with an alkoxy group. $C_{2-30}$ alkoxyalkyl means an alkoxyalkyl group having an alkoxyalkyl unit of 2-30 carbons, excluding the number of carbons of a substituent when the $C_{2-30}$ alkoxyalkyl is substituted. In Chemical Formula 1, the $C_{2-30}$ alkoxyalkyl at $R_1$ may be specifically $C_{2-20}$ alkoxyalkyl, more specifically $C_{2-10}$ alkoxyalkyl, further more specifically $C_{2-8}$ alkoxyalkyl, most specifically $C_{2-6}$ alkoxyalkyl. In Chemical Formula 1, the $C_{2-30}$ alkoxyalkyl at $R_{21}$ may be specifically $C_{2-20}$ alkoxyalkyl, more specifically $C_{2-10}$ alkoxyalkyl.

The term "alkoxyalkoxyalkyl" refers to an alkyl group substituted with an alkoxyalkoxy group (alkoxy-alkoxyalkyl-). $C_{3-30}$ alkoxyalkoxyalkyl means an alkoxyalkoxyalkyl group having an alkoxyalkoxyalkyl unit of 3-30 carbons, excluding the number of carbons of a substituent when the $C_{3-30}$ alkoxyalkyl is substituted. In Chemical Formula 1, the $C_{3-30}$ alkoxyalkoxyalkyl at $R_1$ may be specifically $C_{3-20}$ alkoxyalkoxyalkyl, more specifically $C_{3-10}$ alkoxyalkoxyalkyl, further more specifically $C_{3-8}$ alkoxyalkoxyalkyl, most specifically $C_{3-6}$ alkoxyalkoxyalkyl. In Chemical Formula 1, the $C_{3-30}$ alkoxyalkoxyalkyl at $R_{21}$ may be specifically $C_{3-20}$ alkoxyalkoxyalkyl, more specifically $C_{3-10}$ alkoxyalkoxyalkyl.

The term "heterocycloalkenyl containing oxygen, sulfur or nitrogen as a heteroatom" refers to non-aromatic cyclic hydrocarbon group containing carbon, hydrogen, at least one heteroatom (oxygen, sulfur or nitrogen) and at least one double bond. The heteroatom may be specifically oxygen or sulfur, most specifically oxygen. The number of the heteroatoms may be specifically 1-4, more specifically 1-3, further more specifically 1-2, most specifically 1. $C_{3-10}$ heterocycloalkenyl means heterocycloalkenyl having 3-10 cyclic carbon atoms. In Chemical Formula 1, the $C_{3-10}$ heterocycloalkenyl at $R_1$ may be specifically $C_{3-9}$ heterocycloalkenyl, more specifically $C_{3-8}$ heterocycloalkenyl, further more specifically $C_{4-6}$ heterocycloalkenyl, most specifically $C_5$ heterocycloalkenyl. In Chemical Formula 1, the $C_{3-10}$ heterocycloalkenyl at $R_{21}$ may be specifically $C_{3-9}$ heterocycloalkenyl, more specifically $C_{3-8}$ heterocycloalkenyl.

The term "alcohol" refers to a compound in which a hydroxyl group is bound to the carbon atom of alkyl or a substituted alkyl group. $C_{1-20}$ alcohol means an alcohol compound having an alcohol unit of 1-20 carbons, excluding the number of carbons of a substituent when the $C_{1-20}$ alcohol is substituted. In Chemical Formula 1, the $C_{1-20}$ alcohol at $R_1$ may be specifically $C_{1-15}$ alcohol, more specifically $C_{1-10}$ alcohol, further more specifically $C_{1-5}$ alcohol. In Chemical Formula 1, the $C_{1-20}$ alcohol at $R_{21}$ may be specifically $C_{3-15}$ alcohol, more specifically $C_{3-10}$ alcohol, further more specifically $C_{5-8}$ alcohol.

The term "alkenol" refers to a compound in which a hydroxyl group is bound to the carbon atom of alkenyl or a substituted alkenyl group. $C_{1-20}$ alkenol means an alkenol compound having an alkenol unit of 1-10 carbons, excluding the number of carbons of a substituent when the $C_{1-20}$ alkenol is substituted. In Chemical Formula 1, the $C_{1-20}$ alkenol at $R_1$ may be specifically $C_{1-15}$ alkenol, more specifically $C_{1-10}$ alkenol, further more specifically $C_{1-5}$ alkenol. In Chemical Formula 1, the $C_{1-20}$ alkenol at $R_{21}$ may be specifically $C_{3-15}$ alkenol, more specifically $C_{3-10}$ alkenol, further more specifically $C_{5-8}$ alkenol.

The term "acyl" refers to a radical derived by the removal of a hydroxyl group from a carboxylic acid. $C_{2-30}$ acyl means an acyl group having an acyl unit of 2-30 carbons, excluding the number of carbons of a substituent when the $C_{2-30}$ acyl is substituted. In Chemical Formula 1, the $C_{2-30}$ acyl at $R_1$ may be specifically $C_{2-10}$ acyl. In Chemical Formula 1, the $C_{2-30}$ acyl at $R_{21}$ may be specifically $C_{2-10}$ acyl.

The term "amide" refers to a functional group comprising an acyl group bound to a nitrogen atom, $C_{1-10}$ amide means an amide group having an amide unit of 1-10 carbons, excluding the number of carbons of a substituent when the $C_{1-10}$ amide is substituted. In Chemical Formula 1, the $C_{1-10}$ amide at $R_1$ may be specifically $C_{1-5}$ amide, more specifically $C_{1-3}$ amide. In Chemical Formula 1, the $C_{1-10}$ amide at $R_{21}$ may be specifically $C_{3-9}$ amide.

The term "amine" refers to a functional group containing a basic nitrogen atom with a lone pair, $C_{1-10}$ amine means an amine group having an amine unit of 1-10 carbons, excluding the number of carbons of a substituent when the $C_{1-10}$ amine is substituted. In Chemical Formula 1, the $C_{1-10}$ amine at $R_1$ at may be specifically $C_{1-5}$ amine, more specifically $C_{1-3}$ amine. In Chemical Formula 1, the $C_{1-10}$ amine at $R_{21}$ may be specifically $C_{3-9}$ amine.

The term "ester" refers to a functional group represented by RCOO— (R is alkyl or aryl). $C_{2-15}$ ester means an ester group having an ester unit of 2-15 carbons, excluding the number of carbons of a substituent when the $C_{2-15}$ ester is substituted. In Chemical Formula 1, $R_1$ the $C_{2-15}$ ester at $R_1$ may be specifically $C_{2-10}$ ester, more specifically $C_{2-5}$ ester. In Chemical Formula 1, the $C_{2-15}$ ester at $R_{21}$ may be specifically $C_{3-9}$ ester.

The term "carboxyl" refers to a functional group represented by —COOH.

The term "carboxyalkyl" refers to an alkyl group to which carboxyl is bound. $C_{3-20}$ carboxyalkyl means a carboxyalkyl group having a carboxyalkyl unit of 3-20 carbons, excluding the number of carbons of a substituent when the $C_{3-20}$ carboxyalkyl is substituted. $C_{3-20}$ carboxyalkyl means a carboxyalkyl group having a carboxyalkyl unit of 3-20 carbons, excluding the number of carbons of a substituent when the $C_{3-20}$ carboxyalkyl is substituted. In Chemical Formula 1, the $C_{3-20}$ carboxyalkyl at $R_1$ may be specifically $C_{3-10}$ carboxyalkyl, more specifically $C_{3-5}$ carboxyalkyl. In Chemical Formula 1, the $C_{2-30}$ carboxyalkyl at $R_{21}$ may be specifically $C_{3-15}$ carboxyalkyl, more specifically $C_{1-10}$ carboxyalkyl.

The term "carboxyalkenyl" refers to an alkenyl group to which carboxyl is bound. $C_{3-20}$ carboxyalkenyl means a carboxyalkenyl group having a carboxyalkenyl unit of 3-20 carbons, excluding the number of carbons of a substituent when the $C_{3-20}$ carboxyalkenyl is substituted. In Chemical Formula 1, the $C_{3-20}$ carboxyalkenyl at $R_1$ may be specifically $C_{3-10}$ carboxyalkenyl, more specifically $C_{3-6}$ carboxyalkenyl. In Chemical Formula 1, the $C_{3-30}$ carboxyalkenyl at $R_{21}$ may be specifically $C_{3-15}$ carboxyalkenyl, more specifically $C_{4-10}$ carboxyalkenyl.

The term "alkylcarboxyl" refers to a carboxyl group to which alkyl is bound. $C_{3-20}$ alkylcarboxyl means an alkylcarboxyl group having an alkylcarboxyl unit of 3-20 carbons, excluding the number of carbons of a substituent when the $C_{3-20}$ alkylcarboxyl is substituted. In Chemical Formula 1, the $C_{3-20}$ alkylcarboxyl at $R_1$ may be specifically $C_{3-10}$ alkylcarboxyl, more specifically $C_{3-6}$ alkylcarboxyl. In Chemical Formula 1, the $C_{2-30}$ alkylcarboxyl at $R_{21}$ may be specifically $C_{3-15}$ alkylcarboxyl, more specifically $C_{1-10}$ alkylcarboxyl.

The term "alkenylcarboxyl" refers to a carboxyl group to which alkenyl is bound. $C_{3-20}$ alkenylcarboxyl means an alkenylcarboxyl group having an alkenylcarboxyl unit of 3-20 carbons, excluding the number of carbons of a substituent when the $C_{3-20}$ alkenylcarboxyl is substituted. In Chemical Formula 1, the $C_{3-20}$ alkenylcarboxyl at $R_1$ may be specifically $C_{3-10}$ alkenylcarboxyl, more specifically $C_{3-10}$ alkenylcarboxyl. In Chemical Formula 1, the $C_{3-30}$ alkenylcarboxyl at $R_{21}$ may be specifically $C_{3-15}$ alkenylcarboxyl, more specifically $C_{4-10}$ alkenylcarboxyl.

The term "alkylcarboxyalkyl" refers to an alkyl-C(O)—O-alkyl group. $C_{3-20}$ alkylcarboxyalkyl means an alkylcarboxyalkyl group having an alkylcarboxyalkyl unit of 3-20 carbons, excluding the number of carbons of a substituent when the $C_{3-20}$ alkylcarboxyalkyl is substituted. In Chemical Formula 1, the $C_{3-20}$ alkylcarboxyalkyl at $R_1$ may be specifically $C_{3-10}$ alkylcarboxyalkyl, more specifically $C_{3-10}$ alkylcarboxyalkyl. In Chemical Formula 1, the $C_{3-30}$ alkylcarboxyalkyl at $R_{21}$ may be specifically $C_{3-15}$ alkylcarboxyalkyl, more specifically $C_{4-10}$ alkylcarboxyalkyl.

The term "alkylcarboxyalkenyl" refers to an alkyl-O—C(O)-alkenyl group. $C_{3-20}$ alkylcarboxyalkenyl means an alkylcarboxyalkenyl group having an alkylcarboxyalkenyl unit of 3-20 carbons, excluding the number of carbons of a substituent when the $C_{3-20}$ alkylcarboxyalkenyl is substituted, in Chemical Formula 1, the $C_{3-20}$ alkylcarboxyalkenyl at $R_1$ may be specifically $C_{3-10}$ alkylcarboxyalkenyl, more specifically $C_{3-6}$ alkylcarboxyalkenyl, in Chemical Formula 1, the $C_{3-30}$ alkylcarboxyalkenyl at $R_{21}$ may be specifically $C_{3-15}$ alkylcarboxyalkenyl, more specifically $C_{4-10}$ alkylcarboxyalkenyl.

The term "alkenylcarboxyakyl" refers to an alkenyl-O—C(O)-alkyl group. $C_{3-20}$ alkenylcarboxyalkyl means an alkenylcarboxyalkyl group having an alkenylcarboxyalkyl unit of 3-20 carbons, excluding the number of carbons of a substituent when the $C_{3-20}$ alkenylcarboxyalkyl is substituted. In Chemical Formula 1, the $C_{3-20}$ alkenylcarboxyalkyl at $R_1$ may be specifically $C_{3-10}$ alkenylcarboxyalkyl, more specifically $C_{3-6}$ alkenylcarboxyalkyl, in Chemical Formula 1, the $C_{3-30}$ alkenylcarboxyalkyl at $R_{21}$ may be specifically $C_{3-15}$ alkenylcarboxyalkyl, more specifically $C_{4-10}$ alkenylcarboxyalkyl.

The term "alkenylcarboxyalkenyl" refers to an alkenyl-O—C(O)-alkenyl group. $C_{4-20}$ alkenylcarboxyalkenyl means an alkenylcarboxyalkenyl group having an alkenylcarboxyalkenyl unit of 4-20 carbons, excluding the number of carbons of a substituent when the $C_{4-20}$ alkenylcarboxyalkenyl is substituted.

The term "aryl" refers to a substituted or unsubstituted, monocyclic or polycyclic carbon ring which is entirely or partially unsaturated, $C_{6-30}$ aryl means an aryl group having 6-30 cyclic carbon atoms, excluding the number of carbons of a substituent when the $C_{6-30}$ aryl is substituted. Specifically, the aryl may be monoaryl or biaryl. The monoaryl may have 5-6 carbons, and the biaryl may have 9-1.0 carbons. Most specifically, the aryl may be substituted or unsubstituted phenyl. When the monoaryl, e.g., phenyl, is substituted, it may have various substituents at various positions. For example, it may be substituted with halo, hydroxy, nitro, cyano, $C_1$-$C_4$ substituted or unsubstituted, linear or branched alkyl, or $C_1$-$C_4$ linear or branched alkoxy.

The term "aralkyl" refers to an alkyl group substituted with an aryl group. $C_{6-30}$ aralkyl means aralkyl having an aralkyl unit of 6-30 carbons, excluding the number of carbons of a substituent when the $C_{6-30}$ aralkyl is substituted. In the aralkyl, the aryl may be specifically monoaryl or biaryl, and the alkyl may be specifically $C_{1-3}$ alkyl, more specifically $C_1$ alkyl. In the aralkyl, the aryl may have various substituents at various positions. For example, it may be substituted with halo, hydroxy, nitro, cyano, $C_1$-$C_4$ substituted or unsubstituted, linear or branched alkyl, $C_1$-$C_4$ linear or branched alkoxy or alkylcarboxylnitro.

The term "alkaryl" refers to an aryl group substituted with an alkyl group. $C_{6-30}$ alkaryl means alkaryl having an alkaryl unit of 6-30 carbons, excluding the number of carbons of a substituent when the $C_{6-30}$ alkaryl is substituted. In the alkaryl, the aryl may be specifically monoaryl or biaryl, and the alkyl may be specifically $C_{1-10}$ alkyl, more specifically $C_{1-5}$ alkyl. In the alkaryl, the aryl may have various substituents at various positions. For example, it may be substituted with halo, hydroxy, nitro, cyano, $C_1$-$C_4$ substituted or unsubstituted, linear or branched alkyl, or $C_1$-$C_4$ linear or branched alkoxy.

The term "heteroaryl containing nitrogen as a heteroatom" refers to a heterocyclic aromatic group which contains N as a heteroatom. $C_{3-30}$ heteroaryl means a heteroaryl group having a cyclic carbon atom of 3-30 carbons, excluding the number of carbons of a substituent when the $C_{3-30}$ heteroaryl is substituted. The number of the heteroatoms may be 1-4, specifically 1-2. In the heteroaryl, the aryl may be specifically monoaryl or biaryl, most specifically monoaryl. The heteroaryl may have various substituents at various positions. For example, it may be substituted with halo, hydroxy, nitro, cyano, $C_1$-$C_4$ substituted or unsubstituted, linear or branched alkyl, or $C_1$-$C_4$ linear or branched alkoxy.

The term "arylcarbonyl" refers to "aryl-C(O)—". $C_{6-30}$ arylcarbonyl means arylcarbonyl having an arylcarbonyl unit of 6-30 carbons, excluding the number of carbons of a substituent when the $C_{6-30}$ arylcarbonyl is substituted, in the arylcarbonyl, the aryl may be specifically monoaryl or biaryl, more specifically monoaryl. In the arylcarbonyl, the aryl may have various substituents at various positions. For example, it may be substituted with halo, hydroxy, nitro, cyano, $C_1$-$C_4$ substituted or unsubstituted, linear or branched alkyl, $C_1$-$C_4$ linear or branched alkoxy or alkylcarboxylnitro.

In an exemplary embodiment of the present disclosure, $R_1$ is hydrogen, halo, $C_{1-10}$ alkyl, $C_{3-8}$ cycloalkyl, $C_{2-10}$ alkenyl, $C_{3-8}$ cycloalkenyl, $C_{2-8}$ heterocycloalkyl containing oxygen, sulfur or nitrogen as a heteroatom, $C_{3-10}$ heterocycloalkylalkyl containing oxygen, sulfur or nitrogen as a heteroatom, $C_{2-20}$ alkoxyalkyl, $C_{3-20}$ alkoxyalkoxyalkyl, $C_{3-8}$ heterocycloalkenyl containing oxygen, sulfur or nitrogen as a heteroatom, $C_{1-10}$ alcohol, $C_{1-10}$ alkenol, $C_{2-20}$ acyl, $C_{1-10}$ amide, $C_{1-5}$ amine, $C_{2-15}$ ester, sulfate, carboxyl, $C_{3-20}$ carboxyalkyl, $C_{3-20}$ carboxyalkenyl, $C_{3-20}$ alkylcarboxyl, $C_{3-20}$ alkenylcarboxyl, $C_{3-20}$ alkylcarboxyalkyl, $C_{3-20}$ alkylcarboxyalkenyl, $C_{3-20}$ alkenylcarboxyalkyl, $C_{4-20}$ alkenylcarboxyalkenyl, $C_{6-20}$ aryl, $C_{6-20}$ aralkyl, $C_{6-20}$ alkaryl, $C_{3-20}$ heteroaryl containing nitrogen as a heteroatom or $C_{6-20}$ arylcarbonyl.

More specifically, $R_1$ is hydrogen, $C_{1-10}$ alkyl, $C_{3-8}$ cycloalkyl, $C_{2-10}$ alkenyl, $C_{3-8}$ cycloalkenyl, $C_{2-8}$ heterocycloalkyl containing oxygen as a heteroatom, $C_{3-10}$ heterocycloalkylalkyl containing oxygen as a heteroatom, $C_{2-20}$ alkoxyalkyl, $C_{3-10}$ alkoxyalkoxyalkyl, $C_{3-8}$ heterocycloalkenyl containing oxygen as a heteroatom, alcohol, $C_{1-10}$ alkenol, $C_{1-10}$ amide, $C_{1-5}$ amine, $C_{2-15}$ ester, sulfate, carboxyl, $C_{3-20}$ carboxyalkyl, $C_{3-20}$ carboxyalkenyl, $C_{3-20}$ alkylcarboxyl, $C_{3-20}$ alkenylcarboxyl, $C_{3-20}$ alkylcarboxyalkyl, $C_{3-20}$ alkylcarboxyalkenyl, $C_{3-20}$ alkenylcarboxyalkyl, $C_{3-20}$ alkenylcarboxyalkenyl, $C_{1-20}$ alkenylcarboxyalkyl, $C_{6-20}$ aryl, $C_{6-20}$ aralkyl, $C_{6-20}$ alkaryl, $C_{3-20}$ heteroaryl containing nitrogen as a heteroatom or $C_{6-20}$ arylcarbonyl.

In an exemplary embodiment of the present disclosure, in $R_1$, the cycloalkyl or heterocycloalkyl may be substituted with hydroxy, halo, $C_{1-5}$ alkyl, $C_{1-5}$ alcohol, $C_{1-5}$ alkoxy, $C_{2-8}$ alkoxyalkyl; $C_{6-20}$ aryl, $C_{7-20}$ arylcarboxyl or a combination thereof; the $C_{3-10}$ cycloalkenyl or heterocycloalkenyl may be substituted with hydroxy, halo, $C_{1-5}$ alkyl, $C_{2-8}$ alkylcarboxyl, $C_{3-8}$ alkylcarboxylalkyl, $C_{1-5}$ alcohol, $C_{1-5}$ alkoxy, $C_{2-43}$ alkoxyalkyl, $C_{5-20}$ aryl, $C_{7-20}$ arylcarboxyl or a combination thereof; the aryl may be substituted with hydroxy, halo, $C_{1-5}$ alkyl, $C_{1-5}$ alcohol, $C_{1-5}$ alkoxy, $C_{2-8}$ alkoxyalkyl, nitro, $C_{2-8}$ alkylcarboxylamino or a combination thereof; the aralkyl may be substituted with hydroxy, halo, alkyl, $C_{1-5}$ alcohol, $C_{1-5}$ alkoxy, $C_{2-8}$ alkoxyalkyl, nitro, $C_{2-8}$ alkylcarboxylamino or a combination thereof; the alkaryl may be substituted with hydroxy, halo, $C_{1-5}$ alkyl, $C_{1-5}$ alcohol, $C_{1-5}$ alkoxy, $C_{2-8}$ alkoxyalkyl, nitro, $C_{2-8}$ alkylcarboxylamino or a combination thereof; the arylcarbonyl may be substituted with hydroxy, halo, $C_{1-5}$ alkyl, $C_{1-5}$ alcohol, alkoxy, $C_{2-8}$ alkoxyalkyl, nitro, $C_{2-8}$ alkylcarboxylamino or a combination thereof; and the heteroaryl may be substituted with hydroxy, halo, $C_{1-5}$ alkyl, $C_{1-5}$ alcohol, alkoxy, $C_{2-8}$ alkoxyalkyl, nitro, $C_{2-8}$ alkylcarboxylamino or a combination thereof.

As demonstrated through the following examples, when $R_1$ is heterocycloalkyl or heterocycloalkenyl, the effect of preventing or treating vascular leakage is very superior. When $R_1$ is heterocycloalkyl, it may not unsubstituted. When $R_1$ is heterocycloalkenyl, it may be substituted with $C_{2-8}$ alkylcarboxyl (for example, $CH_3CO$—O—) and/or $C_{3-8}$ alkylcarboxylalkyl (for example, $CH_3CO$—O—$CH_2$—).

In an exemplary embodiment of the present disclosure, $R_{21}$ is linear or branched $C_{2-15}$ alkyl, $C_{3-10}$ cycloalkyl, $C_{2-15}$ alkenyl, $C_{3-10}$ cycloalkenyl, $C_{2-15}$ carboxyalkyl, $C_{2-15}$ alkylcarboxyl, $C_{3-15}$ carboxyalkenyl, $C_{2-15}$ alkenylcarboxyl, alkylcarboxyalkyl, alkylcarboxyalkenyl, $C_{3-15}$ alkenylcarboxyalkyl, $C_{2-30}$ alkenylcarboxyalkenyl, $C_{2-10}$ heterocycloalkyl containing oxygen, sulfur or nitrogen as a heteroatom, $C_{3-10}$ heterocycloalkylalkyl containing oxygen, sulfur or nitrogen as a heteroatom, $C_{2-20}$ alkoxyalkyl, $C_{3-30}$ alkoxyalkoxyalkyl, $C_{3-10}$ heterocycloalkenyl containing oxygen, sulfur or nitrogen as a heteroatom, $C_{1-20}$ alcohol, $C_{1-20}$ alkenol, $C_{2-30}$ acyl, $C_{1-10}$ amide, $C_{1-10}$ amine or $C_{2-15}$ ester. $R_{21}$ may form a double bond with the carbon (hereinafter, referred to as the central carbon) to which $R_{22}$ and $R_{23}$ are bonded together. When $R_{21}$ forms a double bond with the central carbon, $R_{22}$ is nonexisten.

When $R_{21}$ forms a double bond with the central carbon, $R_1$ may be heterocycloalkyl or heterocycloalkenyl, and, when $R_1$ is heterocycloalkyl, it may be unsubstituted. When $R_1$ is heterocycloalkenyl, it may be substituted with $C_{2-8}$ alkylcarboxyl (for example, $CH_3CO$—O—O—) and/or $C_{3-8}$ alkylcarboxylalkyl (for example, $CH_3CO$—O—O—$CH_2$—.

When $R_{21}$ forms a double bond with the central carbon, $R_{21}$ may be branched $C_{5-7}$ alkyl, $C_{4-7}$/carboxyalkyl or $C_{5-8}$ $C_{4-7}$ alkylcarboxyalkyl.

In an exemplary embodiment of the present disclosure, $R_{22}$ is hydrogen, hydroxy or $C_{1-5}$ alkyl.

In an exemplary embodiment of the present disclosure; $R_{23}$ is $C_{1-5}$ alkyl or forms a double bond with the carbon to which $R_{21}$ and $R_{22}$ are bonded together. When $R_{23}$ forms a double bond with the central carbon, $R_{22}$ is nonexisten.

In an exemplary embodiment of the present disclosure, $R_3$ and $R_4$ are independently $C_{1-5}$ alkyl, more specifically $C_{1-3}$ alkyl; further more specifically $C_{1-2}$ alkyl, most specifically methyl.

In Chemical Formula 1, X may be oxygen or sulfur, specifically oxygen.

In Chemical Formula 1, ....... is a single bond or a double bond, specifically a double bond.

In an exemplary embodiment of the present disclosure, in Chemical Formula 1, X is oxygen; $R_1$ is hydrogen, $C_{3-10}$ alkyl, $C_{3-10}$ cycloalkyl, $C_{3-15}$ alkenyl, $C_{3-10}$ cycloalkenyl, $C_{3-15}$ heterocycloalkyl containing oxygen, sulfur or nitrogen as a heteroatom, $C_{3-15}$ heterocycloalkylalkyl containing oxygen, sulfur or nitrogen as a heteroatom, $C_{2-30}$ alkoxyalkyl, $C_{3-30}$ alkoxyalkoxyalkyl, $C_{3-10}$ heterocycloalkenyl containing oxygen, sulfur or nitrogen as a heteroatom, $C_{3-20}$ alcohol, $C_{3-20}$ alkenol, $C_{1-10}$ amide, sulfate, $C_{3-20}$ carboxyalkyl, $C_{3-20}$ carboxyalkenyl, $C_{3-20}$ alkylcarboxyl, $C_{3-20}$ alkenylcarboxyl, $C_{3-20}$ alkylcarboxyalkyl, $C_{3-20}$ alkylcarboxyalkyl, $C_{3-20}$ alkenylcarboxyalkyl, $C_{1-20}$ alkenylcarboxyalkenyl, $C_{6-30}$ aryl, $C_{6-30}$ aralkyl, $C_{6-30}$ alkaryl, $C_{3-30}$ heteroaryl containing nitrogen as a heteroatom or $C_{6-30}$ arylcarbonyl; $R_{21}$ is $C_{3-15}$ alkyl, $C_{3-15}$ alkenyl, $C_{2-15}$ carboxyalkyl, $C_{2-15}$ alkylcarboxy, $C_{3-15}$ carboxyalkenyl, $C_{3-15}$ alkenylcarboxyl, $C_{3-15}$ alkylcarboxyalkyl, $C_{3-15}$ alkylcarboxyalkenyl, $C_{3-15}$ alkenylcarboxyalkyl, $C_{4-30}$ alkenylcarboxyalkenyl, $C_{3-15}$alkoxyalkyl, $C_{3-15}$ alkoxyalkoxyalkyl, $C_{3-20}$ alcohol or $C_{3-20}$ alkenol; $R_{22}$ is hydrogen, hydroxy or $C_{1-3}$ alkyl; $R_{23}$ is $C_{1-5}$ alkyl; $R_{21}$ may form a double bond with the carbon to which $R_{22}$ and $R_{23}$ are bonded together; $R_{23}$ may form a double bond with the carbon to which $R_{21}$ and $R_{22}$ are bonded together; when $R_{21}$ or $R_{23}$ forms a double bond with the double bond, is nonexistent; $R_3$ and $R_4$ are independently hydrogen or $C_{1-3}$ alkyl; and ‥‥‥ is a single bond or a double bond.

In an exemplary embodiment of the present disclosure, the ginsenoside Rk1 or Rg3 analog of the present disclosure is a compound represented by a chemical formula selected from a group consisting of Chemical Formulae 4 to 46:

Chemical Formula 4

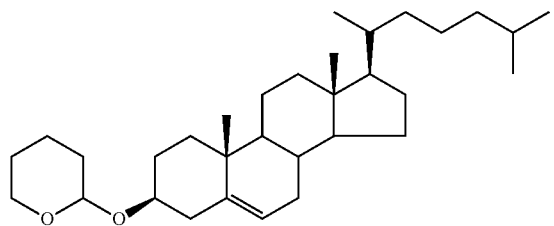

Chemical Formula 5

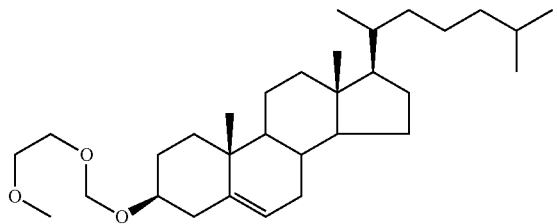

Chemical Formula 6

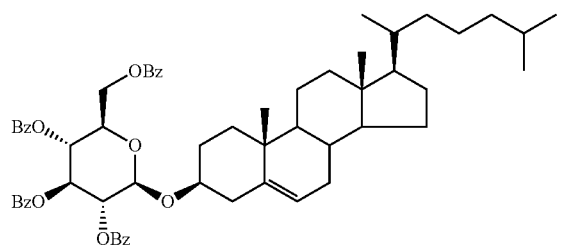

wherein Bz is benzoyl

Chemical Formula 7

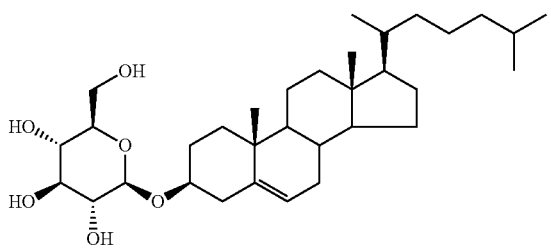

Chemical Formula 8

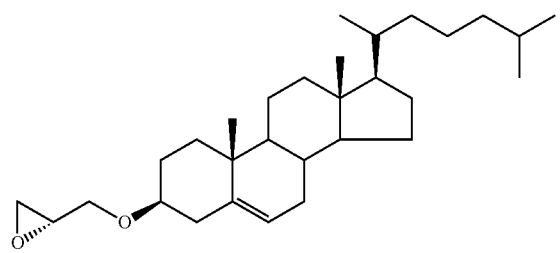

Chemical Formula 9

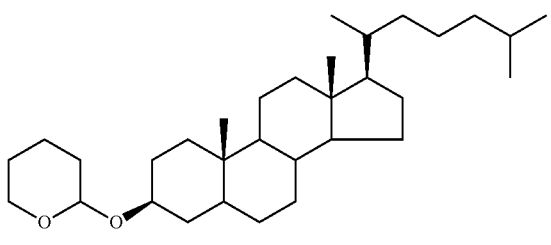

Chemical Formula 10

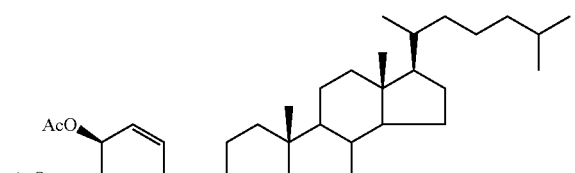

wherein Ac is acetyl

Chemical Formula 11

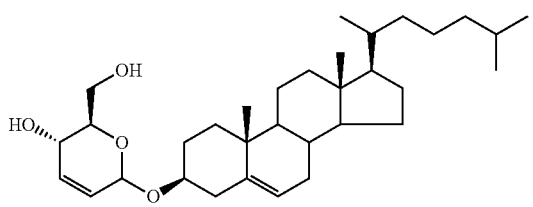

-continued
Chemical Formula 12
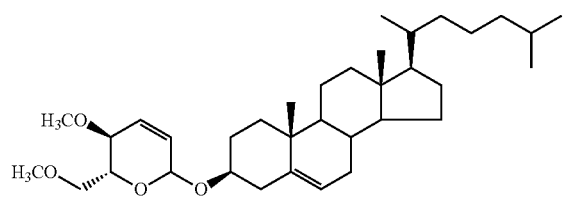
Chemical Formula 13
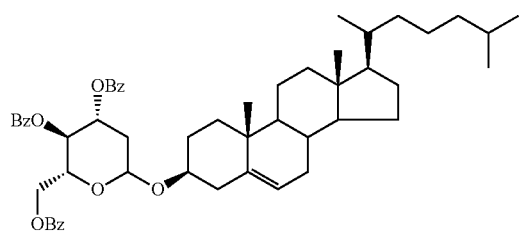
wherein Bz is benzoyl
Chemical Formula 14
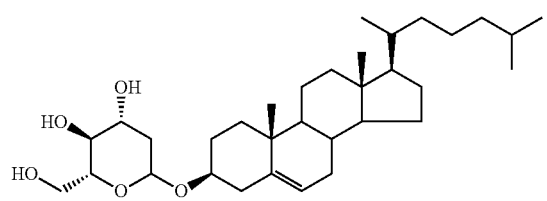
Chemical Formula 15
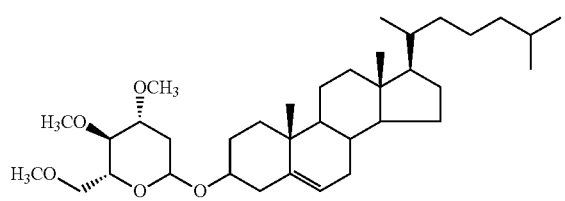
Chemical Formula 16
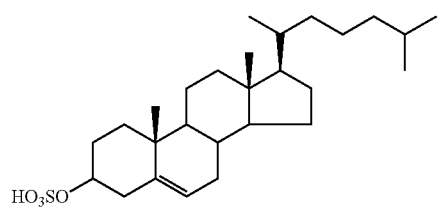
Chemical Formula 17
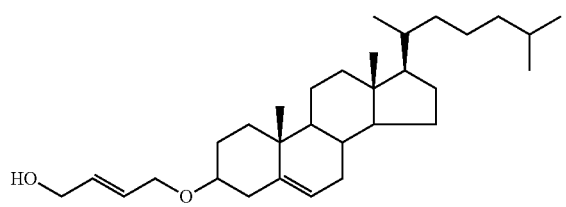
Chemical Formula 18
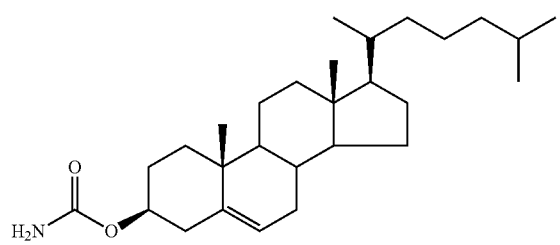
Chemical Formula 19
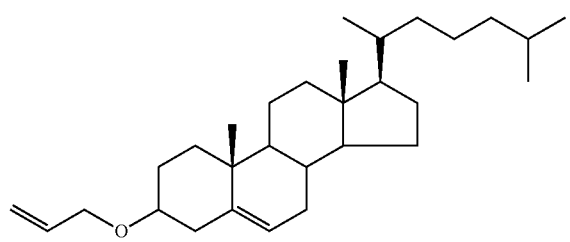
Chemiocal Formula 20
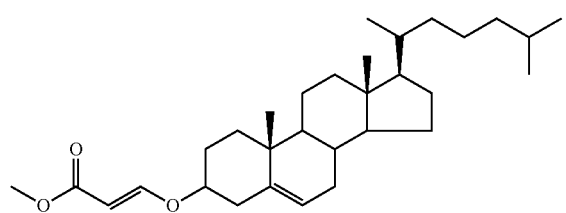
Chemical Formula 21
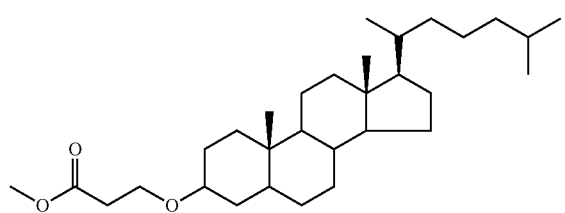
Chemical Formula 22
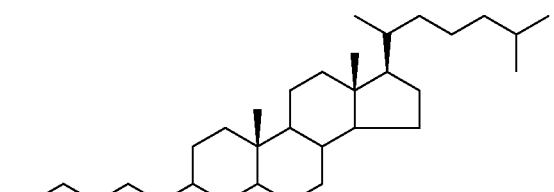
Chemical Formula 23
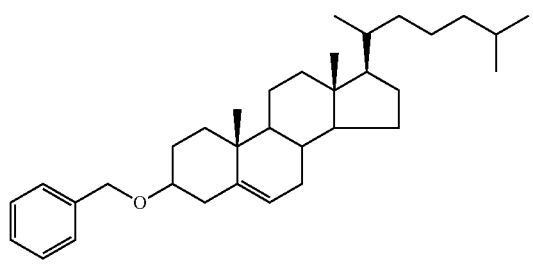

-continued
Chemical Formula 24
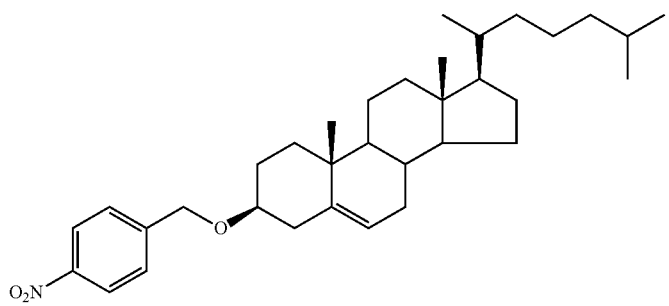
Chemical Formula 25
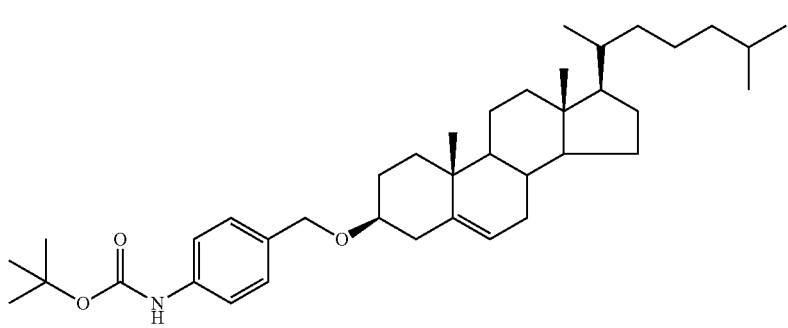
Chemical Formula 26
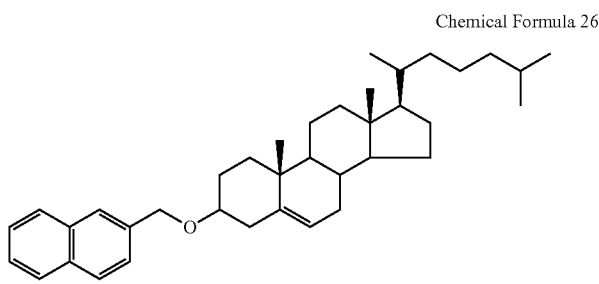
Chemical Formula 27
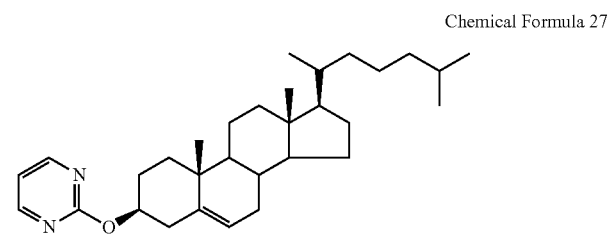
Chemical Formula 28
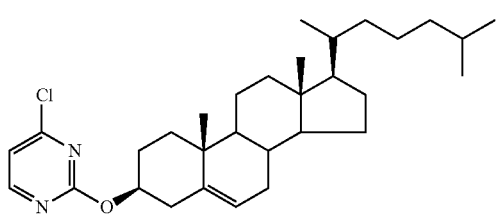
Chemical Formula 29
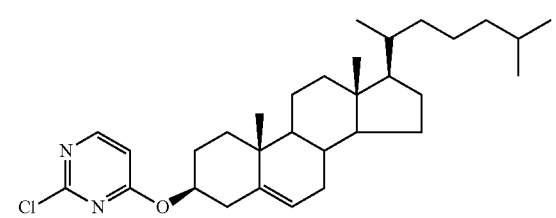
Chemical Formula 30
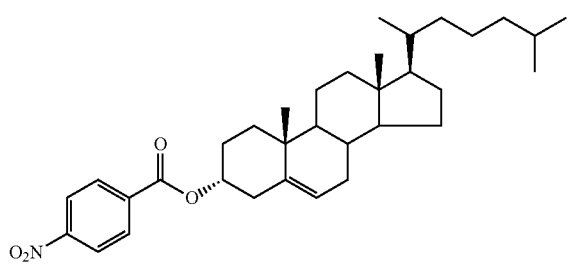
Chemical Formula 31
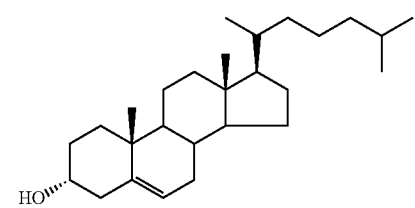

-continued
Chemical Formula 32
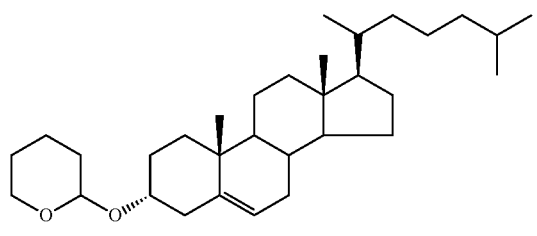
Chemical Formula 33
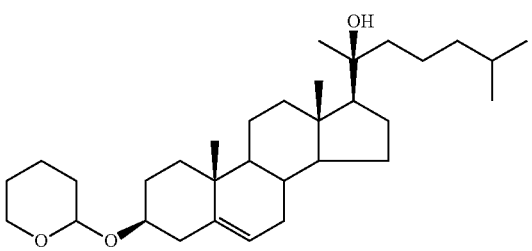
Chemical Formula 34
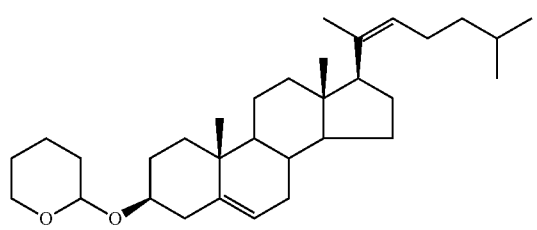
Chemical Formula 35
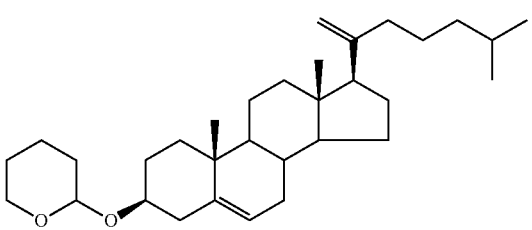
Chemical Formula 36
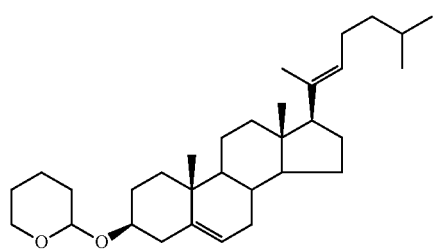
Chemical Formula 37
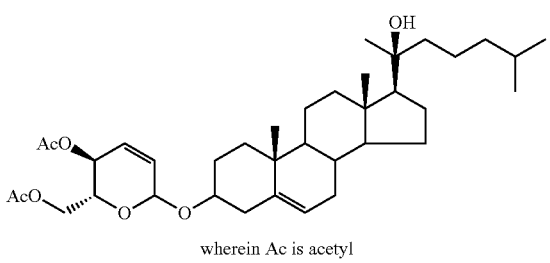
wherein Ac is acetyl
Chemical Formula 38
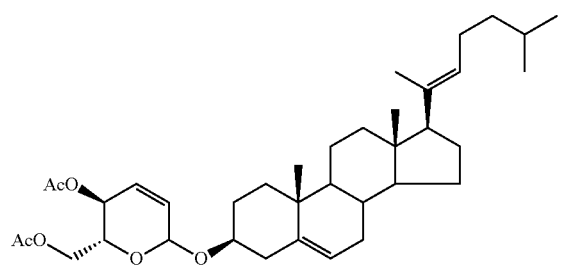
Chemical Formula 39
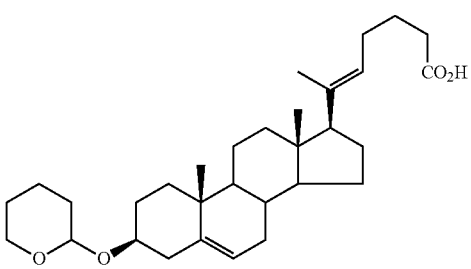
Chemical Formula 40
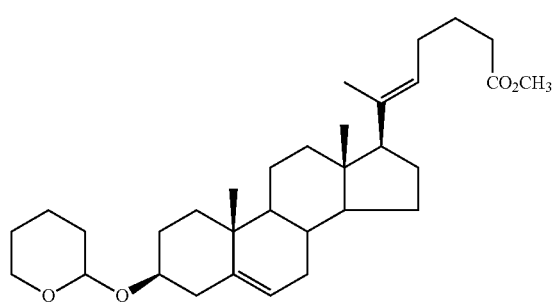
Chemical Formula 41
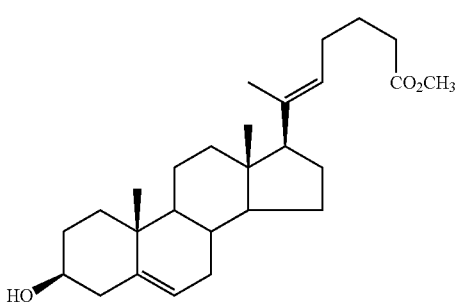

Chemical Formula 42

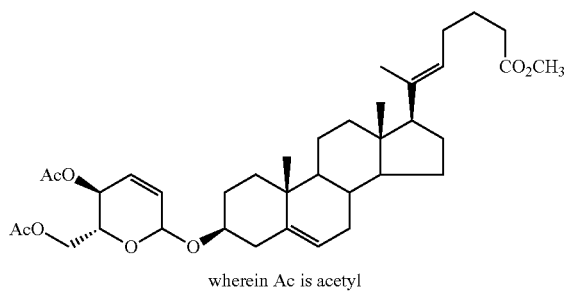

wherein Ac is acetyl

Chemical Formula 43

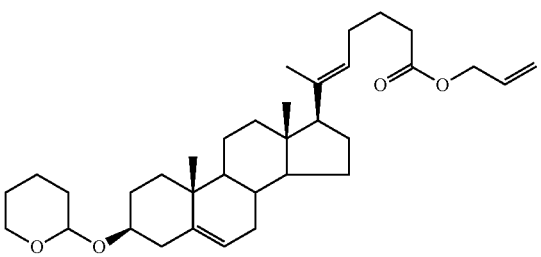

Chemical Formula 44

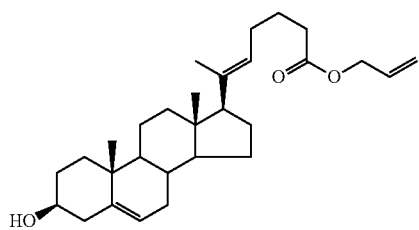

Chemical Formula 45

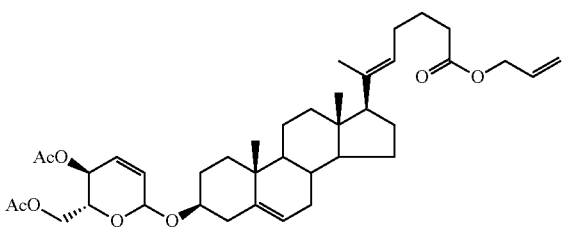

wherein Ac is acetyl

Chemical Formula 46

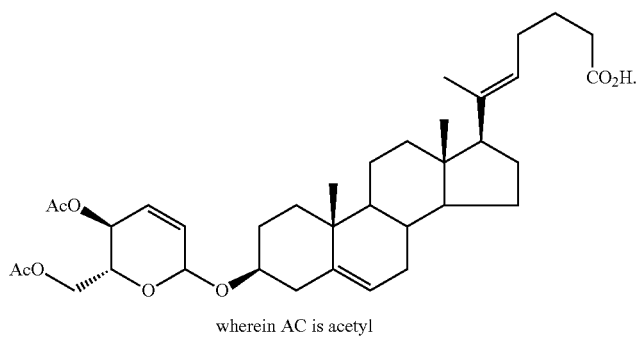

wherein AC is acetyl

The compounds of the present disclosure may have one or more chiral center and/or geometric isomeric center, and the present disclosure includes all stereoisomers, i.e., optical isomers, diastereoisomers and geometric isomers, of the compound represented by Chemical Formula 1.

The Rk1 or Rg3 analog of the present disclosure is very effective in preventing or treating vascular leakage. The diseases associated with vascular leakage that may be prevented or treated by the Rk1 or Rg3 analog of the present disclosure include diabetes, inflammation, retinopathy, diabetic retinopathy, macular degeneration, glaucoma, stricture, restricture, arteriosclerosis, atherosclerosis, cerebral edema, arthritis, arthropathy, uveitis, inflammatory bowel disease, macular edema, cancer, hyperlipidemia, ischemic disease, diabetic foot ulcer, pulmonary hypertension, acute lung injury, myocardial ischemia, heart failure, acute limb ischemia, myocardial infarction, stroke, ischemia, reperfusion injury, vascular leakage syndrome (VLS), edema, transplant rejection, burn, acute or adult respiratory distress syndrome (ARDS), sepsis or autoimmune disease.

For example, when the composition of the present disclosure is used for prevention or treatment of restructure, the composition of the present disclosure may be coated on a stent.

When the composition of the present disclosure is used for prevention or treatment of cancer, the composition of the present disclosure, it may be used either alone or in combination with other commonly used chemotherapies or radiation therapies. The combination therapy may be more effective in treating cancer. The chemotherapy agents that may be used together with the composition of the present disclosure include cisplatin, carboplatin, procarbazine, mechlorethamine, cyclophosphamide, ifosfamide, melphalan, chlorambucil, bisulfan, nitrosourea, actinomycin D, daunorubicin, doxorubicin, bleomycin, plicomycin, mitomycin, etoposide, tamoxifen, taxol, transplatinum, 5-fluorouracil, vincristine, vinblastine, methotrexate, etc. The radiation therapies that may be used together with the composition of the present disclosure include X-ray radiation, γ-ray radiation, etc.

The Rk1 or Rg3 analog of the present disclosure may be provided as a pharmaceutical composition, a food composition or a cosmetic composition.

When the composition of the present disclosure is prepared into a pharmaceutical composition, the pharmaceutical composition of the present disclosure comprises a pharmaceutically acceptable carrier. The pharmaceutically acceptable carrier included in the pharmaceutical composition of the present disclosure may be a commonly used one, including lactose, dextrose, sucrose, sorbitol, mannitol, starch, gum acacia, calcium phosphate, alginate, gelatin, calcium silicate, microcrystalline cellulose, polyvinylpyrrolidone, cellulose, water, syrup, methyl cellulose, methyl hydroxybenzoate, propyl hydroxybenzoate, talc, magnesium stearate, mineral oil, etc., but is not limited thereto. The pharmaceutical composition of the present disclosure may further include, in addition to the above-described components, a lubricant, a wetting agent, a sweetener, a fragrance, an emulsifier, a suspending agent, a preservative, or the like. Suitable pharmaceutically acceptable carriers and formulations are described in detail in *Remington's Pharmaceutical Sciences* (19th ed., 1995).

The pharmaceutical composition of the present disclosure may be administered orally or parenterally. When administered parenterally, it may be administered intravenously, subcutaneously, intramuscularly, intraabdominally, transdermally, or the like.

An appropriate administration dosage of the pharmaceutical composition of the present disclosure may be determined variously depending on such factors as preparation method, administration method, age, body weight and gender of a patient, pathological condition, diet, administration time, administration route, excretion rate or response sensitivity. Specifically, a daily dosage of the pharmaceutical composition of the present disclosure may be 0.001-100 mg/kg.

The pharmaceutical composition of the present disclosure may be prepared into a unit dosage form or multiple dosage form along with a pharmaceutically acceptable carrier and/or excipient according to a method that can be easily employed by those skilled in the art. The formulation may be in the form of solution in oily or aqueous medium, suspension, syrup, emulsion, extract, dust, powder, granule, tablet or capsule, and may further include a dispersant or stabilizer.

When the composition of the present disclosure is prepared as a food composition, the composition of the present disclosure may comprise ingredients commonly added for preparation of food. For example, flavor or natural carbohydrate may be added. The natural carbohydrate may be, for example, a monosaccharide (e.g. glucose, fructose, etc.), a disaccharide (e.g. maltose, sucrose, oligosaccharide, etc.), an oligosaccharide, a polysaccharide (e.g. dextrin, cyclodextrin, etc.) or a sugar alcohol (e.g. xylitol, sorbitol, erythritol, etc.). The flavor may be a natural flavor (e.g. thaumatin, stevia extract) or a synthetic flavor (e.g. saccharin, aspartame, etc.).

When the composition of the present disclosure is prepared as a cosmetic composition (in particular, a functional cosmetic composition), it may comprise ingredients commonly added for preparation of cosmetics.

The features and advantages of the present disclosure may be summarized as follows:

(a) The novel vascular leakage inhibitor of the present disclosure inhibits the apoptosis of vascular endothelial cells, inhibits the formation of actin stress fibers induced by VEGF, enhances the cortical actin ring structure, and improves the stability of the tight junctions (TJs) between vascular endothelial cells, thereby inhibiting vascular leakage.

(b) The vascular leakage inhibitor of the present disclosure has the activity of not only reducing vascular permeability but also recovering the integrity of damaged blood vessels.

(c) The vascular leakage inhibitor of the present disclosure can prevent or treat various diseases caused by vascular leakage.

(d) Since the vascular leakage inhibitor of the present disclosure is synthesized from commercially available or easily synthesizable cholesterols, it has remarkably superior feasibility of commercial synthesis.

BRIEF DESCRIPTION OF THE DRAWINGS

FIGS. 2*a*-2*d* show the result of observing cell morphologies. DM, Sac, 01, 02, 03 04, 05, 06, 07, 09, 10, 16, 19, 20, 21, 22 and R respectively denote DMSO, compound of Chemical Formula 23, Sac0601, Sac0602, Sac0603, Sac0504, Sac0505, Sac0902, Sac0507, Sac0509, Sac0510, Sac0516, Sac0519, Sac0520, Sac0521, Sac0522 and Rk1.

FIGS. 5*a*-5*c* show the result of observing cell morphologies.

Figure 1A:
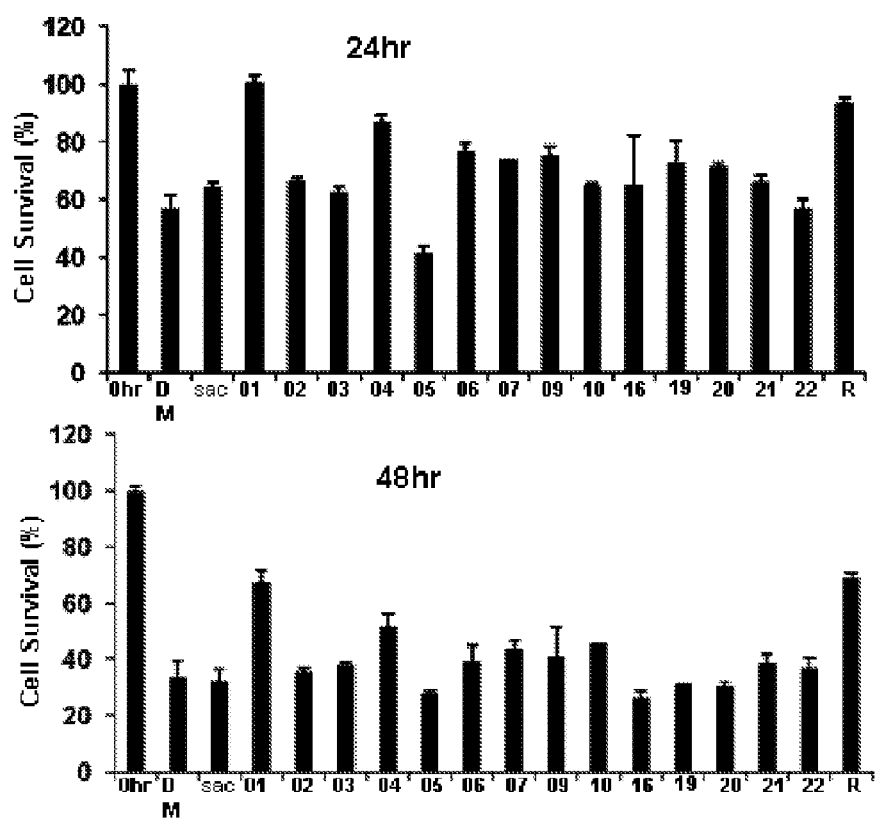
FIGS. 1*a*-1*b* and FIGS. 2*a*-2*d* show the result of screening Rk1 analogs that protect human umbilical vein endothelial cells (HUVECs) from serum depletion-induced apoptosis. HUVECs ($3 \times 10^5$ cells/well) were seeded on a 24-well plate in M199 medium containing 20% fetal bovine serum. The next day, the cells were transferred to a medium containing 5 μg/mL (FIG. 1*a*) or 10 μg/mL (FIG. 1*b*) of the synthesized compound. Cell viability was determined by MIT assay 24 hours and 48 hours later.

The present invention will now be described in further detail by examples. It would be obvious to those skilled in the art that these examples are intended to be more concretely illustrative and the scope of the present invention as set forth in the appended claims is not limited to or by the examples.

EXAMPLES

Synthesis Examples

Compounds with various pseudosugar bioisosteres introduced at the 3-OH group of cholesterol were designed and synthesized.

Synthesis Example 1

Synthesis of Rk1 Derivatives 1

Compounds with cyclic ether groups and ring-opened alkyl ether groups introduced as pseudosugar bioisosteres were designed and synthesized. In particular, various derivatives of tetrahydropyran, which is expected to be influential in biological activity, were synthesized.

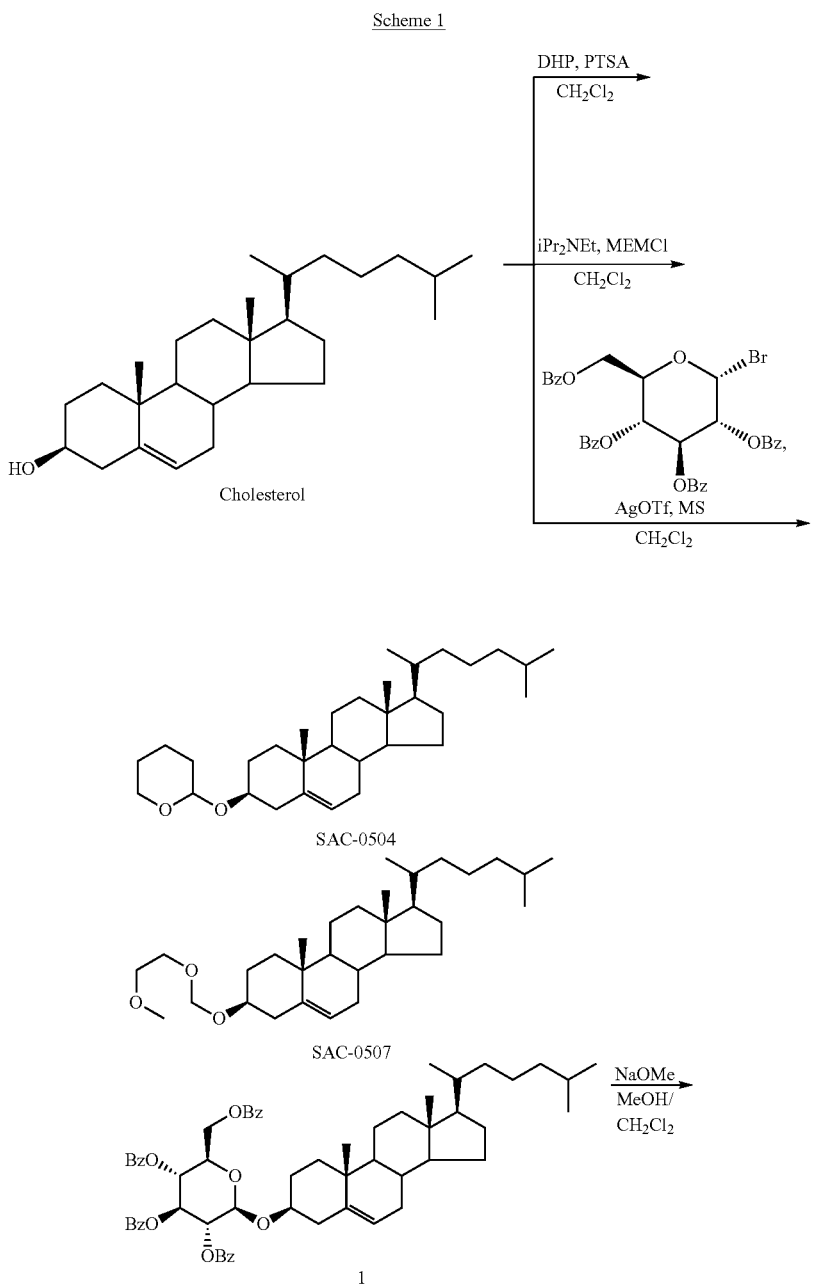

Scheme 1

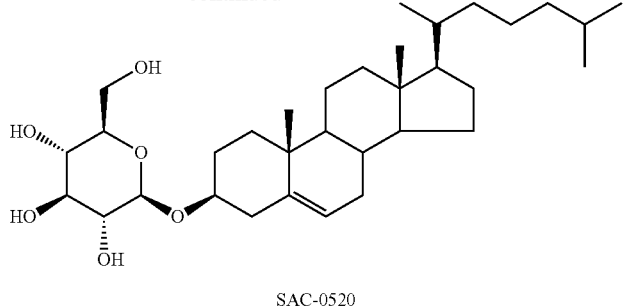

SAC-0520

Synthesis Example 1-1

Preparation of SAC-0504

Cholesterol (TCI, 100 mg) was dissolved in dichloromethane (5 After adding dihydropyran (Aldrich, 035 mL) and p-toluenesulfonic acid (TCI, 18 mg) under argon flow, the mixture was stirred at room temperature for 4 hours. The reaction mixture was diluted by adding ethyl acetate (30 mL), washed with water, dried with magnesium sulfate, and then filtered. The filtrate was concentrated under reduced pressure and the residue was subjected to silica gel column chromatography using ethyl acetate/hexane (1:25) as eluent to obtain the target compound SAC-0504 (39.5 mg, 32%): $^1$H-NMR (300 MHz, CDCl$_3$): 5.33 (t, 1H, J=4.8 Hz), 4.69 (m, 1H), 3.89 (m, 1H), 3.54-3.49 (m, 2H), 2.34-2.29 (m, 2H), 2.00-0.83 (m, 44H), 0.65 (s, 3H).

Synthesis Example 1-2

Preparation of SAC-0567

Cholesterol (97 mg) was dissolved in dichloromethane (1 mL). After adding diisopropylethylamine (Aldrich, 0.087 mL) and 2-methoxyethoxymethyl chloride (TCI, 0.3 mL) under argon flow, the mixture was stirred at room temperature for 1 hour. After stopping reaction by adding aqueous ammonium chloride solution, the reaction mixture was diluted by adding ethyl acetate (30 mL), washed with aqueous sodium bicarbonate solution, dried with magnesium sulfate, and then filtered. The filtrate was concentrated under reduced pressure and the residue was subjected to silica gel column chromatography using ethyl acetate/hexane (1:5) as eluent to obtain the target compound SAC-0507 (57 mg, 48%): $^1$H-NMR (300 MHz, CDCl$_3$): 5.33 (t, 1H, J=4.8 Hz), 4.76 (s, 2H), 3.70-3.67 (m, 2H), 3.55-3.52 (m, 2H), 3.43 (m, 1H), 3.37 (s, 3H), 2.36-2.19 (m, 2H), 2.00-0.83 (m, 38H), 0.64 (s, 3H).

Synthesis Example 1-3

Preparation of SAC-0520

2,3,4,6-Tetra-O-benzoyl-α-D-glucopyranosyl bromide (Tetrahedron Lett. 31, 7441-7444 (1990), 244 mg) and cholesterol (150 mg) were dissolved in dichloromethane (5 mL) under nitrogen flow and stirred at −20° C. for 2 hours. After filtering, the reaction mixture was washed with aqueous sodium bicarbonate solution and aqueous sodium chloride solution, dried with magnesium sulfate, and then filtered. The residue was subjected to silica gel column chromatography using ethyl acetate/hexane (1:10) as eluent to obtain the target compound 1 (140 mg, 45%). After dissolving sodium in methanol/dichloromethane (1:1, 2.4 mL), the compound 1 obtained above was added under argon flow and stirred at room temperature for 30 minutes. After stopping reaction by adding aqueous ammonium chloride solution, the reaction mixture was diluted by adding dichloromethane (30 mL), washed with aqueous sodium chloride solution, dried with magnesium sulfate, and then filtered. The filtrate was concentrated under reduced pressure and the residue was subjected to silica gel column chromatography using ethyl acetate/hexane/methanol (4:5:1) as eluent to obtain the target compound SAC-0520: $^1$H-NMR (300 MHz, pyridine-d$^5$): 5.33 (t, 1H, J=4.8 Hz), 5.06 (d, 1H, J=7.7 Hz), 4.57 (d, 1H, J=9.5 Hz), 4.42 (dd, 1H, J=4.9, 11.7 Hz), 4.31-4.28 (m, 2H), 4.09-3.91 (m, 3H), 2.72 (d, 1H, J=13 Hz), 2.47 (t, 1H, J=11.5 Hz), 2.10-0.88 (m, 42H), 0.64 (s, 3H).

Scheme 2

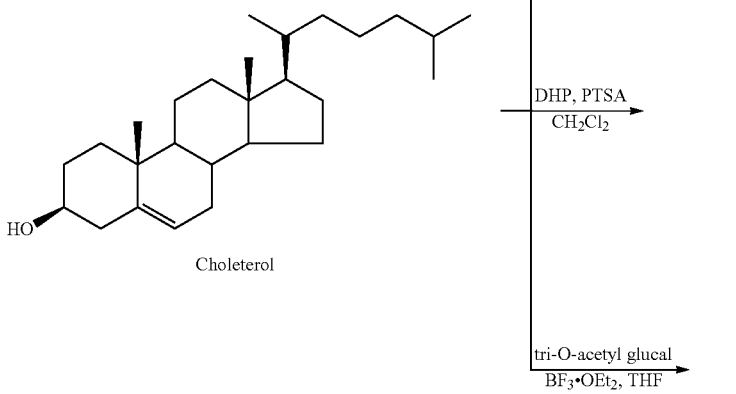

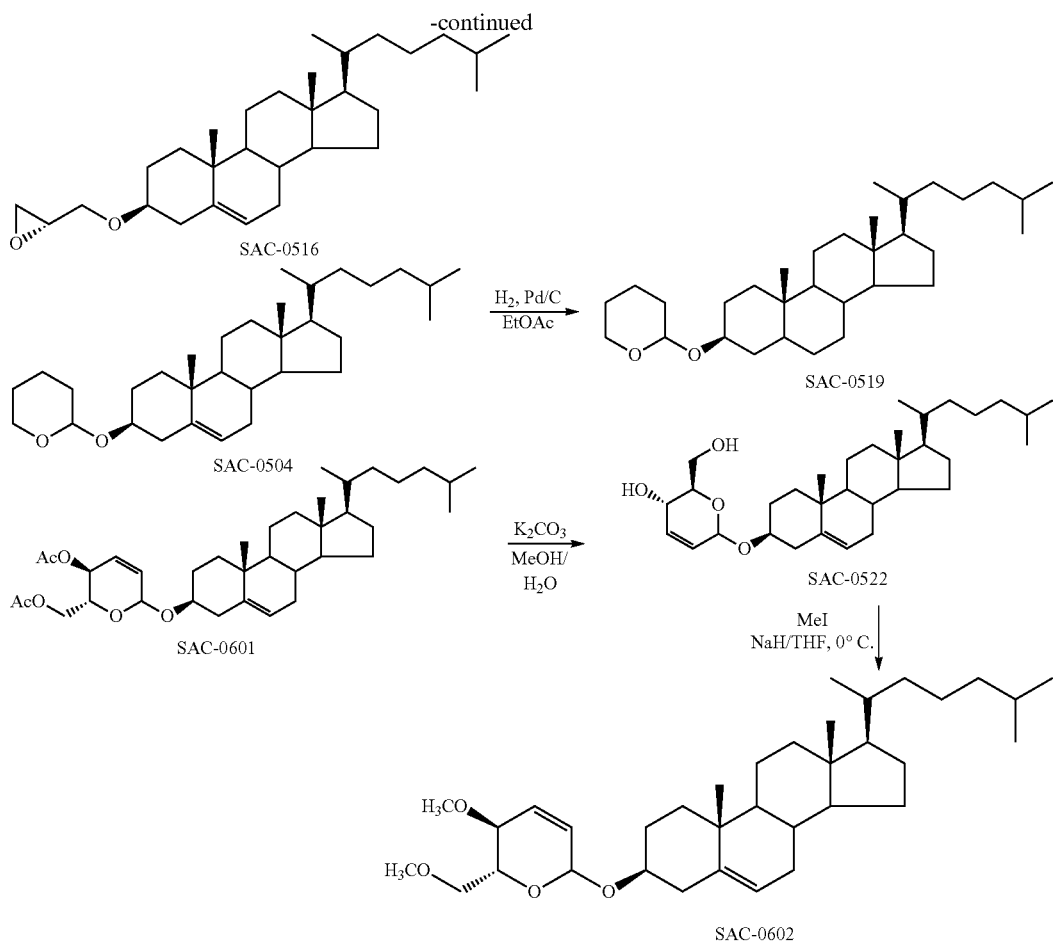

Synthesis Example 1-4

Preparation of SAC-05.16

Sodium hydride (Aldrich (42 mg) was dissolved in dimethylformamide/tetrahydrofuran (5 mL). After adding cholesterol (200 mg) under argon flow, the mixture was stirred at room temperature for 30 minutes. After slowly adding glycidyl tosylate (Aldrich, 294 mg) dissolved in dimethylformamide/tetrahydrofuran, the reaction mixture was stirred at room temperature for a day. After stopping reaction by adding aqueous ammonium chloride solution, the reaction mixture was diluted by adding diethyl ether (30 mL), washed with 10% aqueous sodium hydroxide solution and aqueous sodium chloride solution, dried with magnesium sulfate, and then filtered. The filtrate was concentrated under reduced pressure and the residue was subjected to silica gel column chromatography using ethyl acetate/hexane (1:10) as eluent to obtain the target compound SAC-0516 (72 mg, 31%): $^1$H-NMR (300 MHz, CDCl$_3$): 5.33 (t, 1H, J=4.8 Hz), 3.70 (dd, 1H, J=3.3, 11.4 Hz), 3.45 (dd, 1H, J=5.7, 11.3 Hz), 3.25-3.09 (m, 2H), 2.78 (t, 1H, J=4.6 Hz), 2.59 (dd, 1H, J=2.76, 4.95 Hz), 2.40-2.10 (m, 2H), 2.02-1.66 (m, 5H), 2.00-0.83 (m, 33H), 0.64 (5, 3H).

Synthesis Example 1-4

Preparation of SAC-0519

SAC-0504 (40 mg) prepared in Synthesis Example 1-1 was dissolved in ethyl acetate (3 mL). After adding catalytic amount of 10% palladium/activated carbon and substituting with hydrogen, the reaction mixture was stirred at room temperature for 30 minutes. After diluting with ethyl acetate and filtering using Celite, the filtrate was concentrated under reduced pressure and the residue was subjected to silica gel column chromatography using ethyl acetate/hexane (1:20) as eluent to obtain the target compound SAC-051.9: $^1$H-NMR (300 MHz, CDCl$_3$): 4.69 (m, 1H), 3.89 (m, 1H), 3.61-3.42 (m, 2H), 2.00-0.83 (m, 48H), 0.65 (s, 3H), 0.59 (m, 1H).

Synthesis Example 1-5

Preparation of SAC-0601

Cholesterol (1 g) was dissolved in diethyl ether (20 mL). After adding tri-O-acetyl-D-glucal (Aldrich, 2.04 g) and boron trifluoride diethyl etherate (Aldrich, 1.27 mL) under argon flow, the reaction mixture was stirred at 0° C. for 3 hours. The reaction mixture was diluted by adding diethyl ether (30 mL), washed with aqueous sodium bicarbonate solution, dried with sodium sulfate, and then filtered. The filtrate was concentrated under reduced pressure and the residue was subjected to silica gel column chromatography using ethyl acetate/hexane (1:5) as eluent to obtain the target compound SAC-0601 (643 mg, 43%): $^1$H-NMR (300 MHz, CDCl$_3$): 5.87-5.77 (m, 2H), 5.33 (m, 1H), 5.26 (dd, 1H, J=1.47, 9.15 Hz), 5.15 (m, 1H), 4.25-4.06 (m, 3H), 3.54 (m, 1H), 2.42-2.27 (m, 2H), 2.07 (s, 3H), 2.05 (s, 3H), 2.02-0.83 (m, 38H), 0.65 (s, 3H).

Synthesis Example 1-6

Preparation of SAC-0522

SAC-0601 (350 mg) prepared in Synthesis Example 1-5 and potassium carbonate (322 mg) were dissolved in methanol/water (2:1, 15 mL) and stirred at 0° C. for 2 days. The reaction mixture was diluted by adding dichloromethane (70 mL), washed with water and aqueous sodium chloride solution, dried with magnesium sulfate, and then filtered. The filtrate was concentrated under reduced pressure and the residue was subjected to silica gel column chromatography using ethyl acetate/hexane/methanol (20:40:3) as eluent to obtain the target compound SAC-0522 (585 mg, 78%): $^1$H-NMR (400 MHz, CDCl$_3$): 5.96 (d, 1H, J=10.2 Hz), 5.75 (td, 1H, J=2.23, 10.2 Hz), 5.36 (d, 1H, J=6.7 Hz), 5.13 (bs, 1H), 4.21 (bs, 1H), 3.92-3.80 (m, 2H), 3.76 (m, 1H), 3.54 (m, 1H), 2.42-2.27 (m, 2H), 2.02-0.83 (m, 40H), 0.65 (s, 3H).

Synthesis Example 1-7

Preparation of SAC-0602

Sodium hydride (34 mg) was dissolved in tetrahydrofuran (4 mL). After adding SAC-0522 (87 mg) prepared in Synthesis Example 1-5 under argon flow, the mixture was stirred at 0° C. for 1 hour. After slowly adding iodomethane (Aldrich, 0.1 mL), the reaction mixture was stirred at room temperature for a day. The reaction mixture was diluted by adding ethyl acetate (20 mL), washed with aqueous sodium chloride solution, dried with sodium sulfate, and then filtered. The filtrate was concentrated under reduced pressure and the residue was subjected to silica gel column chromatography using ethyl acetate/hexane (110) as eluent to obtain the target compound SAC-0602 (30 mg, 32%): $^1$H-NMR (300 MHz, CDCl$_3$): 6.04 (d, 1H, J=10.2 Hz), 5.72 (d, 1H, J=11.2 Hz), 5.32 (d, 1H, J=5.1 Hz), 5.12 (d, 1H, J=2.6 Hz), 2.42-2.29 (m, 2H), 2.02-1.69 (m, 5H), 1.59-0.76 (m, 44H), 0.65 (s, 3H),

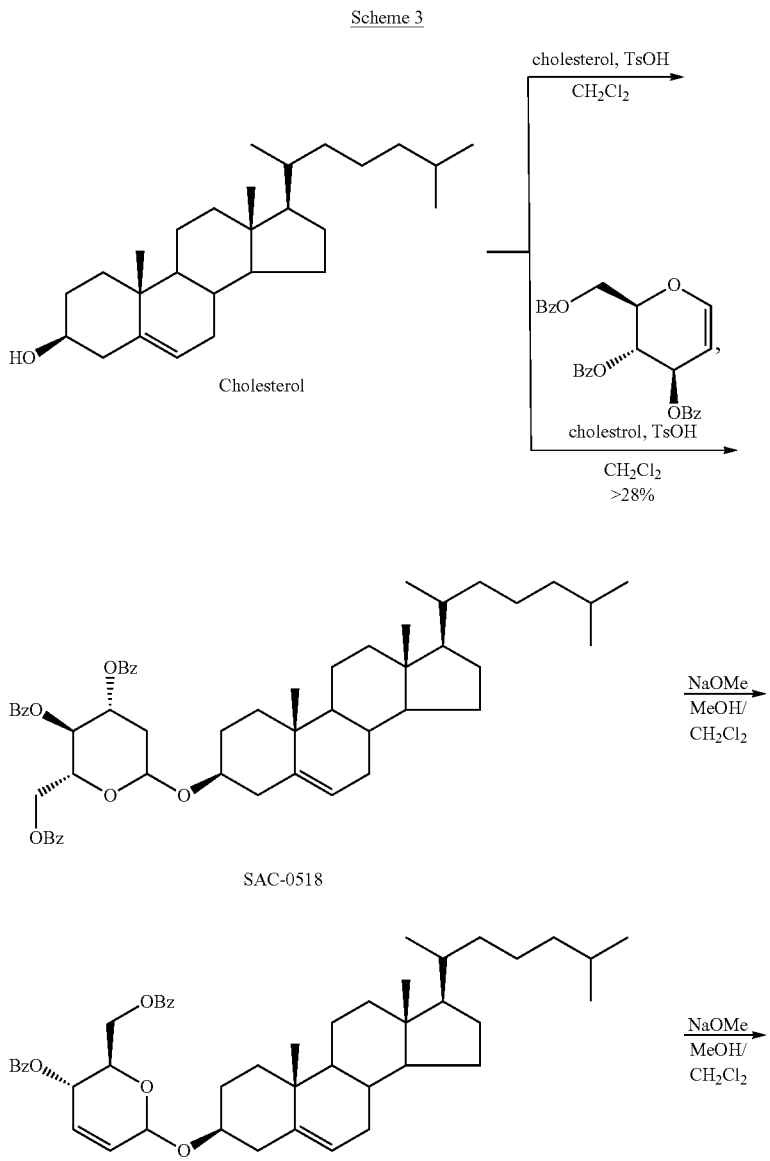

Scheme 3

-continued

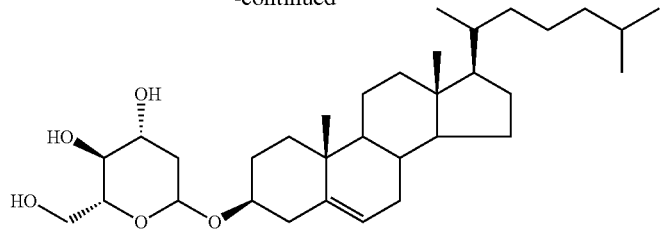

SAC-0521

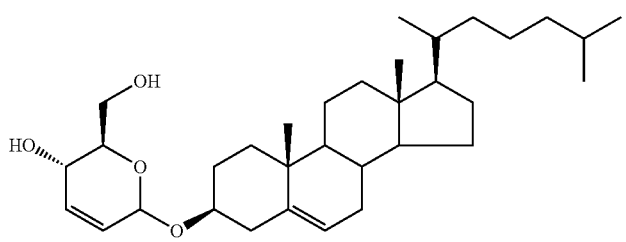

SAC-0522

Synthesis Example 1-8

Preparation of SAC-0518

Cholesterol (108 mg) was dissolved in dichloromethane (10 mL). After adding tri-O-acetyl-D-glucal (Aldrich, 320 mg) and p-toluenesulfonic acid (TCI, 11 mg) under argon flow, the mixture was stirred at room temperature for 2 hours. The reaction mixture was diluted by adding ethyl acetate (30 mL), washed with water and aqueous sodium chloride solution, dried with magnesium sulfate, and then filtered. The filtrate was concentrated under reduced pressure and the residue was subjected to silica gel column chromatography using ethyl acetate/hexane (1:25) as eluent to obtain the target compound SAC-0518 (60 mg, 26%): α isomer $^1$H-NMR (300 MHz, CDCl$_3$): 8.03-7.90 (m, 6H), 7, 52-7.45 (m, 3H), 7.40-7.33 (m, 6H), 5.74 (m, 1H), 5.48 (m, 1H), 5.30 (m, 1H), 5.20 (m, 1H), 4.53-4.41 (m, 3H), 3.54 (m, 1H), 2.40-0.84 (m, 42H), 0.65 (s, 3H); 13 isomer: $^1$H-NMR (300 MHz, CDCl$_3$): 8.03-7.90 (m, 6H), 7.52-7.45 (m, 3H), 7.40-7.33 (m, 6H), 5.49-5.32 (m, 2H), 5.20 (m, 1H), 4.86 (m, 1H), 4.53-4.41 (m, 2H), 3.98 (m, 1H), 3.54 (m, 1H), 2.40-0.84 (m, 42H), 0.65 (s, 3H).

Synthesis Example 1-9

Preparation of SAC-021

Sodium was dissolved in methanol/dichloromethane (1:1, 6 mL). After adding SAC-051.8 (57 mg) prepared in Synthesis Example 1-8 under argon flow, the mixture was stirred at room temperature for 1 hour and 20 minutes. After stopping reaction by adding aqueous ammonium chloride solution, the reaction mixture was diluted by adding diethyl ether (30 washed with aqueous sodium chloride solution, dried with magnesium sulfate, and then filtered. The filtrate was concentrated under reduced pressure and the residue was subjected to silica gel column chromatography using ethyl acetate/hexane/methanol (40:20:1) as eluent to obtain the target compound SAC-0521 (30 mg, 84%): α isomer: $^1$H-NMR (500 MHz, CDCl$_3$): 5.32 (m, 1H), 5.02 (d, 1H, J=2.1 Hz), 3.99 (m, 1H), 3.85-3.82 (m, 2H), 3.67 (d, 1H, J=8.95 Hz), 3.55-3.40 (m, 2H), 2.26-0.84 (m, 45H), 0.65 (s, 3H); β isomer: $^1$H-NMR (500 MHz, CDCl$_3$): 5.32 (m, 1H), 4.68 (d, 1H, J=9.3 Hz), 3.85-3.82 (m, 2H), 3.67 (d, 1H, J=8.95 Hz), 3.55-3.40 (m, 2H), 3.26 (m, 1H), 2.26-0.84 (m, 45H), 0.65 (s, 3H).

Scheme 4

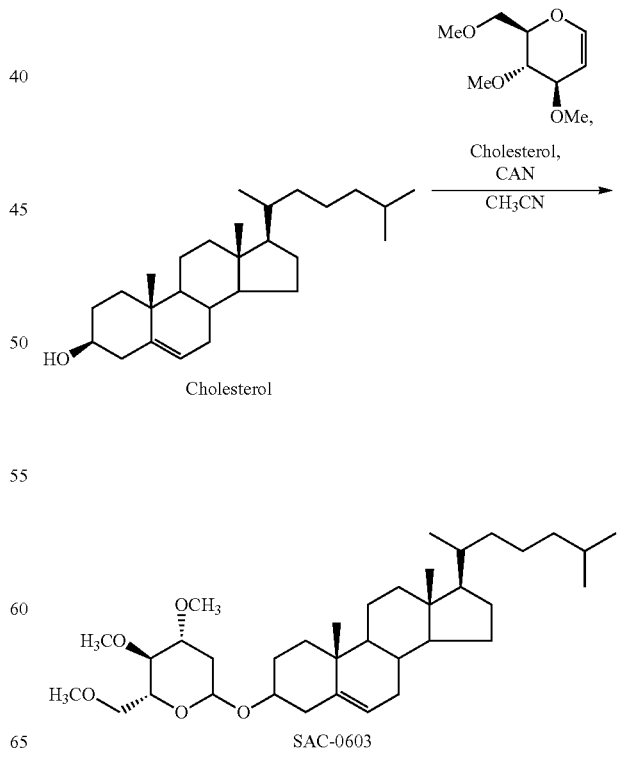

Synthesis Example 1-10

Preparation of SAC-0603

Cholesterol (592 mg) was dissolved in anhydrous acetonitrile (6 mL). After adding tri-O-methyl-D-glucal (Aldrich, 288 mg) and catalytic amount of ceric ammonium nitrate (Aldrich) under argon flow, the mixture was stirred at room temperature for 2 days. The reaction mixture was diluted by adding diethyl ether (50 mL), washed with aqueous sodium bicarbonate solution and aqueous sodium chloride solution, dried with magnesium sulfate, and then filtered. The filtrate was concentrated under reduced pressure and the residue was subjected to silica gel column chromatography using ethyl acetate/hexane (1:25) as eluent to obtain the target compound SAC-0603 (1.9 mg, 2%): $^1$H-NMR (300 MHz, CDCl$_3$): 5.28 (m, 2H), 5.06 (m, 1H), 3.70-3.50 (m, 5H), 3.52 (s, 3H), 3.43 (s, 3H), 3.39 (s, 3H), 3.17 (t, 1H, J=9.0 Hz) 2.26-0.84 (m, 41H), 0.65 (s, 3H).

Synthesis Example 2

Synthesis of Rk1 Derivatives 2

Compounds with various functional groups capable of replacing the OH group introduced as pseudosugar bioisosteres were designed and synthesized.

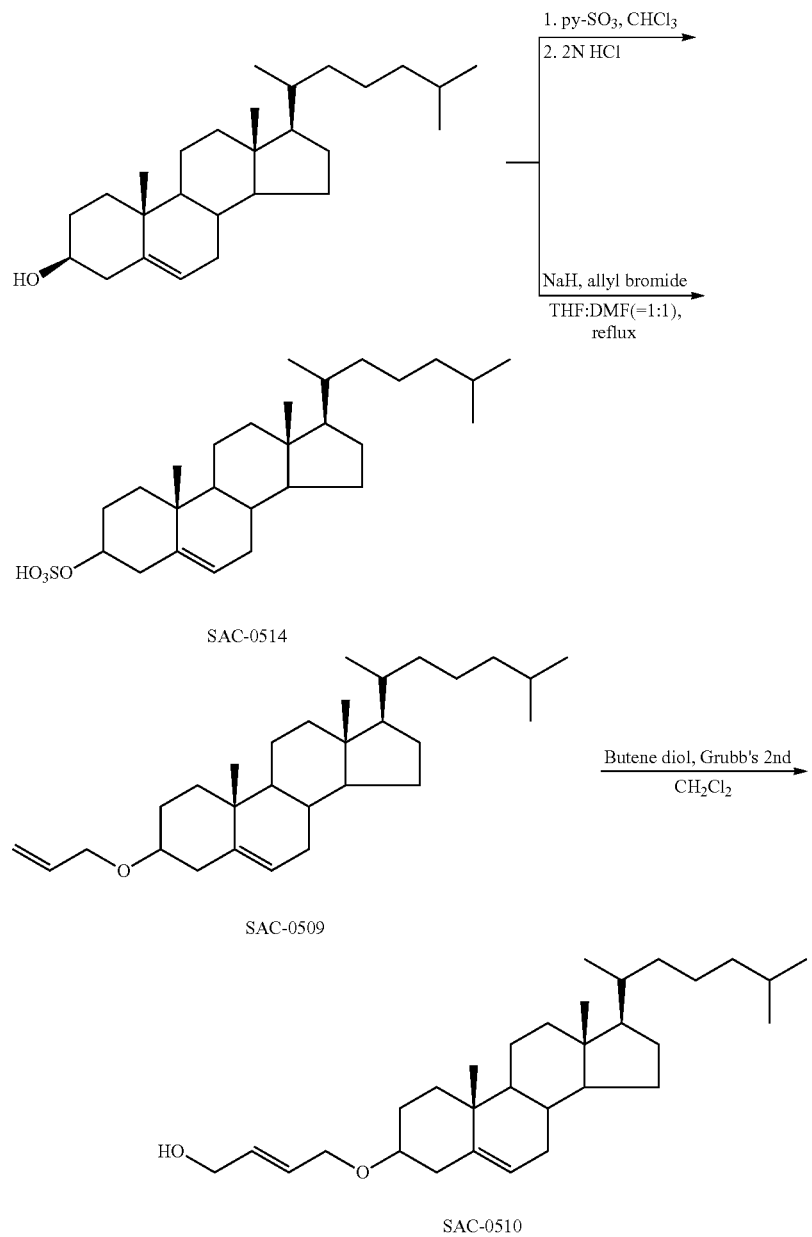

Scheme 5

Synthesis Example 2-1

Preparation of SAC-0514

Cholesterol (70 mg) was dissolved in chloroform (2 mL). After adding sulfur trioxide pyridine complex (Aldrich, 86 mg) under argon flow, the mixture was stirred at room temperature for a day. After acidifying with 2 N hydrochloric acid solution, the reaction mixture was diluted by adding ethyl acetate (20 mL), washed with water, dried with magnesium sulfate, and then filtered. The filtrate was concentrated under reduced pressure and the residue was subjected to silica gel column chromatography using dichloromethane/methanol (7:1) as eluent to obtain the target compound SAC-0514: $^1$H-NMR (300 MHz, CDCl$_3$): 5.28 (m, 2H), 5.06 (m, 1H), 3.70-3.50 (m, 5H), 3.52 (s, 3H), 3.43 (s, 3H), 3.39 (s, 3H), 3.17 (t, 1H, J=9.0 Hz) 2.26-0.84 (m, 41H), 0.65 (s, 3H).

Synthesis Example 2-2

Preparation of SAC-0510

SAC-0509 prepared in Synthesis Example 2-4 as will be described below was dissolved in dichloromethane (1 mL). After adding catalytic amount of Grubbs' 2nd catalyst (Aldrich) under argon flow and then adding excess butenediol, the mixture was stirred at room temperature for 1 hour. The reaction mixture was concentrated under reduced pressure and the residue was subjected to silica gel column chromatography using ethyl acetate/hexane (1:5) as eluent to obtain the target compound SAC-0510 (12 mg, 30%): $^1$H NMR (300 MHz, CDCl$_3$): 5.93-5.76 (m, 2H), 5.33 (d, 1H, J=5.1 Hz), 4.1.4 (d, 2H, J=4.7 Hz), 4.01 (d, 2H, J=5.13), 3.19 (m, 1H), 2.33 (m, 1H), 2.20 (m, 1H), 2.03-1.74 (m, 5H), 1.54-0.84 (m, 34H), 0.65 (s, 3H).

Scheme 6

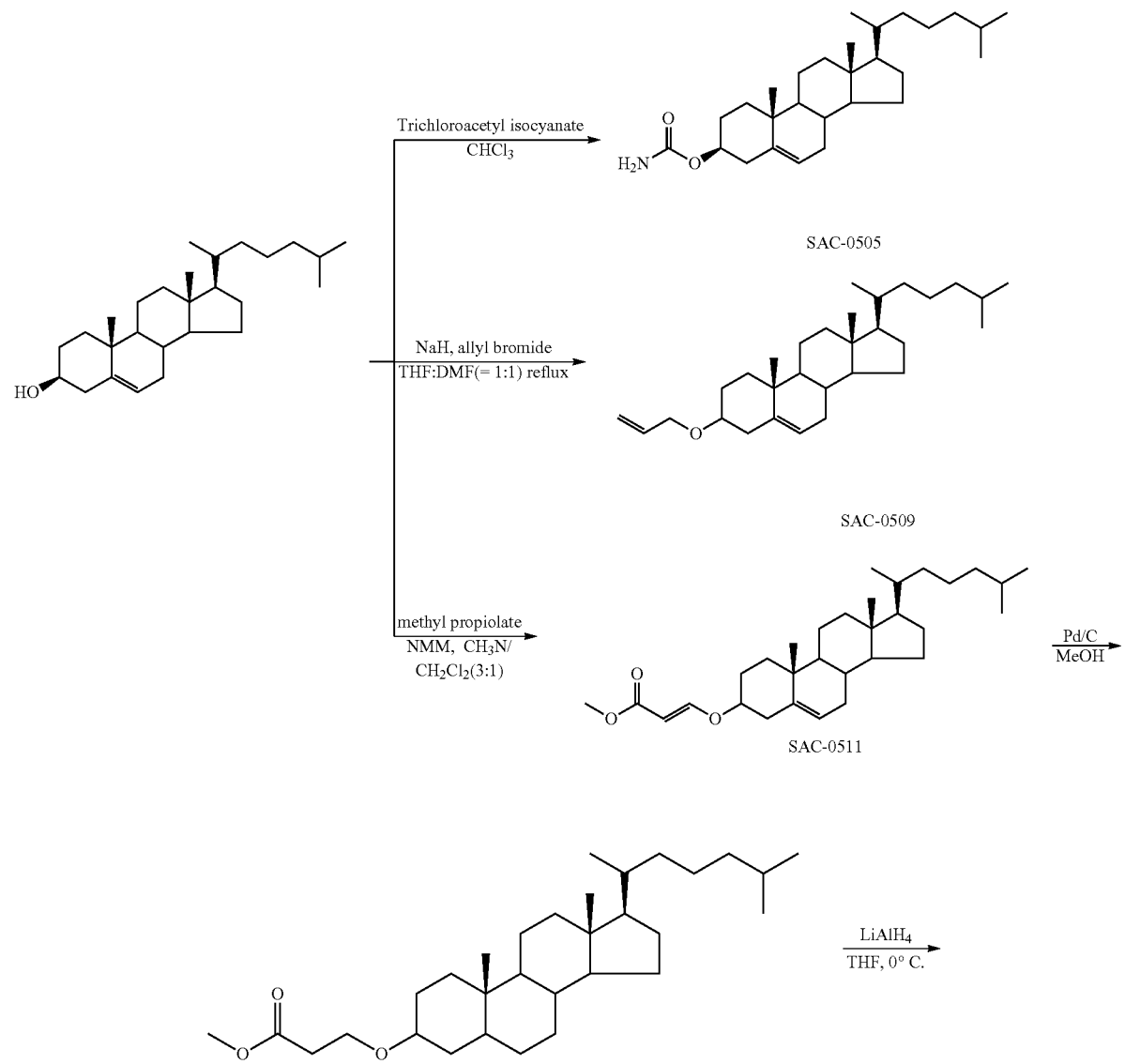

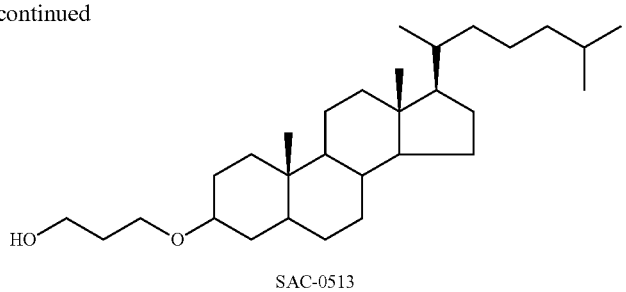

SAC-0513

Synthesis Example 2-3

Preparation of SAC-0505

Cholesterol (20 mg) was dissolved in chloroform (1 mL). After adding trichloroacetyl isocyanate (Aldrich, 0.04 mL) under argon flow, the mixture was stirred at room temperature for 2 hours. The reaction mixture was filtered using aluminum oxide and the filtrate was concentrated under reduced pressure to obtain the target compound SAC-0505: $^1$H-NMR (300 MHz, CDCl$_3$): 527 (m, 1H), 4.45-4.39 (m, 3H), 2.29-2.22 (m, 2H), 1.98-1.77 (m, 5H), 1.55-0.78 (m, 33H), 0.61 (s, 3H).

Synthesis Example 2-4

Preparation of SAC-0509

Sodium hydride (4:1 mg) was dissolved in dimethylformamide/tetrahydrofuran (3 mL). After adding cholesterol (200 mg) under argon flow, the mixture was stirred at room temperature for 1 hour. After slowly adding allyl bromide (Aldrich, 0.44 mL), the reaction mixture was stirred at room temperature for a day. Then, the reaction mixture was diluted by adding ethyl acetate (30 mL), washed with water, dried with magnesium sulfate, and then filtered. The filtrate was concentrated under reduced pressure and the residue was subjected to silica gel column chromatography using ethyl acetate/hexane (1:20) as eluent to obtain the target compound SAC-0509 (80 mg, 36%): $^1$H-NMR (300 MHz, CDCl$_3$): 5.90 (m, 1H), 5.36-5.11 (m, 3H), 4.00 (td, 2H, J=1.26, 5.7 Hz), 2.38-2.16 (m, 2H), 2.02-0.81 (m, 39H), 0.61 (s, 3H).

Synthesis Example 2-5

Preparation of SAC-0511

Cholesterol (100 mg) was dissolved in acetonitrile/dichloromethane (3:1, 2 mL). After slowly adding 4-methylmorpholine (Alfa Aesar, 0.12 mL) under argon flow, the mixture was stirred at room temperature for 30 minutes. Then, after slowly adding methyl propiolate (0.1 mL), the mixture was stirred at room temperature for 2 hours. The reaction mixture was concentrated under reduced pressure and the residue was subjected to silica gel column chromatography using ethyl acetate/hexane (1:10) as eluent to obtain the target compound SAC-0511 (75 mg, 64%): $^1$H-NMR (300 MHz, CDCl$_3$): 7.53 (d, 1H, J=12.5 Hz), 5.37 (d, 1H, J=5.0 Hz) 5.24 (d, 1H, J=12.5 Hz), 3.76 (m, 1H), 3.67 (s, 3H), 2.37-2.35 (m, 2H), 2.22-0.81 (m, 38H), 0.61 (s, 3H).

Synthesis Example 2-6

Preparation of SAC-0513

SAC-0511 prepared in Synthesis Example 2-5 was dissolved in methanol (1 mL). After adding catalytic amount of 10% palladium/activated carbon and substituting with hydrogen, the mixture was stirred at room temperature for 2 hours. After diluting with ethyl acetate and filtering using Celite, the filtrate was concentrated under reduced pressure and the residue was subjected to silica gel column chromatography using ethyl acetate/hexane (1:10) as eluent to obtain the target compound 2. The prepared target compound 2 was dissolved in tetrahydrofuran (0.5 mL) and 1 M lithium aluminum hydride (Aldrich) solution (0.1 mL) dissolved in tetrahydrofuran was slowly added under argon flow. After stirring at 0° C. for 5 minutes and adding water, methanol and ethyl acetate, the mixture was further stirred for 3 hours. The reaction mixture was washed with aqueous sodium chloride solution, dried with magnesium sulfate (and then filtered. The filtrate was concentrated under reduced pressure to obtain the target compound SAC-0513 (27 mg, 61%): $^1$H-NMR (300 MHz, CDCl$_3$): 3.75 (t, 2H, J=5.4 Hz), 3.65 (m, 2H), 3.21 (m, 1H), 2.20 (bs, 1H), 1.95-0.76 (m, 43H), 0.61 (s, 3H).

Synthesis Example 3

Synthesis of Rk1 derivatives 3

Compounds with various aryl functional groups capable of replacing the OH group introduced as pseudosugar bioisosteres were designed and synthesized.

Scheme 7
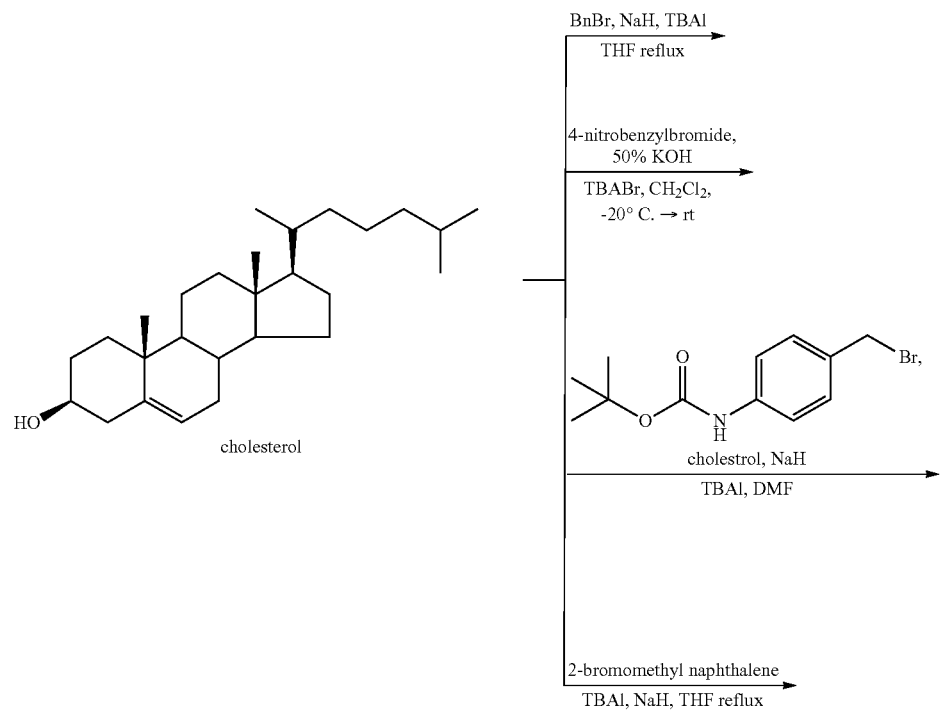
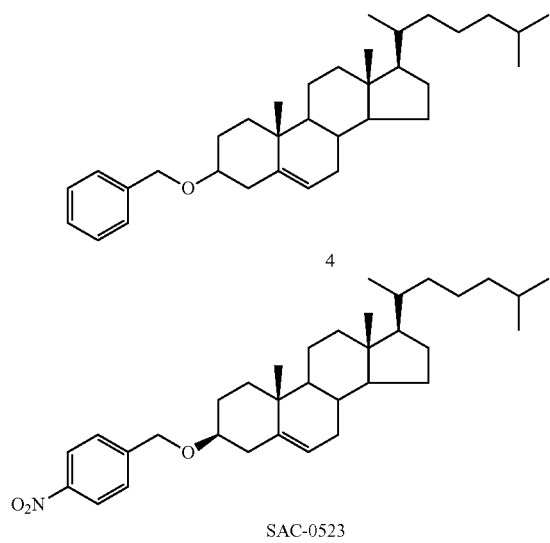
SAC-0523

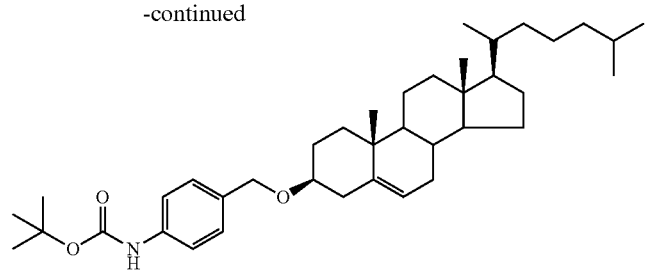

SAC-0605

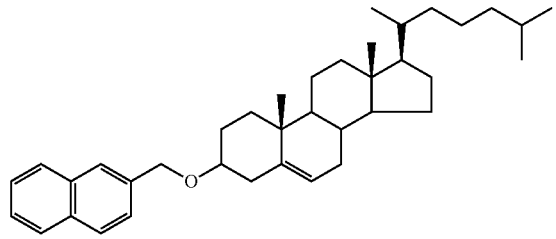

SAC-0902

Synthesis Example 3-1

Preparation of SAC-0523

Cholesterol (400 mg) was dissolved in dichloromethane (10 mL). After lowering temperature to −20° C. and adding tetrabutylammonium bromide (Aldrich, 120 mg), 4-nitrobenzyl bromide (Aldrich, 860 mg) and 50% aqueous potassium hydroxide solution (10 mL), the mixture was stirred at room temperature for 3 days. The reaction mixture was diluted by adding dichloromethane (60 mL), washed with water, dried with magnesium sulfate, and then filtered. The filtrate was concentrated under reduced pressure and the residue was subjected to silica gel column chromatography using ethyl acetate/hexane (1:10) as eluent to obtain the target compound SAC-0523 (24 mg, 6%): $^1$H-NMR (300 MHz, CDCl$_3$): 8.18 (d, 2H, J=8.8 Hz), 7.49 (d, 2H, J=8.8 Hz), 5.34 (m, 1H), 4.64 (s, 2H), 3.27 (m, 1H), 2.43-2.24 (m, 2H), 2.03-1.75 (m, 5H), 1.54-0.81 (m, 33H), 0.66 (s, 3H).

Synthesis Example 3-2

Preparation of SAC-0605

Sodium hydride (149 mg) was dissolved in tetrahydrofuran (5 mL) and cholesterol (260 mg), tetrabutylammonium iodide (51 mg) and t-butyl 4-(bromomethyl)phenyl carbamate (Synthesis, 22, 3619-3624 (2008), 400 mg) were added at 0° C. under argon flow. After raising temperature to 70° C., the mixture was refluxed for 3 days. The reaction mixture was diluted by adding dichloromethane (30 mL), washed with aqueous sodium chloride solution, dried with magnesium sulfate, and then filtered. The filtrate was concentrated under reduced pressure and the residue was subjected to silica gel column chromatography using ethyl acetate/hexane (1:20) as eluent to obtain the target compound SAC-0605 (40 mg, 7%): $^1$H-NMR (300 MHz, CDCl$_3$): 7.32-7.27 (m, 2H), 7.03-6.96 (m, 2H), 5.34 (m, 1H), 4.49 (s, 2H), 3.24 (m, 1H), 2.40-2.25 (m, 2H), 2.01-1.82 (m, 5H), 1.54-0.81 (m, 43H), 0.66 (s, 3H).

Synthesis Example 3-3

Preparation of SAC-0902

Sodium hydride (42 mg) was dissolved in tetrahydrofuran (3 mL). After adding cholesterol (100 mg) under argon flow, the mixture was stirred at room temperature for 30 minutes. After adding tetrabutylammonium iodide (51 mg) and 2-bromomethylnaphthalene (Aldrich, 69 mg), the mixture was stirred at room temperature for a day. The reaction mixture was diluted by adding diethyl ether (30 mL), washed with aqueous sodium chloride solution, dried with magnesium sulfate, and then filtered. The filtrate was concentrated under reduced pressure and the residue was subjected to silica gel column chromatography using ethyl acetate/hexane (1:15) as eluent to obtain the target compound SAC-0902 (13 mg, 9%): $^1$H-NMR (300 MHz, CDCl$_3$): 7.82-7.77 (m, 2H), 7.48-7.41 (m, 2H), 5.33 (d, 1H, J=5.1 Hz), 3.31 (m, 1H), 2.46-2.27 (m, 2H), 2.00-1.74 (m, 5H), 1.66-0.83 (m, 38H), 0.66 (s, 3H).

Scheme 8

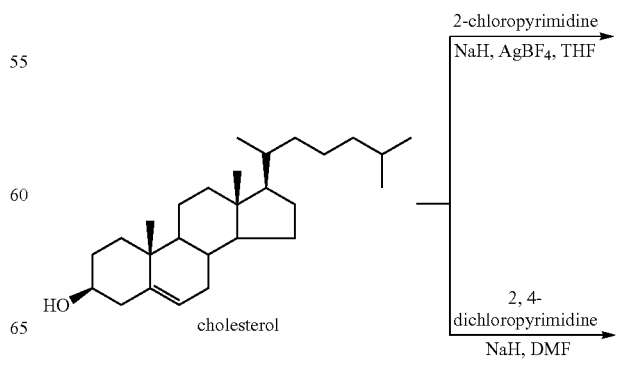

cholesterol

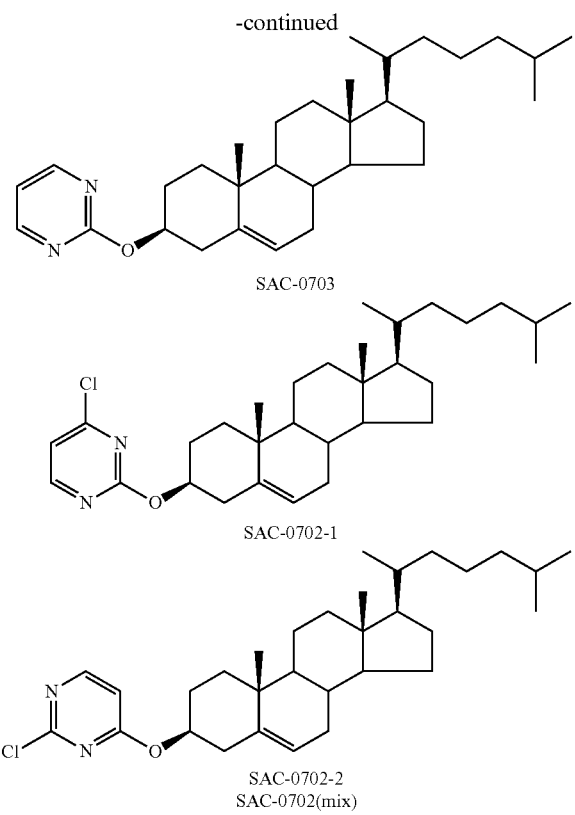

Synthesis Example 3-4

Preparation of SAC-0703

Cholesterol (506 mg) and sodium hydride (60%, 140 mg) were dissolved in tetrahydrofuran (3 mL) in a reaction vessel wrapped with aluminum foil. After adding silver tetrafluoroborate (Aldrich, 255 mg) and 2-chloropyrimidine (TCI, 100 mg) under argon flow, the mixture was refluxed for 3 days. After stopping reaction by adding water and filtering under reduced pressure, the residue was recrystallized in ethyl acetate/hexane (1:15) to obtain the target compound SAC-0703 (123 mg, 30%): $^1$H-NMR (300 MHz, CDCl$_3$): 8.47 (d, 2H, J=5.0 Hz), 6.86 (t, 1H, J=4.8 Hz), 5.39 (m, 1H), 4.87 (m, 1H), 2.5-2.45 (m, 2H), 2.02-1.79 (m, 5H) 1.56-0.83 (m, 33H), 0.66 (s, 3H).

Synthesis Example 3-5

Preparation of SAC-0702

Sodium hydride (42 mg) was dissolved in tetrahydrofuran (4 mL). After adding cholesterol (200 mg) under argon flow, the mixture was stirred at room temperature for 30 minutes. After adding 2,4-dichloropyrimidine (Aldrich, 88 mg), the mixture was stirred at room temperature for a day. The reaction mixture was diluted by adding dichloromethane (30 mL), washed with aqueous sodium chloride solution, dried with magnesium sulfate, and then filtered. The filtrate was concentrated under reduced pressure and the residue was subjected to silica gel column chromatography using ethyl acetate/hexane (1:30) as eluent to obtain the target compound SAC-0702: SAC-0702-1; $^1$H-NMR (300 MHz, CDCl$_3$): 8.33 (d, 1H, J=5.1 Hz), 6.91 (d, 1H, J=5.1 Hz), 5.40 (m, 1H), 5.00 (m, 1H), 2.50-2.40 (m, 2H), 2.02-0.83 (m, 38H) 0.67 (s, 3H); SAC-0702-2 $^1$H-NMR (300 MHz, CDCl$_3$): 8.23 (d, 1H, J=5.1 Hz), 6.57 (d, 1H, J=5.1 Hz), 5.40 (m, 1H), 4.85 (m, 1H), 2.50-2.40 (m, 2H), 2.02-0.83 (m, 38H) 0.67 (s, 3H).

Synthesis Example 4

Synthesis of Rk1 Derivatives 4

Compounds whose absolute configuration of the 3-OH group of cholesterol is opposite were designed and synthesized.

Scheme 9

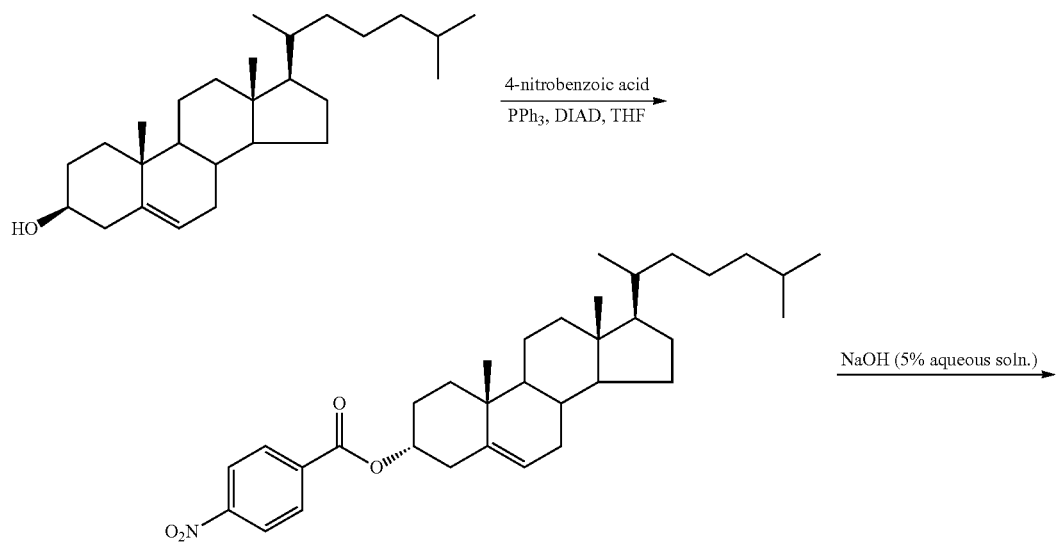

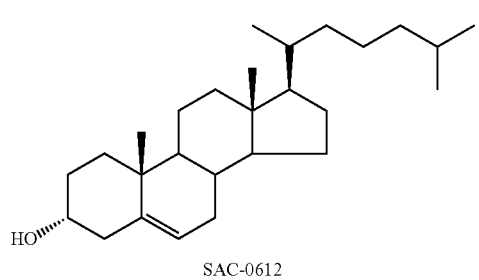
SAC-0612

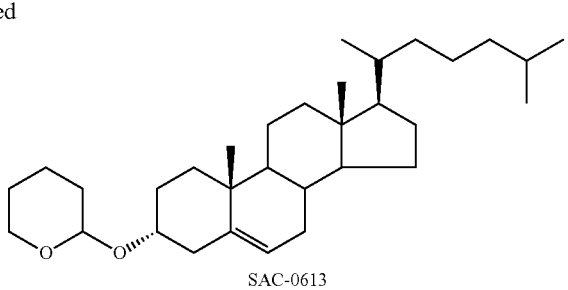
SAC-0613

Synthesis Example 4-1

Preparation of SAC-0612

Cholesterol (2 g) was dissolved in tetrahydrofuran (10 mL). After adding triphenylphosphine (Aldrich, 5.15 g), 4-nitrobenzoic add (Aldrich, 3.45 g) and diethyl azodicarboxylate (Aldrich, 4.23 mL) under argon flow, the mixture was stirred at room temperature for 13 hours and then at 40° C. for 30 minutes. The reaction mixture was diluted by adding diethyl ether (100 mL), washed with aqueous sodium chloride solution, dried with magnesium sulfate, and then filtered. The filtrate was concentrated under reduced pressure and the residue was subjected to silica gel column chromatography using ethyl acetate/hexane (1:10) as eluent to obtain the target compound. After dissolving the target compound in tetrahydrofuran (7 mL) and lowering temperature to 0° C., 5% aqueous sodium hydroxide solution (6 mL) was added. The reaction mixture was stirred at room temperature for 12 hours, diluted by adding chloroform (50 washed with water, 1 N hydrochloric acid solution and sodium chloride, dried with magnesium sulfate, and then filtered. The filtrate was concentrated under reduced pressure and the residue was subjected to silica gel column chromatography using ethyl acetate/hexane (1:4) as eluent to obtain the target compound SAC-0612 (480 mg, 24%): $^1$H-NMR (300 MHz, CDCl$_3$): 5.39 (m, 1H), 3.99 (m, 1H), 2.55 (m, 1H), 2.07 (t, 1H, J=2.6 Hz), 2.02-0.83 (m, 39H), 0.66 (s, 3H).

Synthesis Example 4-2

Preparation of SAC-0613

SAC-0612 (49 mg) obtained above was dissolved in dichloromethane (2 mL). After adding dihydropyran (Aldrich, 0.12 mL) and p-toluenesulfonic acid (7 mg) under argon flow, the mixture was stirred at room temperature for 4 hours. The reaction mixture was diluted by adding ethyl acetate (30 mL), washed with water, dried with magnesium sulfate, and then filtered. The filtrate was concentrated under reduced pressure and the residue was subjected to silica gel column chromatography using ethyl acetate/hexane (1:25) as eluent to obtain the target compound SAC-0613 (28 mg, 47%): $^1$H-NMR (300 MHz, CDCl$_3$): 5.24 (m, 1H), 4.59 (m, 1H), 3.89-3.82 (m, 2H), 3.44 (m, 1H), 2.46-2.18 (m, 2H), 2.00-0.83 (m, 44H), 0.65 (s, 3H).

Synthesis Example 5

Synthesis of Rk1/Rg3 Derivatives 1

Compounds with cyclic ether groups introduced as bioisosteres and, at the same time, with double bonds or alcohol groups introduced at the Rk1 chain or the Rg3 chain respectively were designed and synthesized. In particular, various derivatives with tetrahydropyran and tri-O-acetyl-D-glucan groups, which are expected to be influential in biological activity, introduced were synthesized.

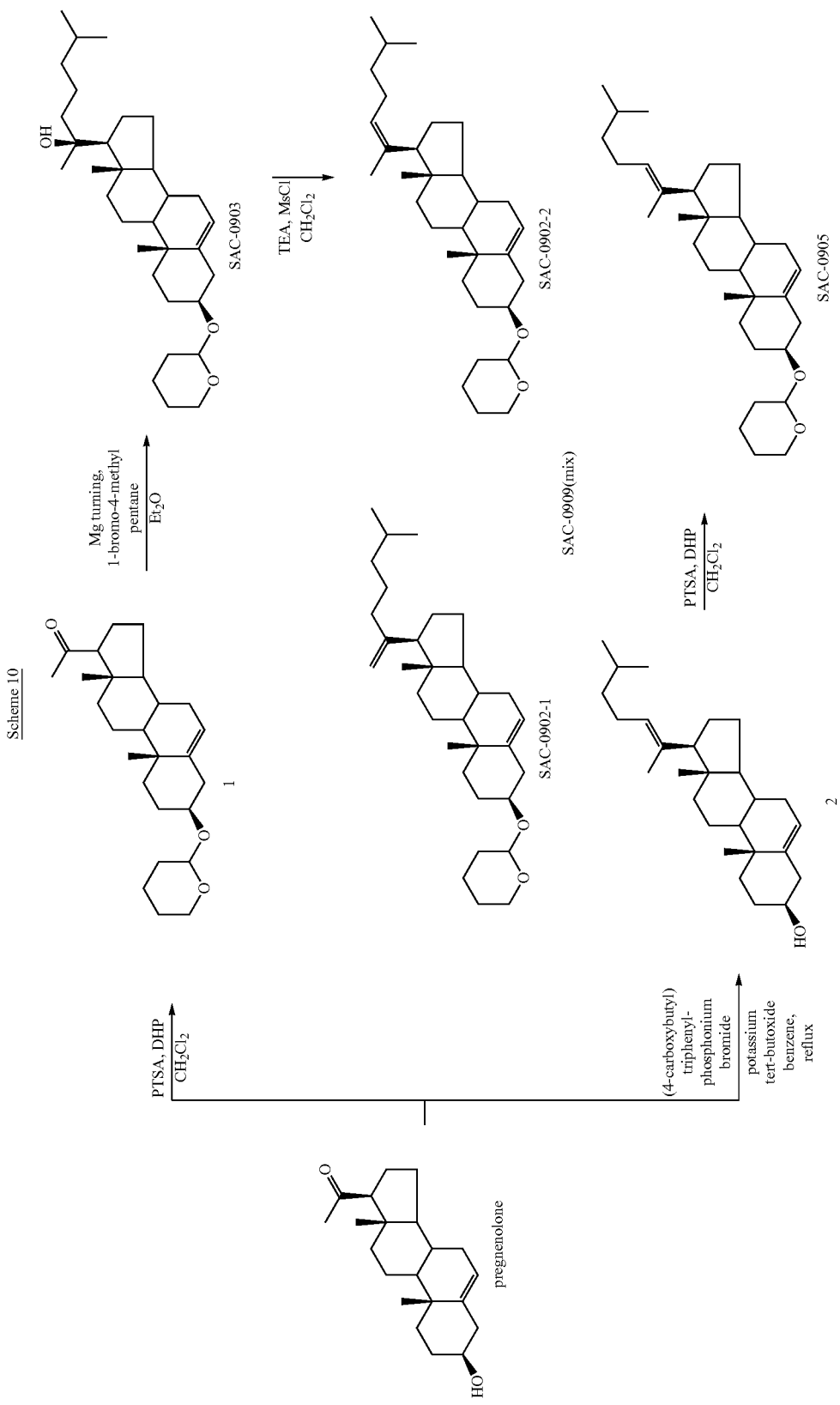

Synthesis Example 5-1

Preparation of SAC-0903

Pregnenolone (TCI, 500 mg) was dissolved in dichloromethane (8 mL). After adding dihydropyran (Aldrich, 0.72 mL) and p-toluenesulfonic add (TCI, 76 mg) under argon flow, the mixture was stirred at room temperature for 8 hours. The reaction mixture was diluted by adding ethyl acetate (20 mL), washed with water, dried with magnesium sulfate, and then filtered. The filtrate was concentrated under reduced pressure and the residue was subjected to silica gel column chromatography using ethyl acetate/hexane (1:10) as eluent to obtain the compound 1 (403 mg, 63.6%).

Magnesium turning (Aldrich, 39 mg) was dissolved in diethyl ether (1 mL) under argon flow and, after adding catalytic amount of iodine, 1-bronco-4-methylpentane (Aldrich, 0.03 mL) was slowly added. When the magnesium turning disappeared, the compound 1 (50 mg) dissolved in diethyl ether (2 mL) was slowly added. 10 minutes later, reaction was stopped by adding 2 N hydrochloric acid solution and the reaction mixture was extracted with ethyl acetate (20 dried with magnesium sulfate, and then filtered. The filtrate was concentrated under reduced pressure and the residue was subjected to silica gel column chromatography using ethyl acetate/hexane (1:10) as eluent to obtain the target compound SAC-0903 (11 mg, 18%): $^1$H-NMR (500 MHz, CDCl$_3$) δ 5.33 (t, 1H, J=6.25 Hz), 4.69 (m, 1H), 3.90 (m, 1H), 3.53-3.45 (m, 2H), 2.34-2.30 (m, 2H), 2.20-0.82 (m, 47H).

Synthesis Example 5-2

Preparation of SAC-0909

SAC-0903 (50 mg) prepared in Synthesis Example 1-1 was dissolved in dichloromethane (3 mL) under argon flow. After lowering temperature to 0° C., triethylamine (Aldrich, 0.07 mL) and methylsulfonyl chloride (Aldrich, 0.015 mL) were added. After raising temperature to 40° C. and stirring for 3 hours, temperature was lowered again to room temperature. The reaction mixture was diluted by adding dichloromethane (10 mL), washed with aqueous sodium bicarbonate solution, dried with magnesium sulfate, and then filtered. The filtrate was concentrated under reduced pressure and the residue was subjected to silica gel column chromatography using ethyl acetate/hexane (1:10) as eluent to obtain the target compounds: SAC-0909-1: $^1$H-NMR (500 MHz, CDCl$_3$) δ 5.34 (m, 1H), 4.84 (s, 1H), 4.74 (s, 1H), 4.69 (m, 1H), 3.90 (m, 1H), 3.53-3.45 (m, 2H), 2.34-0.52 (m, 45H); SAC-0909-2: $^1$H-NMR (300 MHz, CDCl$_3$) δ 5.34 (m, 1H), 5.15 (m, 1H), 4.69 (m, 1H), 3.90 (m, 1H), 3.53-3.45 (m, 2H), 2.34-0.52 (m, 46H).

Synthesis Example 5-3

Preparation of SAC-0905

Isohexyltriphenylphosphonium bromide (*J. Org. Chem.*, 44, 3760-3765 (1979), 900 mg) was dissolved in benzene (8 mL) under argon flow. After adding 1 M potassium t-butoxide solution (Alfa Aesar, 2.1 mL), the mixture was refluxed for 25 minutes. Pregnenolone (TCI, 200 mg) dissolved in benzene (2 mL) was added to the reaction mixture using a syringe and refluxed for 2 hours and 25 minutes. After lowering temperature to room temperature and stopping reaction by adding water (20 mL), the reaction mixture was extracted with diethyl ether, dried with magnesium sulfate, and then filtered. The filtrate was concentrated under reduced pressure and the residue was subjected to silica gel column chromatography using ethyl acetate/hexane (1:5) as eluent to obtain the target compound 2 (54 mg, 22%). The prepared compound 2 (23 mg) was dissolved in dichloromethane (4 mL) under argon flow and, after adding dihydropyran (Aldrich, 0.04 mL) and p-toluenesulfonic acid (TCI, 3 mg), stirred at room temperature for 3 hours. The reaction mixture was diluted by adding ethyl acetate (10 mL), washed with water, dried with magnesium sulfate, and then filtered. The filtrate was concentrated under reduced pressure and the residue was subjected to silica gel column chromatography using ethyl acetate/hexane (1:10) as eluent to obtain the target compound SAC-0905 (16 mg, 57%): $^1$H-NMR (500 MHz, CDCl$_3$) δ 5.33 (m, 1H), 5.15 (m, 1H), 4.69 (m, 1H), 3.90 (m, 1H), 3.53-3.45 (m, 2H), 2.34-2.29 (m, 2H), 2.21-0.52 (m, 44H).

Scheme 11

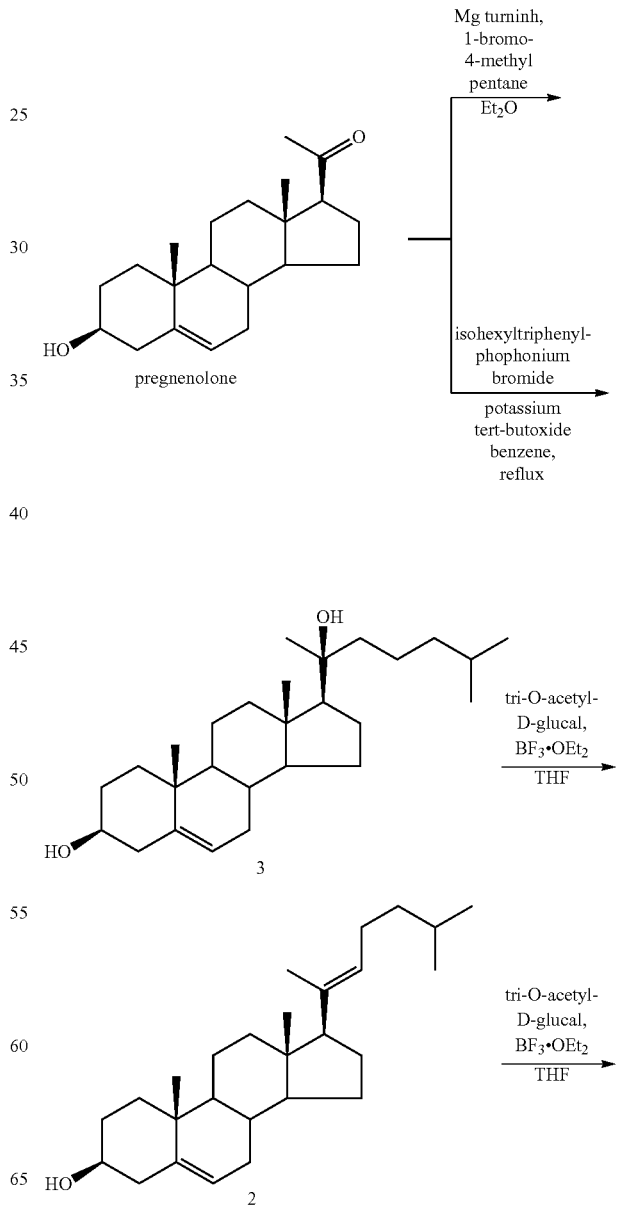

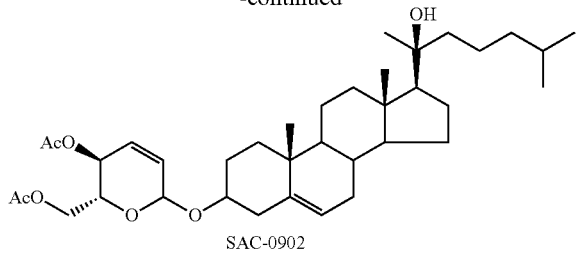

SAC-0902

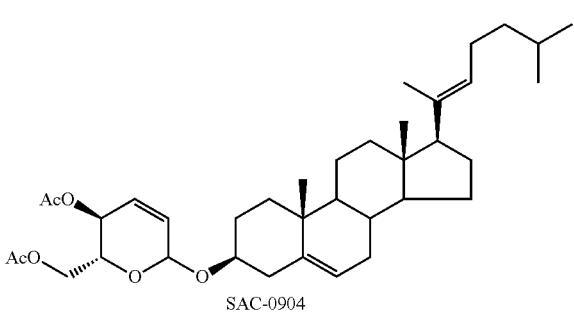

SAC-0904

Synthesis Example 5-4

Preparation of SAC-0902

Magnesium turning (Aldrich, 92 mg) was dissolved in tetrahydrofuran (3 mL) under argon flow and, after adding catalytic amount of iodine, 1-bromo-4-methylpentane (Aldrich, 0.69 mL) was slowly added. When the magnesium turning disappeared, pregnenolone (Aldrich, 200 mg) dissolved in tetrahydrofuran (4 mL) was slowly added. 10 minutes later, reaction was stopped by adding 2 N hydrochloric acid solution and the reaction mixture was extracted with ethyl acetate (20 mL), dried with magnesium sulfate, and then filtered. The filtrate was concentrated under reduced pressure and the residue was subjected to silica gel column chromatography using ethyl acetate/hexane (1:10) as eluent to obtain the compound 3 (95 mg, 15%), which is commercially available (Fluka H6378).

The compound 3 (43 mg) was dissolved in diethyl ether (5 mL). After adding tri-O acetyl-D-glucal (Aldrich, 81 mg) and boron trifluoride diethyl etherate (Aldrich, 0.012 mL) under argon flow, the mixture was stirred at 0° C. for 1 hour. The reaction mixture was diluted by adding diethyl ether (30 mL), washed with aqueous sodium bicarbonate solution, dried with sodium sulfate, and then filtered. The filtrate was concentrated under reduced pressure and the residue was subjected to silica gel column chromatography using ethyl acetate/hexane (1:10) as eluent to obtain the target compound SAC-0902 (7.6 mg, 12%): $^1$H-NMR (500 MHz, CDCl$_3$) δ 5.86 (d, 1H, J=10.2 Hz), 5.81 (d, 1H, =10.2 Hz), 5.38 (m. 1H), 5.27 (m, 1H), 5.14 (m, 1H), 4.23-4.09 (m. 3H), 3.55 (m, 1H), 2.41-2.32 (m, 2H), 2.07-2.06 (m, 7H), 2.14-0.52 (m, 38H).

Synthesis Example 5-5

Preparation of SAC-0904

The compound 2 (317 mg) prepared in Synthesis Example 5-3 was dissolved in diethyl ether (15 mL). After adding tri-O-acetyl-D-glucal (Aldrich, 672 mg) dissolved in diethyl ether (7 mL) and boron trifluoride diethyl etherate (Aldrich, 0.3 mL) under argon flow, the mixture was stirred at 0° C. for 3 hours. After raising temperature to room temperature, the reaction mixture was diluted by adding diethyl ether (30 washed with aqueous sodium bicarbonate solution, dried with sodium sulfate, and then filtered. The filtrate was concentrated under reduced pressure and the residue was subjected to silica gel column chromatography using ethyl acetate/hexane (1:10) as eluent to obtain the target compound SAC-0904 (270 mg, 54.9%): $^1$H-NMR (500 MHz, CDCl$_3$) δ 5.86 (d, 1H, J=10.2 Hz), 5.81 (d, 1H, J=102 Hz), 5.34 (m, 1H), 528 (d, 1H, J=9.0 Hz), 5.15-5.13 (m, 2H), 4.25-4.1.4 (m. 3H), 3.54 (m, 1H), 2.40-2.30 (m, 2H), 2.07-2.06 (m, 6H), 2.02-0.52 (m, 38H).

Synthesis Example 6

Synthesis of Rk1/Rg3 Derivatives 2

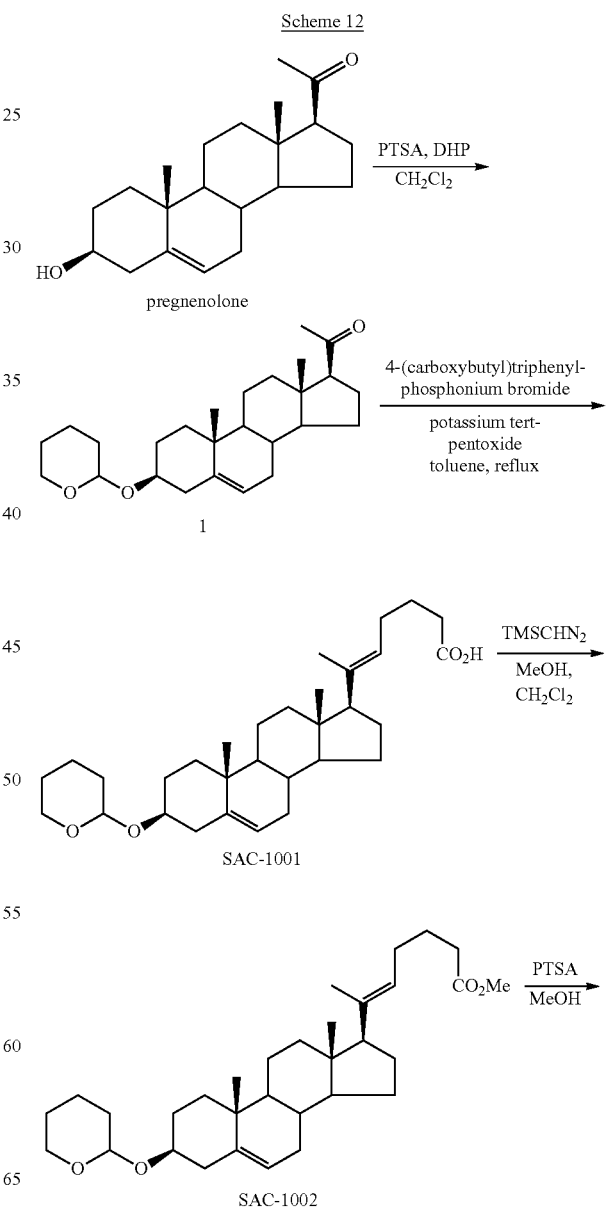

Scheme 12

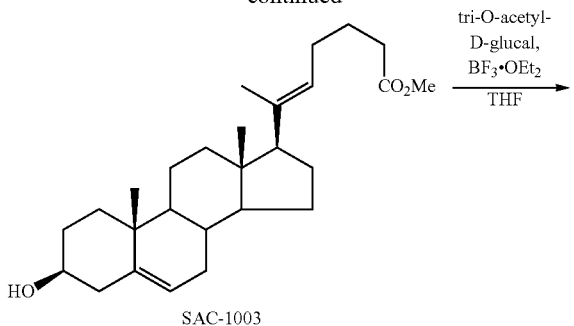

SAC-1003

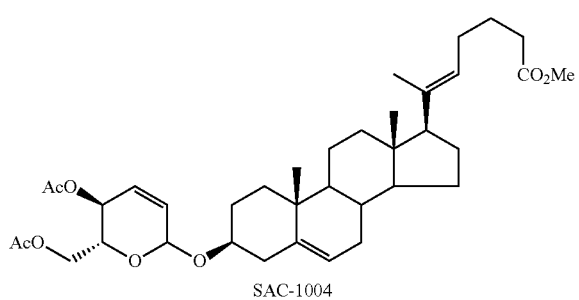

SAC-1004

Synthesis Example 6-1

Preparation of SAC-1001

(4-Carboxybutyl)triphenylphosphonium bromide (TCI, 665 mg) was dissolved in toluene (4 mL) under argon flow. After adding potassium t-butoxide (Alfa Aesar, 1.76 mL), the mixture was refluxed for 2 hours. The compound 1 (200 mg) obtained in Synthesis Example 1-1 was dissolved in toluene (2 mL) and added to the reaction mixture. After refluxing for 4 hours and lowering temperature to room temperature, pH was adjusted to 3 using 2 N hydrochloric acid solution. Then, the reaction solution was diluted by adding ethyl acetate (20 mL), dried with magnesium sulfate, filtered, and concentrated under reduced pressure. The residue was subjected to silica gel column chromatography using ethyl acetate/hexane/acetic acid (50:100:1) as eluent to obtain the target compound SAC-1001 (158 mg, 65%): $^1$H-NMR (300 MHz, CDCl$_3$) δ 5.32 (m, 1H), 5.13 (m, 1H), 4.71 (m, 1H), 3.89 (m, 1H), 3.53-3.44 (m, 2H), 2.37-0.53 (m, 42H).

Synthesis Example 6-2

Preparation of SAC-1002

SAC-1001 (158 mg) obtained in Synthesis Example 6-1 was dissolved in methanol/dichloromethane (1:2, 6 mL) and 2 M trimethylsilyldiazomethane solution (Aldrich, 0.31 mL) was slowly added. When no more foaming occurred, the mixture was concentrated under reduced pressure and the residue was subjected to silica gel column chromatography using ethyl acetate/hexane (1:15) as eluent to obtain the target compound SAC-1002 (113.8 mg, 70%): $^1$H-NMR (400 MHz, CDCl$_3$) δ 5.33 (m, 1H), 5.14-5.11 (t, 6.9 Hz), 4.69 (m, 1H), 3.90 (m, 1H), 3.64 (s, 3H), 3.53-3.44 (m, 2H), 2.34-0.52 (m, 41H).

Synthesis Example 6-3

Preparation of SAC-1003

SAC-1002 (120 mg) obtained in Synthesis Example 6-2 was dissolved in methanol (5 mL). After adding p-toluenesulfonic acid (TCI, 11 mg), the mixture was stirred at room temperature for 1 hour. The reaction mixture was diluted by adding ethyl acetate (10 mL), washed with water, dried with magnesium sulfate, and then filtered. The filtrate was concentrated under reduced pressure and the residue was subjected to silica gel column chromatography using ethyl acetate/hexane (1:5) as eluent to obtain the target compound SAC-1003 (85 mg, 85%): $^1$H-NMR (300 MHz, CDCl$_3$) δ 5.35 (m, 1H), 5.16-5.12 (t, 1H, J=7.1 Hz), 3.66 (s, 3H), 3.52 (m, 1H), 2.33-2.22 (m, 4H), 2.10-0.63 (m, 29H), 0.53 (s, 3H).

Synthesis Example 6-4

Preparation of SAC-1004

SAC-1003 (13.4 mg) prepared in Synthesis Example 6-3 was dissolved in tetrahydrofuran (1 mL). After adding tri-O-acetyl-D-glucal (Aldrich, 26 mg) and boron trifluoride diethyl etherate (Aldrich, 0.012 mL) under argon flow, the mixture was stirred at 0° C. for 10 hours. After raising temperature to room temperature, the reaction mixture was diluted by adding diethyl ether (5 mL), washed with aqueous sodium bicarbonate solution, dried with sodium sulfate, and then filtered. The filtrate was concentrated under reduced pressure and the residue was subjected to silica gel column chromatography using ethyl acetate; hexane (1:10) as eluent to obtain the target compound SAC-1004 (11 mg, 56%): $^1$H-NMR (300 MHz, CDCl$_3$) δ 5.89-5.80 (m, 2H), 5.37-5.27 (m. 2H), 5.17-5.14 (m, 2H), 4.23-4.1.6 (m, 3H), 3.66 (s. 3H), 3.56 (m, 1H), 2.38-2.28 (m, 4H), 2.17-0.53 (m, 37H).

Scheme 13

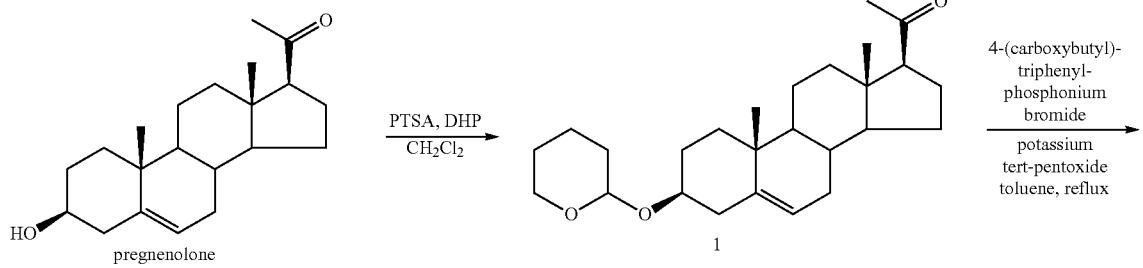

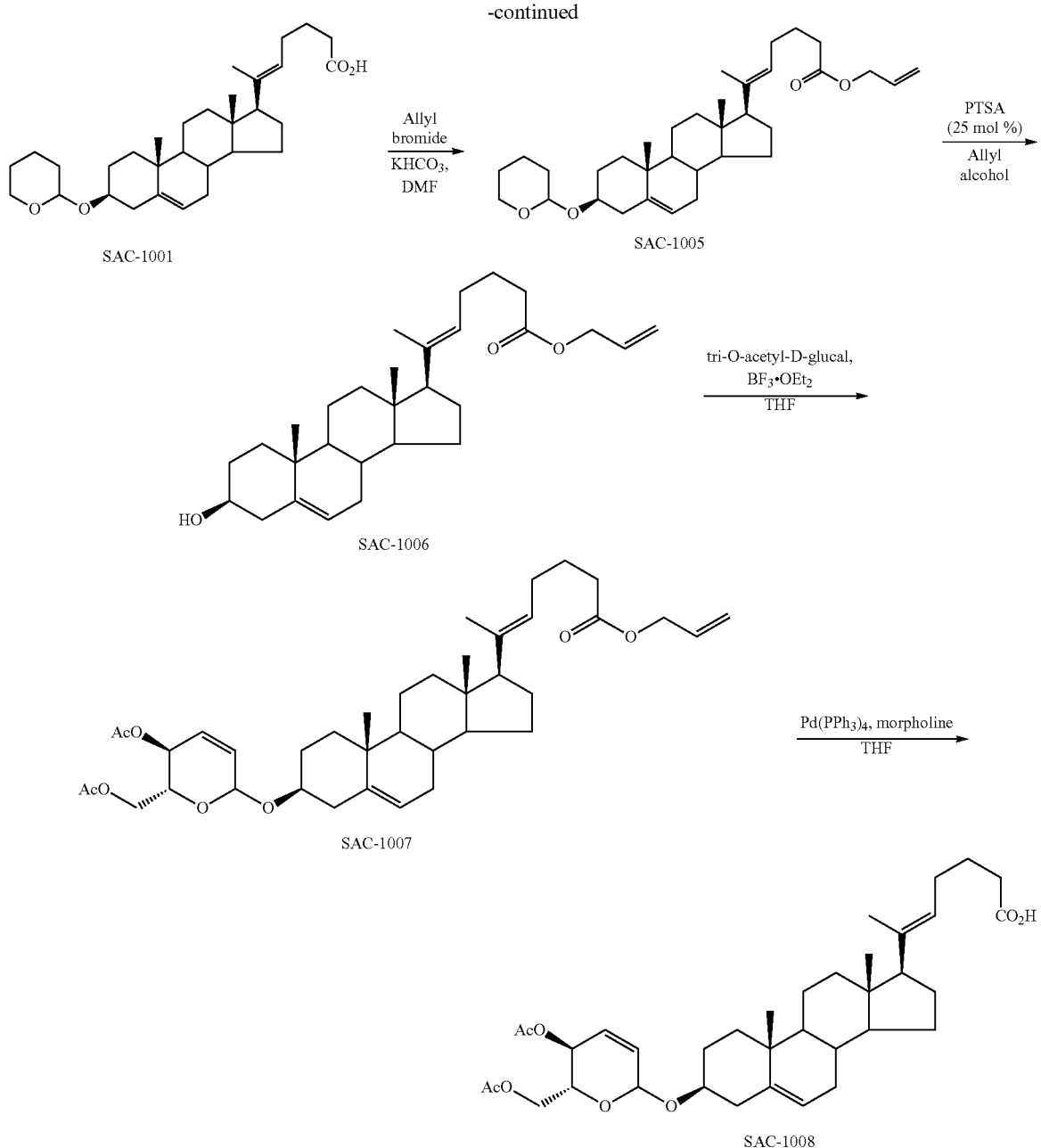

Synthesis Example 6-5

Preparation of SAC-1005

SAC-1001 (300 mg) obtained in Synthesis Example 6-1 was dissolved in dimethylformamide (4 mL) and allyl bromide (0.08 mL) and potassium bicarbonate (185 mg) were added. After stirring for 15 hours, the mixture was diluted with ethyl acetate (15 mL), dried with sodium sulfate, and then filtered. The residue was subjected to silica gel column chromatography using ethyl acetate/hexane (1:10) as eluent to obtain the target compound SAC-1005 (195 mg, 60%): $^1$H-NMR (500 MHz, CDCl$_3$) δ 5.89 (m, 1H), 5.39-5.07 (m, 4H), 4.69 (m, 4.56-4.55 (m, 2H), 3.91-3.88 (m, 1H), 3.53-3.45 (m, 2H), 2.38-0.81 (m, 41H).

Synthesis Example 6-6

Preparation of SAC-1006

SAC-1005 (195 mg) obtained in Synthesis Example 6-5 was dissolved in allyl alcohol (5 mL). After adding p-toluenesulfonic acid (TCI, 16 mg) and stirring at room temperature for 1 hour, the reaction mixture was diluted by adding ethyl acetate (20 mL), washed with water, dried with magnesium sulfate, and then filtered. The filtrate was concentrated under reduced pressure and the residue was subjected to silica gel column chromatography using ethyl acetate/hexane (1:15) as eluent to obtain the target compound SAC-1006 (98 mg, 60%): $^1$H-NMR (300 MHz, CDCl$_3$) δ 5.92 (m, 1H), 5.35-5.11 (m, 4H), 4.57-4.55 (m, 2H), 3.51 (m, 2.35-2.22 (m, 4H), 2.10-0.53 (m, 32H).

Synthesis Example 6-7

Preparation of SAC-1007

SAC-1006 (191.8 mg) prepared in Synthesis Example 6-6 was dissolved in tetrahydrofuran (10 mL). After adding tri-O-acetyl-D-glucal (Aldrich, 355 mg) and boron trifluoride diethyl etherate (Aldrich, 0.32 mL) under argon flow, the mixture was stirred at 0° C. for 10 hours. After raising temperature to room temperature, the reaction mixture was diluted by adding diethyl ether (30 mL), washed with aqueous sodium bicarbonate solution, dried with sodium sulfate, and then filtered. The filtrate was concentrated under reduced pressure and the residue was subjected to silica gel column chromatography using ethyl acetate/hexane (1:10) as eluent to obtain the target compound SAC-1007 (139 mg, 49%): $^1$H-NMR (300 MHz, CDCl$_3$) δ 5.97-5.79 (m, 3H), 5.34-5.12 (m, 6H), 4.57-4.55 (m, 2H), 4.26-4.07 (m, 3H), 3.55 (m, 1H), 2.37-2.30 (m, 4H), 2.17-0.53 (m, 37H).

Synthesis Example 6-8

Preparation of SAC-1008

SAC-1007 (67 mg) prepared in Synthesis Example 6-7 was dissolved in tetrahydrofuran (5 After adding tetrakis(triphenylphosphine)palladium (Aldrich, 136 mg) and morpholine (Aldrich, 0.01 mL) under argon flow, the mixture was stirred for 12 hours. After stopping reaction with 2 N hydrochloric add solution, the reaction mixture was diluted by adding diethyl ether (5 mL), dried with sodium sulfate, and then filtered. The filtrate was concentrated under reduced pressure and the residue was subjected to silica gel column chromatography using dichloromethane/methanol (10:1) as eluent to obtain the target compound SAC-1008 (12.5 mg, 20%): $^1$H-NMR (400 MHz, CDCl$_3$) δ 5.92-5.78 (m, 2H), 5.33-5.26 (m, 2H), 5.19-5.08 (m, 2H), 4.24-4.07 (m, 3H), 3.54 (m, 1H), 2.41-2.31 (m, 3H), 2.23-0.52 (m, 39H).

Test Examples

Culturing Example: Culturing of Vascular Endothelial Cells

Human umbilical vein endothelial cells (HUVECs) and human retinal endothelial cells (HRECs) purchased from Cell Systems (USA) were seeded on a 100-mm culture dish in M199 medium (Life Technologies, USA) containing 20% (w/v) fetal bovine serum (FBS, HyClone, Canada), 100 units/mL penicillin (Invitrogen, USA), 100 µg/mL streptomycin (invitrogen, USA), 3 ng/mL basic fibroblast growth factor (bFGF, Upstate Biotechnology, USA) and 5 units/mL heparin and cultured in a 5% CO$_2$ incubator at 37° C.

Test Example 1

Figure 1B:
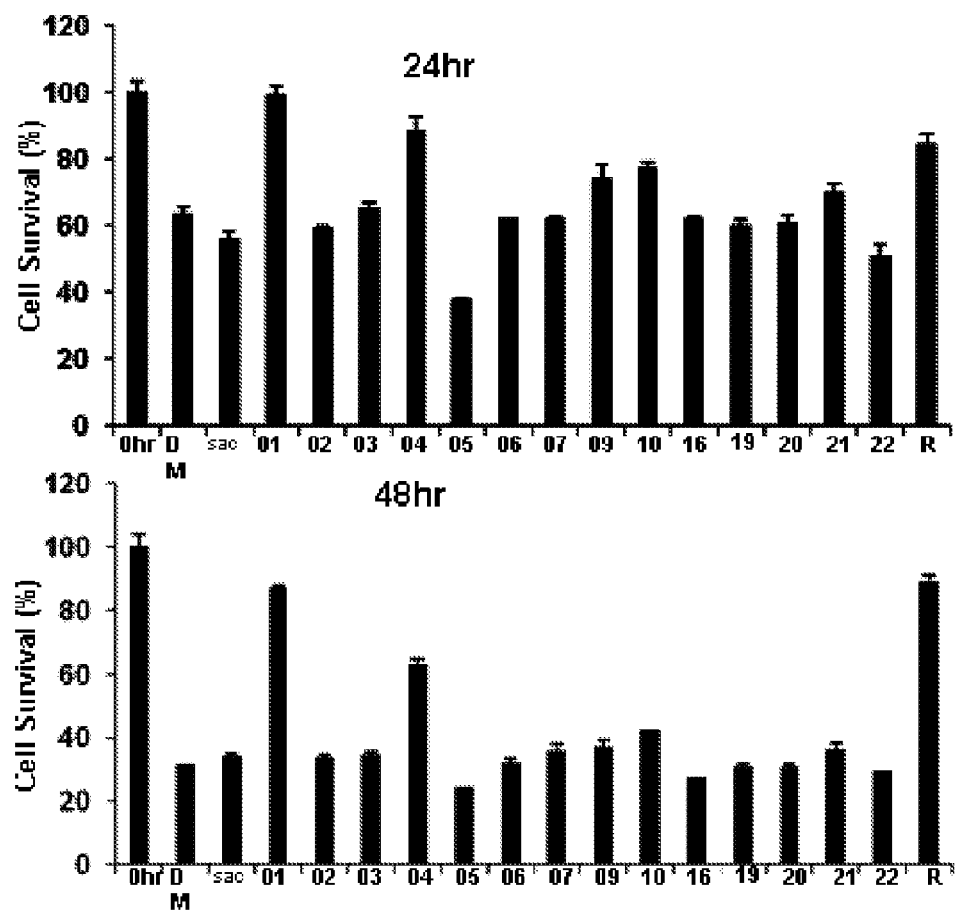
Figure 2A:
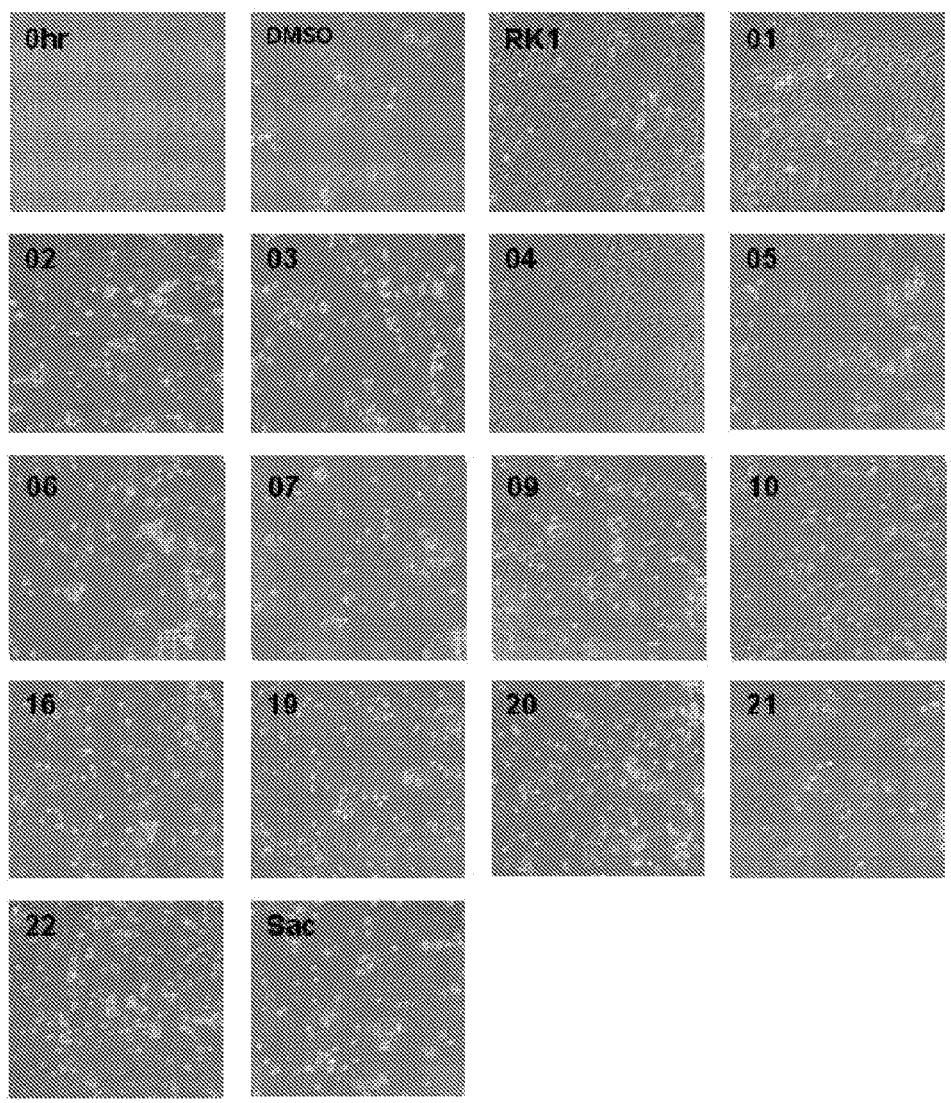

Screening of Synthesized Derivatives Based on Ability of Inhibiting Apoptosis of Vascular Endothelial Cells Based on the previous researches performed by the inventors, the synthesized derivatives of Rk1 having steroid backbone and having the ability of inhibiting apoptosis of vascular endothelial cells and inhibiting permeability were screened. First, the ability of inhibiting apoptosis of vascular endothelial cells was measured. HUVECs (3×10$^5$ cells/well) were seeded on a 24-well plate in M199 medium (1 mL) containing 20% fetal bovine serum. The next day, the cells were transferred to serum-free 11199 medium containing 5 µg/mL (FIG. 1a) or 10 µg/mL (FIG. 1b) of the compound synthesized in Synthesis Example 1-4, Cell viability was determined by MTT assay (Mosmann T, *Journal of ImmunalogiCal Methods* 65(1-2): 55-63 (1983); Cory A H, et al., *Cancer Communications* 3(7): 207-12 (1991)) 24 hours and 48 hours later. As a result (it was confirmed that the synthesized derivatives Sac0504 and Sac0601 have the ability of inhibiting apoptosis comparable to that of Rk1. Also, observation of cell morphologies revealed that the derivatives have the ability of protecting the vascular endothelial cells (FIG. 2a).

Figure 2B:
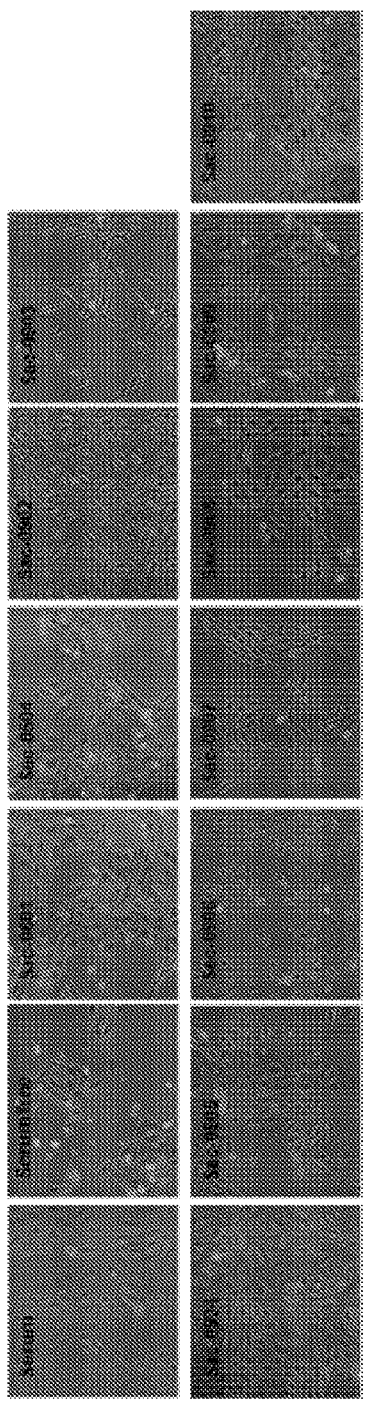

Also, HRECs were treated with the compounds synthesized in Synthesis Example 5 and MIT assay was performed 48 hours later in the same manner as described above. As seen from FIG. 1c, the compounds synthesized in Synthesis Example 5 showed the ability of inhibiting apoptosis. In particular, the synthesized derivatives Sac0904 and Sac0902 showed better ability of inhibiting apoptosis than Sac0601. Also, observation of cell morphologies revealed that the derivatives have the ability of protecting the vascular endothelial cells (FIG. 2b).

Figure 2C:
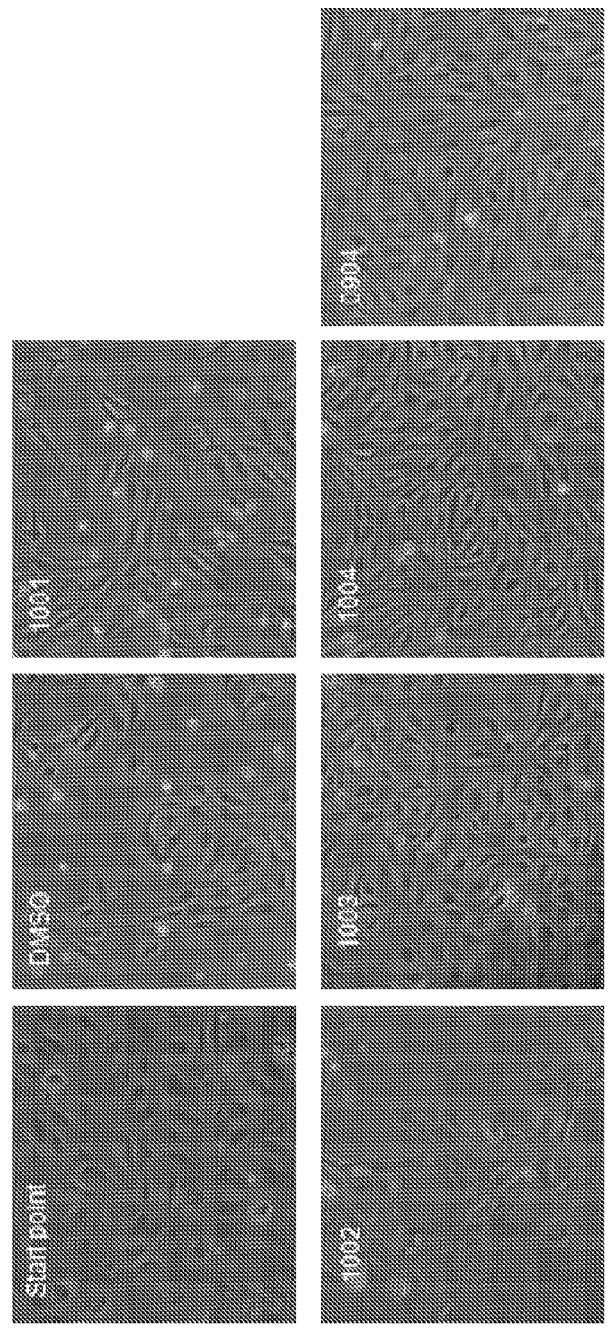
Figure 2D:
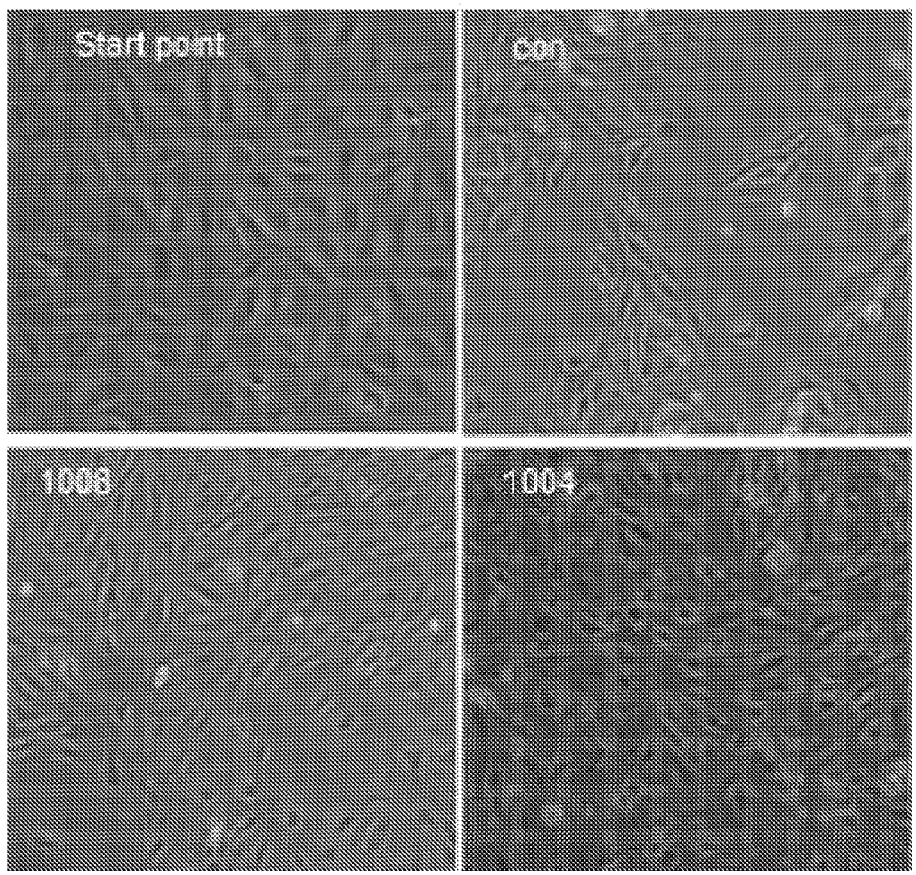

In order to improve the physical properties, particularly water solubility (c log P of SAC-0904=9.9114), of SAC-0904 showing superior activity and thus to improve value as candidate material for drug discovery, the compound with an ester group as a bioisostere was prepared to decrease the c log P value and provide appropriate activity (see Synthesis Example 7). SAC-1004 had improved water solubility with c log P being 7.9424 and showed improved ability of protecting the vascular endothelial cells over SAC-0904. Also, the acid compound wherein the methyl ester formed by the introduction of the ester group was hydrolyzed was synthesized to provide improved water solubility and activity. MYT assay was performed for the compounds synthesized in Synthesis Example 6 in the same manner as described above 48 hours after treatment. As seen from FIGS. 1.d-1e, the compounds newly synthesized to improve water solubility showed the ability of inhibiting apoptosis comparable to that of SAC-0904. SAC-1004 exhibited improved ability of inhibiting apoptosis over SAC-0904. Also, observation of cell morphologies revealed that the compounds synthesized in Synthesis Example 7 have the ability of protecting the vascular endothelial cells (FIGS. 2c-2d).

Test Example 2

Screening of Synthesized Derivatives Based on Change in Cytoskeleton

Figure 3A:
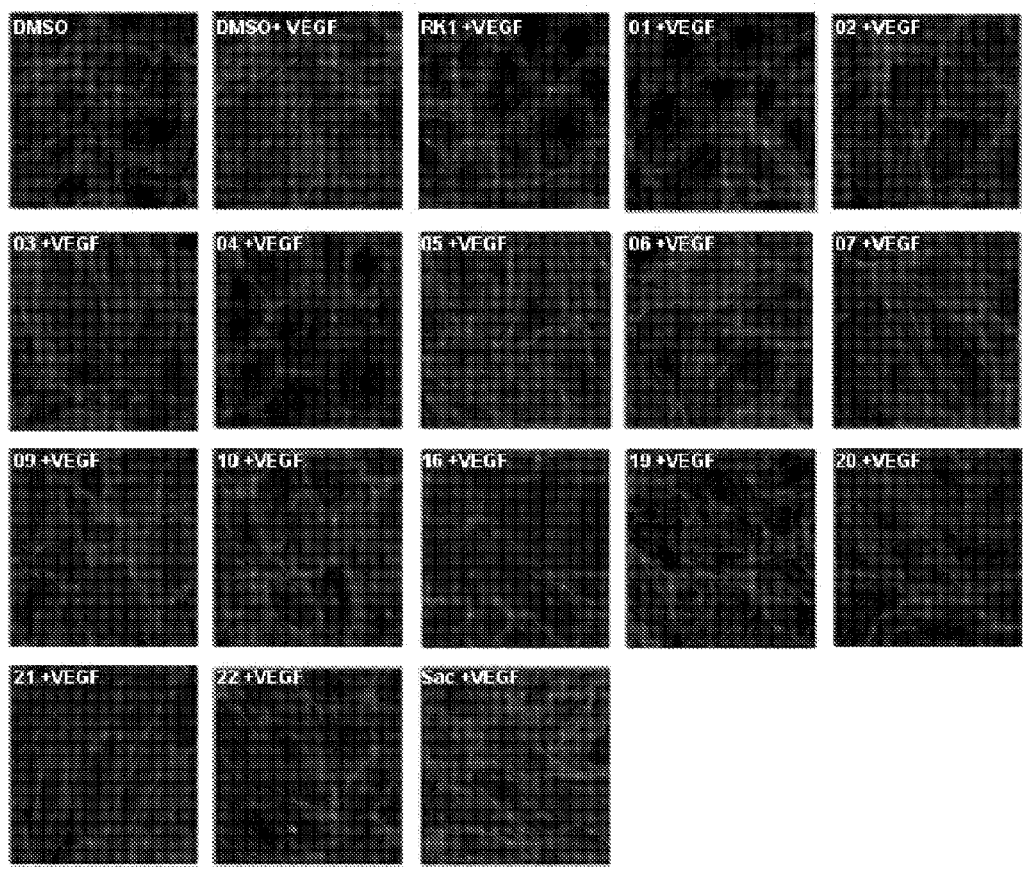
FIGS. 3*a*-3*c* show that the Rk1 analogs Sac0504 and Sac0601 inhibit the formation of actin stress fibers induced by VEGF. Confluent HUVECs were pretreated with the compounds (10 μg/mL) for 60 minutes before treating with 20 ng/mL VEGF (1 hr). The cells were then stained with rhodamine phalloidin.
Figure 3B:
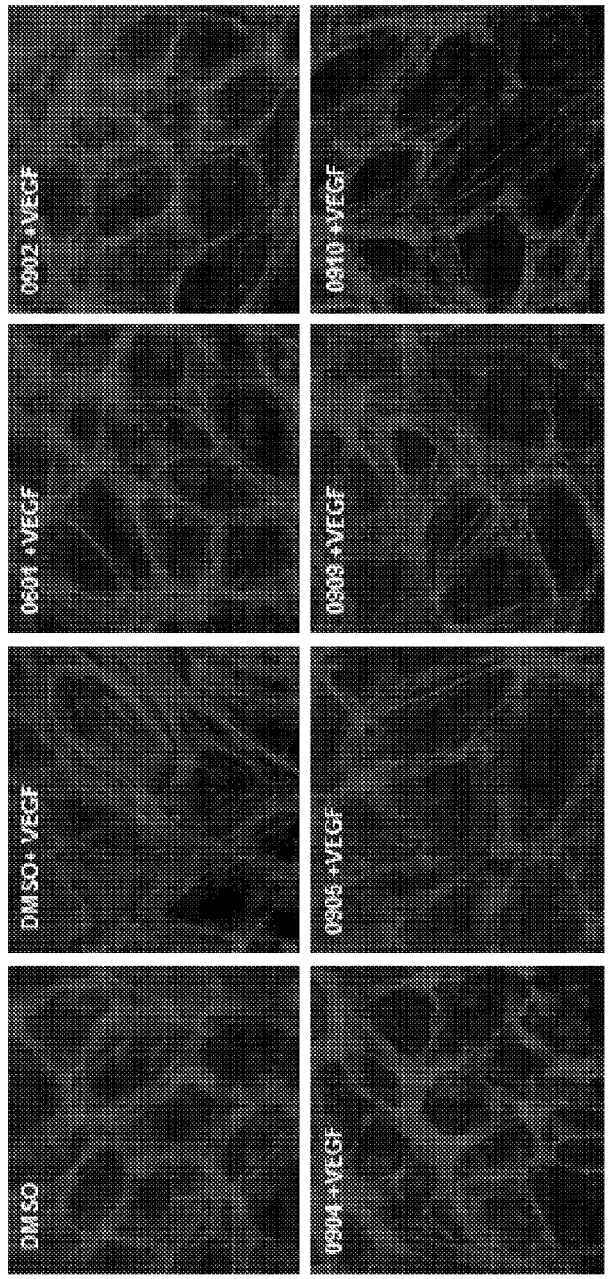
Figure 3C:
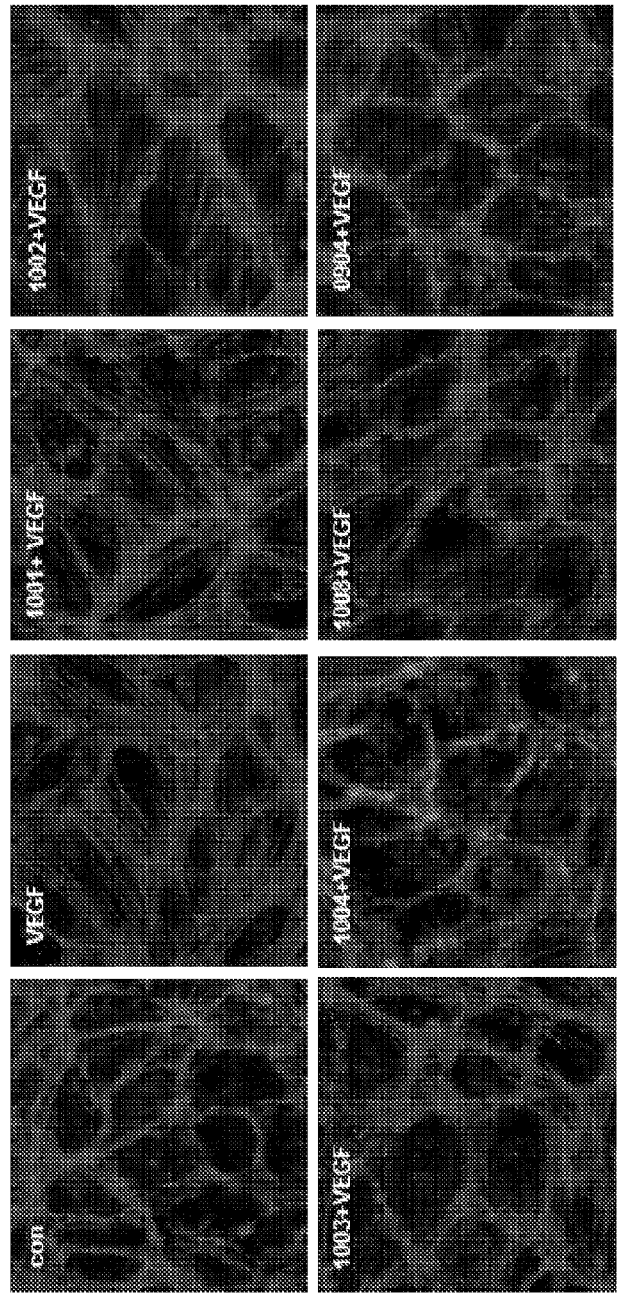

It is known that the change in the actin structure of the cytoskeleton is closely related with the permeability of vascular endothelial cells. Increased permeability of vascular endothelial cells leads to increased formation of actin stress fibers and decrease of cortical actin ring structures. Based on this, the ability of inhibiting vascular endothelial permeability of the synthesized Rk1 derivatives was screened. Confluent HUVECs were pretreated with the synthesized compounds (10 µg/mL) for 1 hour before treating with 20 ng/mL VEGF (Upstate Biotechnology). Subsequently, the cells were fixed with 4% paraformaldehyde for 20 minutes at room temperature and washed 3 times with PBS (pH 7.4). Then, the cells were permeabilized with 0.1% Triton X-100/PBS and reacted with 0.1 mg/mL rhodamine phalloidin (Molecular Probes) for 1 hour. Then, the cells were observed under a fluorescence microscope (Olympus). As in the screening of the ability of inhibiting apoptosis of vascular endothelial cells, Sac0504 and Sac0601 inhibited the formation of actin stress fibers induced by VEGF and increased the cortical actin ring structure (FIG. 3a). The compounds synthesized in Synthesis Example 5 also inhibited the formation of actin stress fibers. In particular, the pretreatment with Sac0904 and Sac0902 inhibited the formation of actin stress fibers induced by VEGF and increased the cortical actin ring structure (FIG. 3b). The compounds synthesized in Synthesis Example 6 also inhibited the formation of actin stress fibers. In particular, the pretreatment with Sac1004 inhibited the formation of actin stress fibers induced by VEGF and increased the cortical actin ring structure (FIG. 3c).

Test Example 3

Figure 4A:
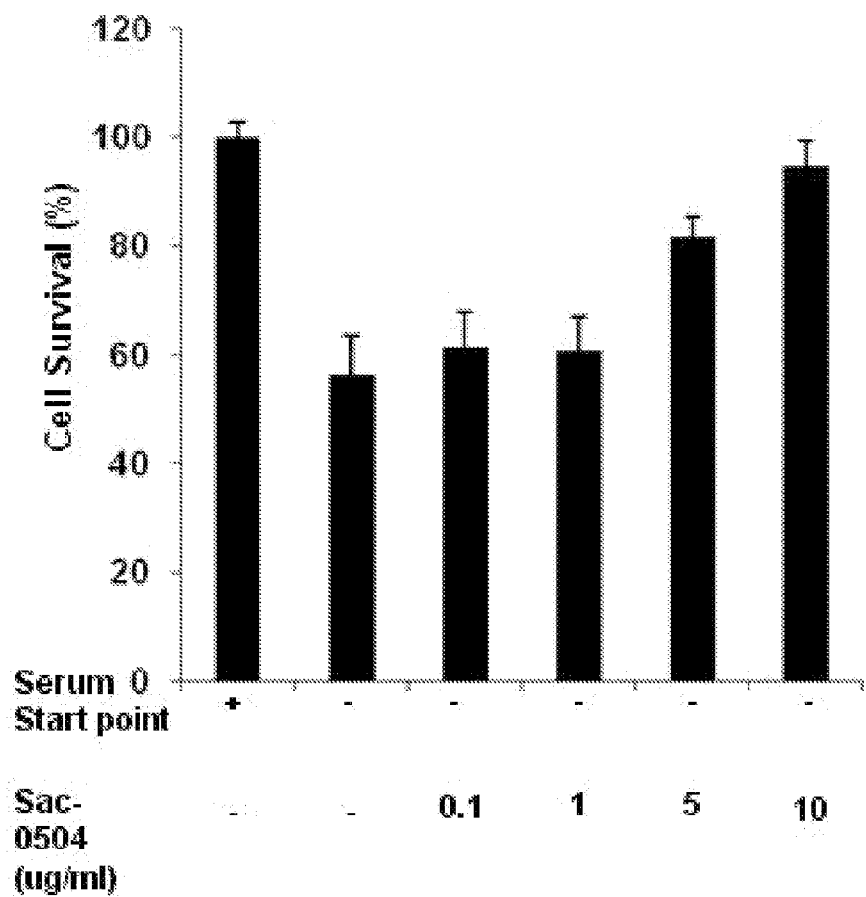
FIGS. 4*a*-4*b* and FIGS. 5*a*-5*c* show that Sac0601 and Sac0504 protect human retinal endothelial cells (HRECs) from serum depletion-induced apoptosis. HRECs ($3 \times 10^4$ cells/well) were seeded on a 24-well plate in M199 medium containing 20% fetal bovine serum. The next day, the cells were transferred to a medium containing 0.140 μg/mL Sac0601 (FIG. 4*a*) or 0.1-10 μg/mL Sac0504 (FIG. 4*b*). Cell viability was determined by MTT assay 48 hours later.
Figure 4B:
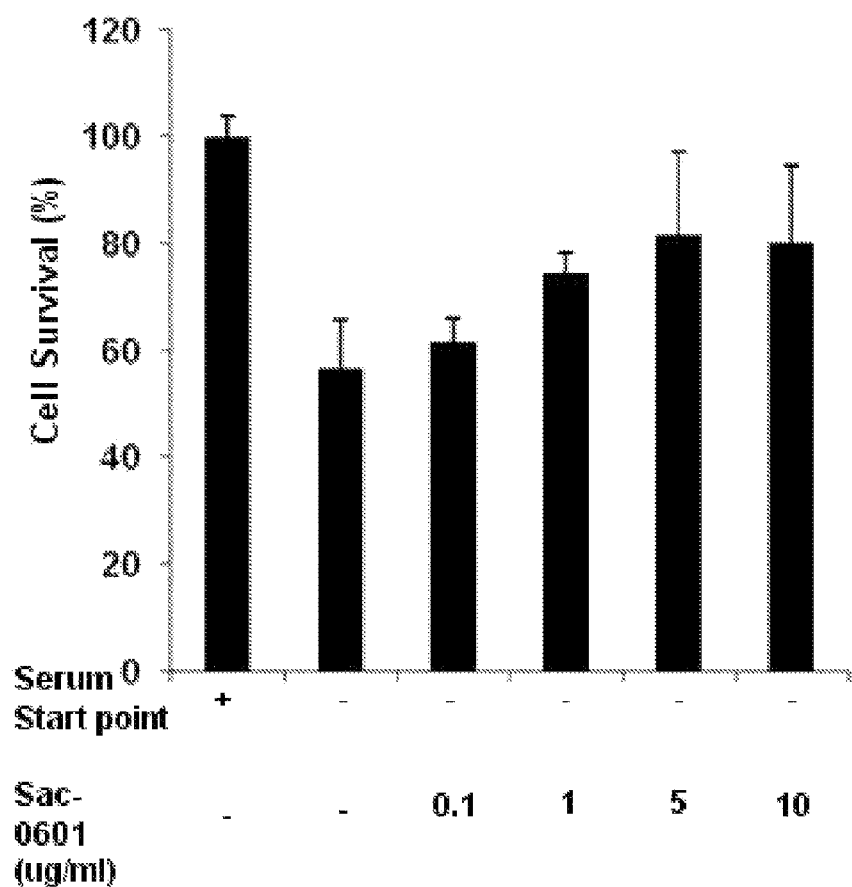
Figure 5A:
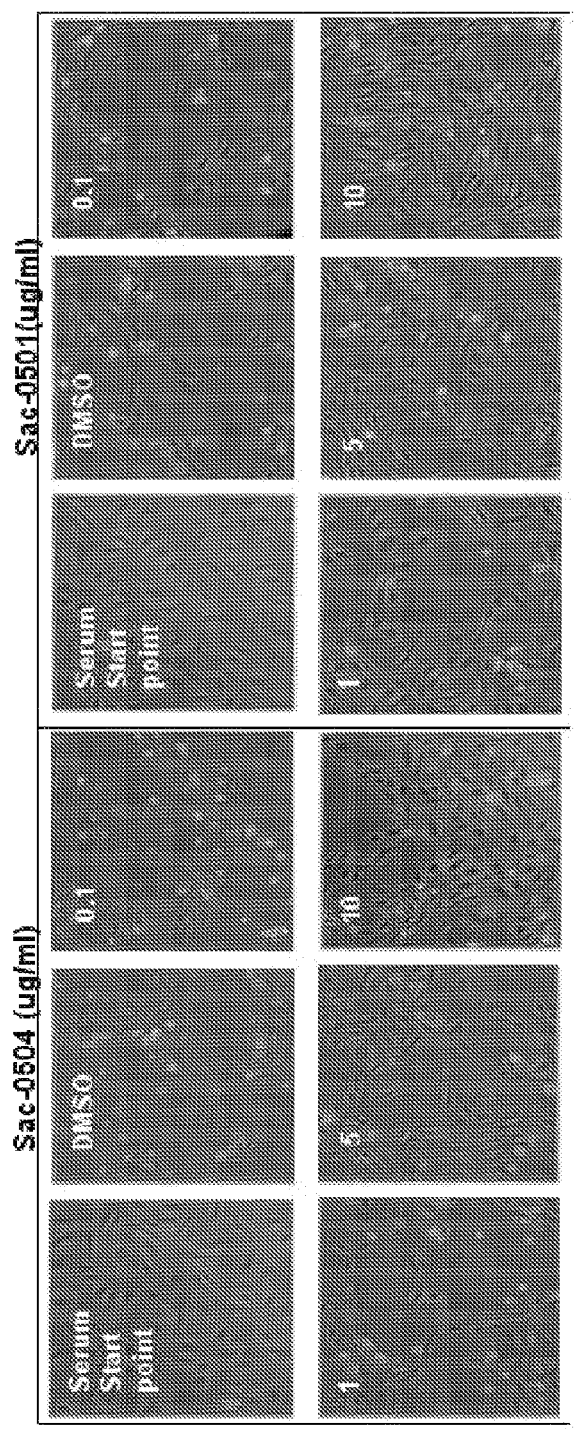

Ability of Inhibiting Apoptosis in HRECs and Change in Cytoskeleton of Synthesized Derivatives Among the 15 synthesized derivatives screened above, the two synthesized derivatives (Sac0504 and Sac0601) that were expected to exhibit superior ability of protecting HUVECs and inhibiting permeability were screened. Their ability of inhibiting apoptosis was confirmed again for HRECs. HRECs ($3 \times 10^4$ cells/well) were seeded on a 24-well plate in M199 medium (1 mL) containing 20% fetal bovine serum, Next day, the cells were transferred to serum-free M199 medium containing 0.1-10 µg/ml. Sac060.1 (FIG. 4a) or 0.1-10 µg; mL Sac0504 (FIG. 4b). Cell viability was determined by MTF assay in the same manner as in Test Example 1. As the result for the HUVECs, it was confirmed that both Sac0601 and Sac0504 have the ability of protecting the retinal vascular endothelial cells from apoptosis induced by the removal of serum (FIG. 4a-4b and FIG. 5a).

Figure 4D:
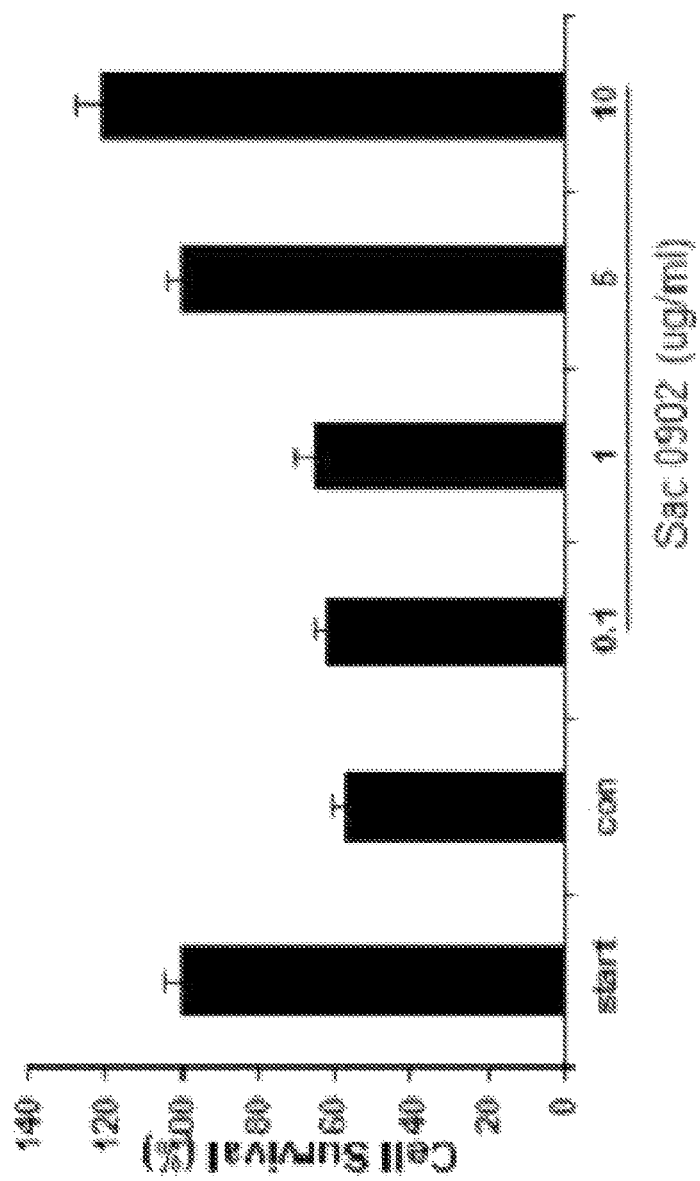
Figure 5B:
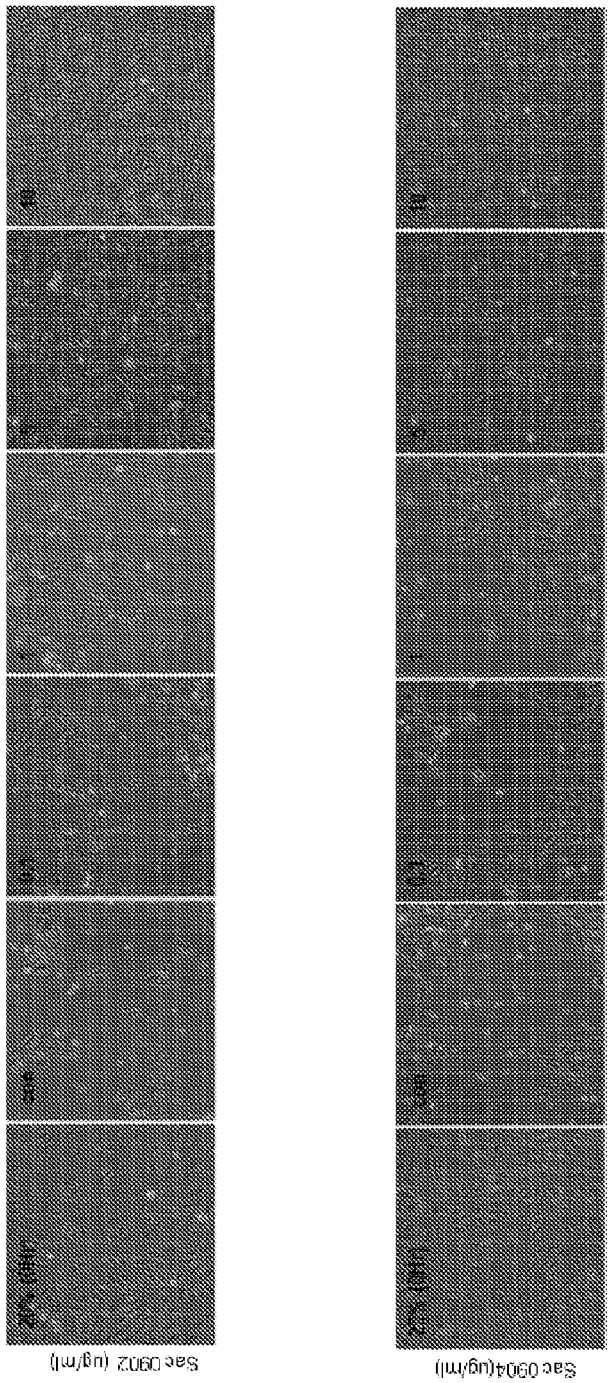
Figure 5C:
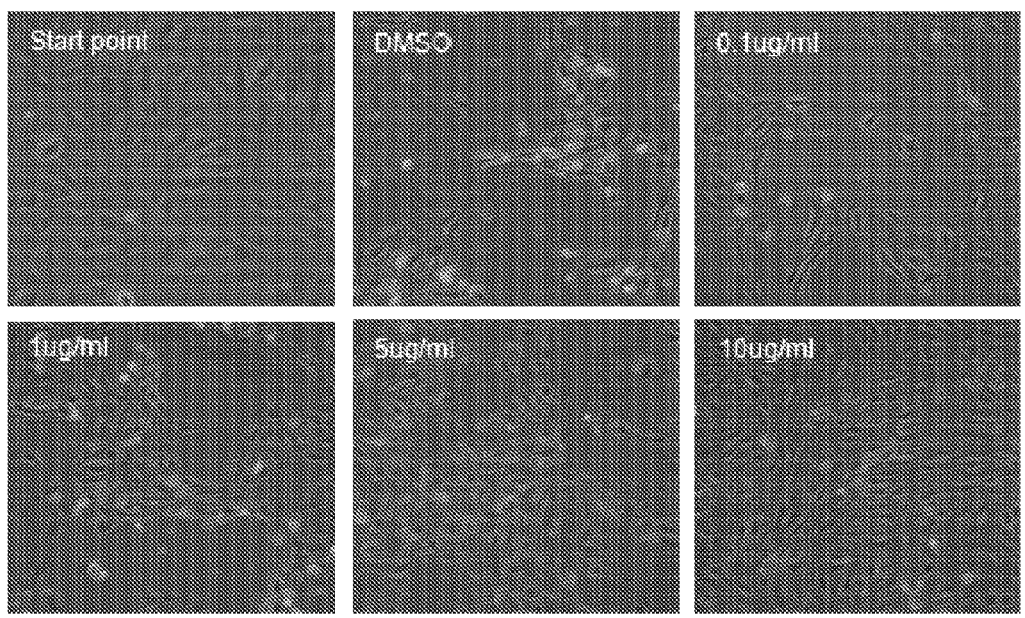

Also; among the 15 synthesized derivatives (Synthesis Example 5) screened above, the two synthesized derivatives (Sac0904 and Sac0902) that were expected to exhibit superior ability of protecting HUVECs and inhibiting permeability were screened. Their ability of inhibiting apoptosis was confirmed again for HRECs. Both Sac0904 and Sac0902 showed the ability of protecting the vascular endothelial cells from apoptosis induced by the removal of serum in a concentration-dependent manner (FIGS. 4c-4d and FIG. 5b). This suggests that both Sac0904 and Sac0902 protect the vascular endothelial cells in a concentration-dependent manner. The compounds synthesized in Synthesis Example 6; in particular Sac1004, also showed the ability of protecting the vascular endothelial cells from apoptosis induced by the removal of serum in a concentration-dependent manner (FIG. 4e and FIG. 5c).

Figure 6A:
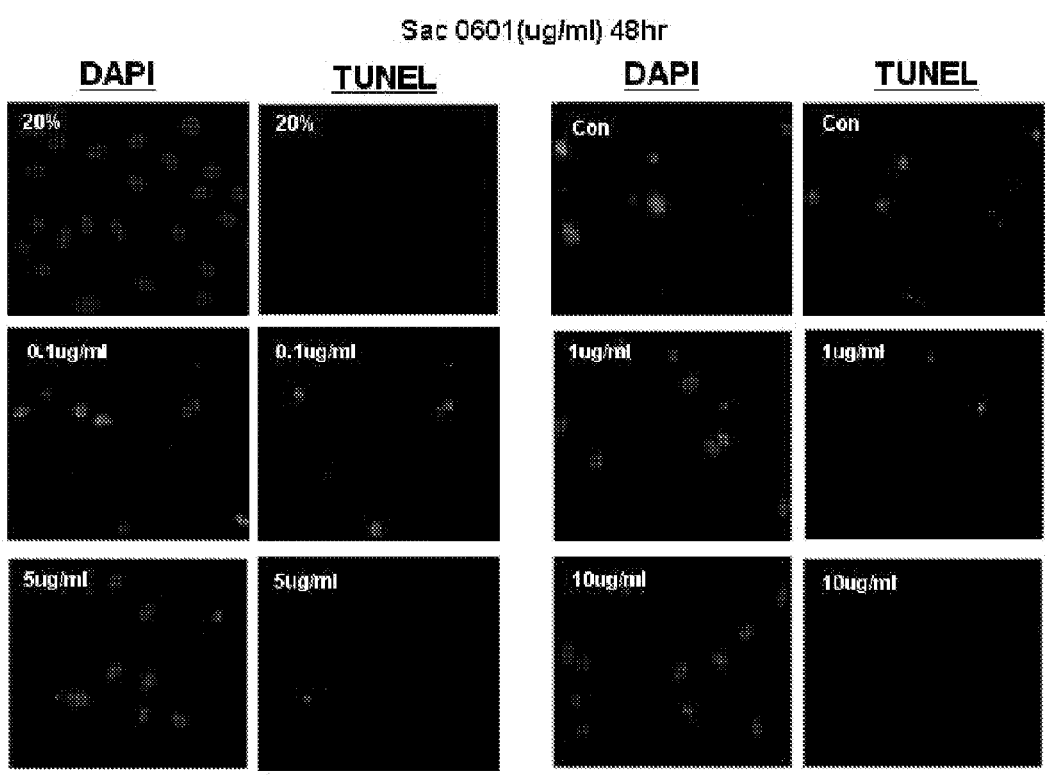
FIGS. 6*a*-6*b* show that Sac0601 and Sac0504 protect HRECs from serum depletion-induced apoptosis. HRECs ($3 \times 10^4$ cells/well) were seeded on a 24-well plate in M199 medium containing 20% fetal bovine serum. The next day, the cells were transferred to a medium containing 0.1-10 μg/mL Sac0601 (FIG. 6*a*) or 0.1-10 μg/mL Sac0504 (FIG. 6*b*). DNA fragmentation was analyzed by TUNEL assay 48 hours later.
Figure 6B:
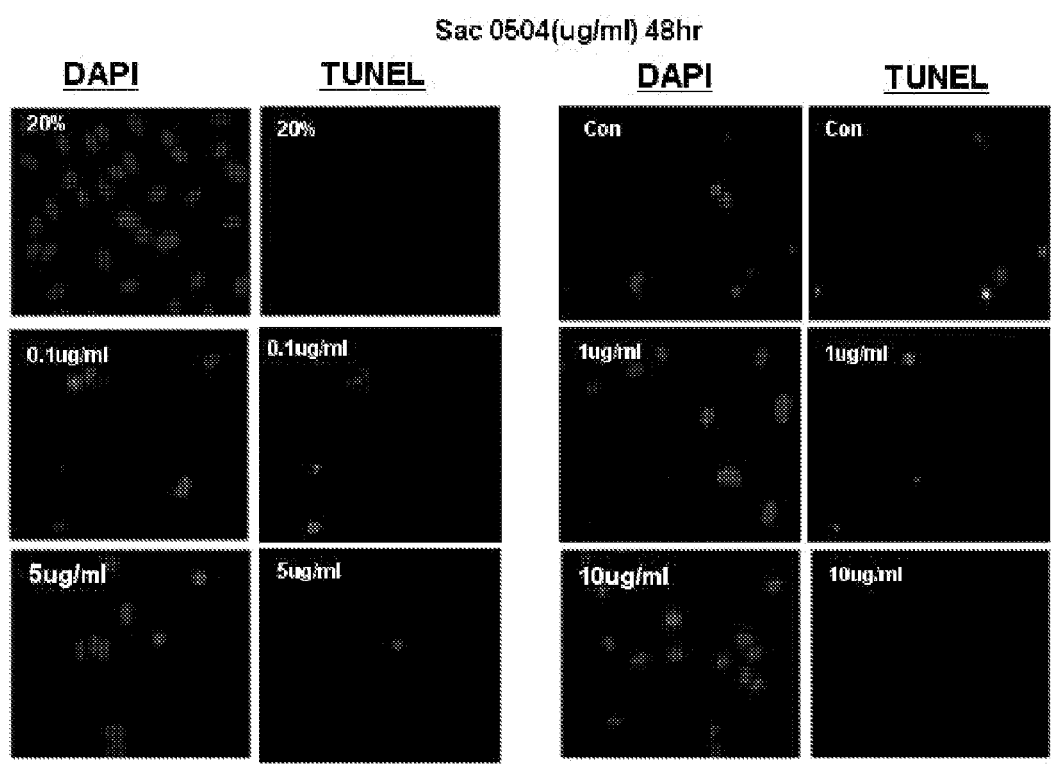

In addition, chromosomal fragmentation and nicking characteristic of apoptosis were monitored, HRECs ($3 \times 10^4$ cells/well) were seeded on a 24-well plate in M199 medium (1 mL) containing 20% fetal bovine serum, Next day, the cells were transferred to serum-free M199 medium containing 0.1-10 µg/mL Sac0601 (FIG. 6a) or 0.1-10 µg/mL Sac0504 (FIG. 6b). 48 hours later, the cells were washed twice with PBS, fixed with 2% paraformaldehyde, and washed twice with PBS again, After adding 4',6-diamidino-2-phenylindole-2HCl (DAPI; Calbiochem, USA) solution and reacting for 30 minutes in the dark, the cells were washed twice with PBS and degree of DNA fragmentation was observed under an optical microscope after covering with a cover glass. As a result, it was confirmed that Sac0601 and Sac0504 inhibit DNA fragmentation, suggesting that the ability of protecting the retinal vascular endothelial cells is through the inhibition of apoptosis (FIG. 6).

Figure 7A:
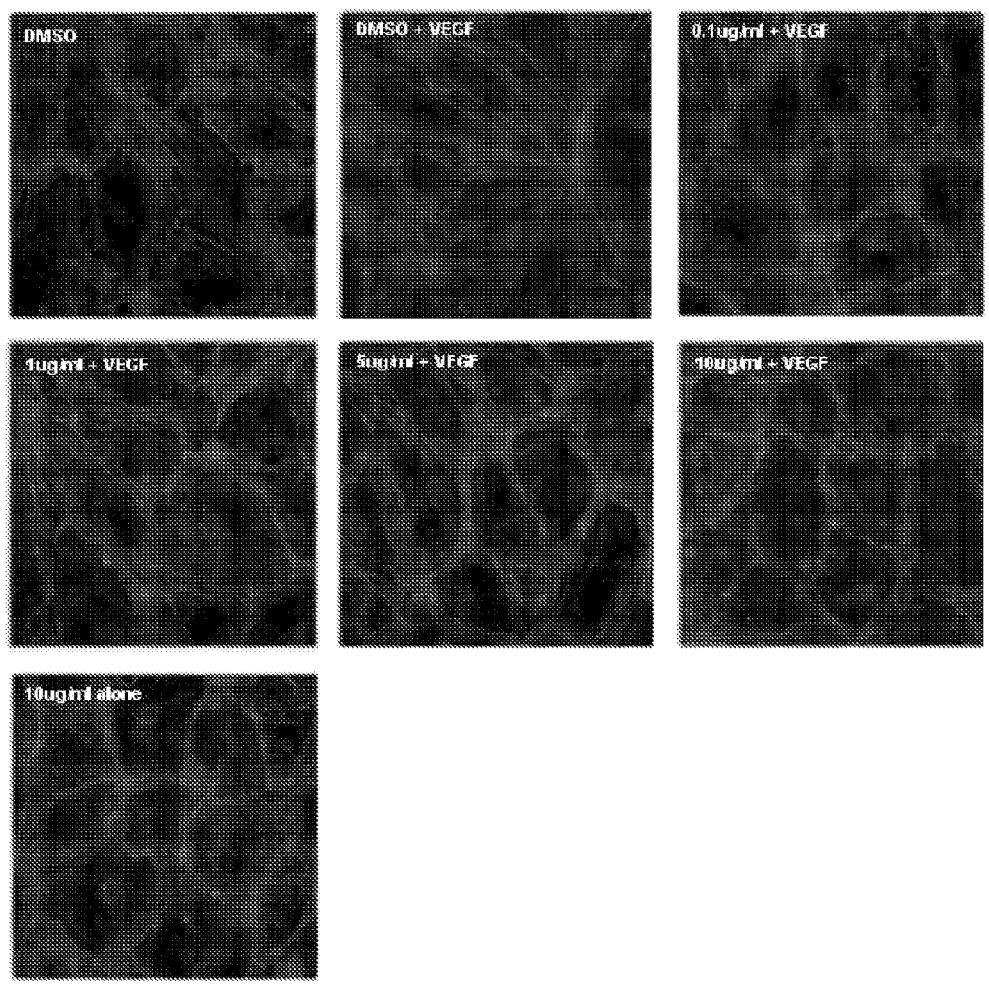
FIGS. 7*a*-7*b* show that the Rk1 analogs Sac0504 and Sac0601 inhibit the formation of actin stress fibers induced by VEGF and induce the formation of cortical actin ring structure. Confluent HUVECs were pretreated with the compounds (10 μg/mL) for 60 minutes before treating with 20 ng/mL VEGF (1 hr). The cells were then stained with rhodamine phalloidin.
Figure 7B:
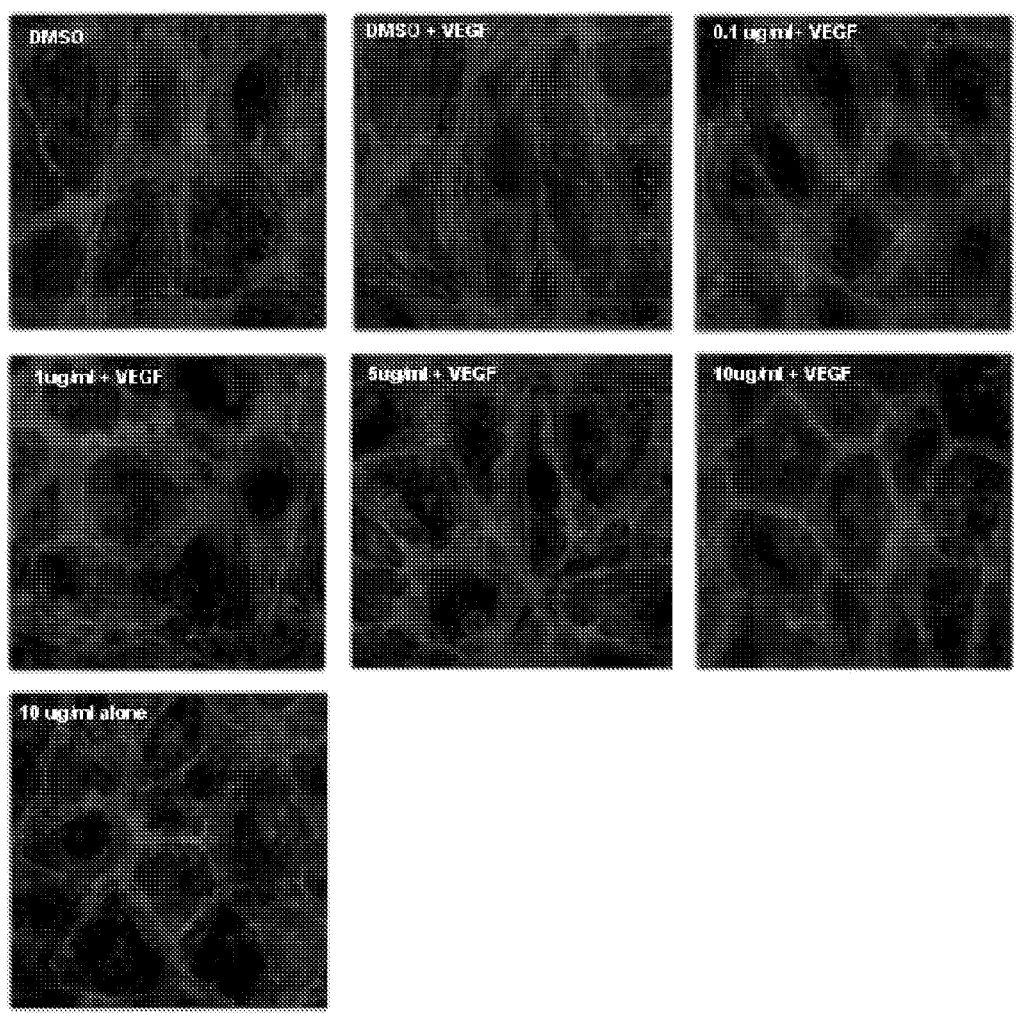
Figure 7C:
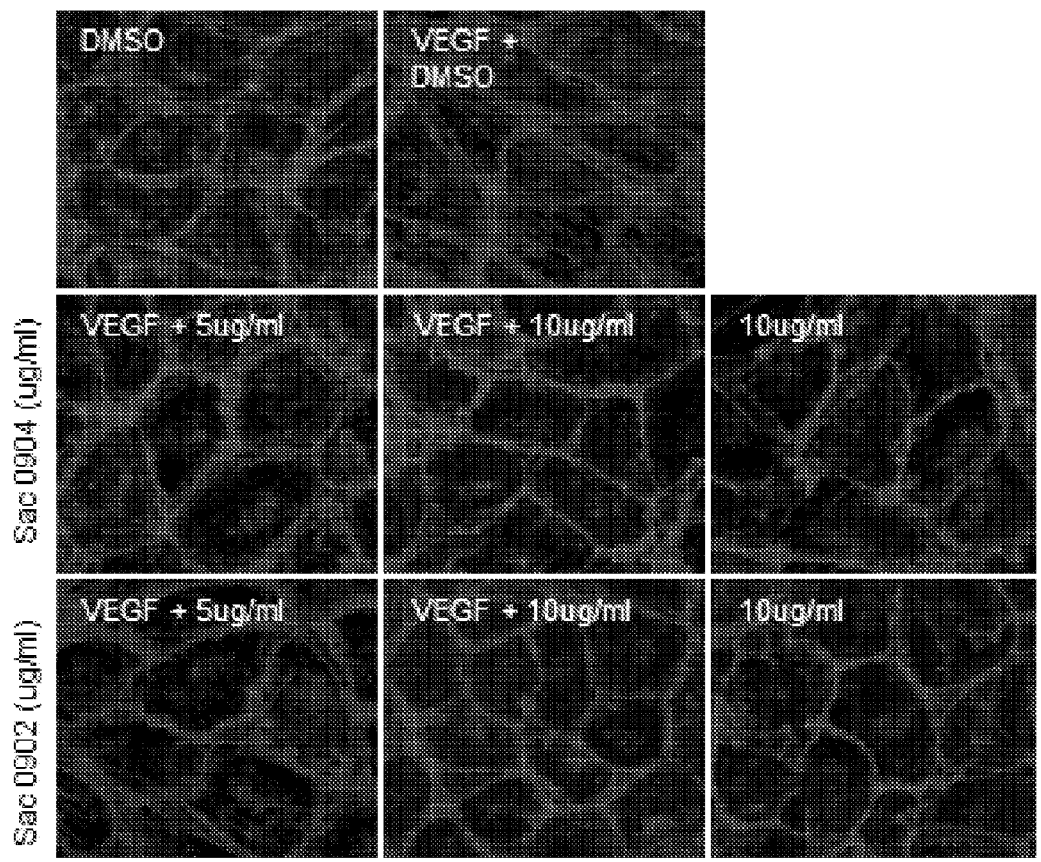
Figure 7D:
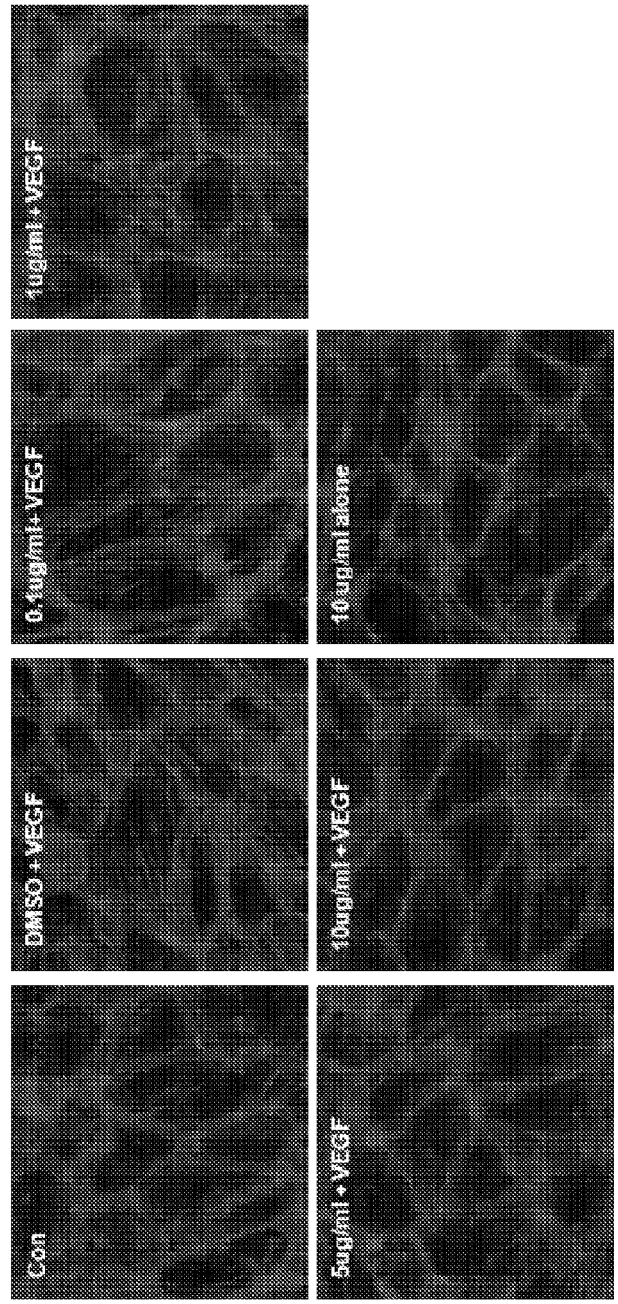

Confluent HRECs were treated with 10 µg/mL Sac0601 or Sac0504 for 1 hour and then with 20 ng/mL VEGF for 1 hour. Subsequently, the cells were fixed at room temperature for 20 minutes with 4% paraformaldehyde and washed 3 times with PBS (pH 7.4). Then, the cells were permeabilized with 0.1% Triton X-100/PBS and reacted with 0.1 mg/mL rhodamine phalloidin (Molecular Probes) for 1 hour. Then, the cells were observed under a fluorescence microscope (Olympus). As a result, Sac0601 and Sac0504 inhibited the formation of actin stress fibers induced by VEGF and, at the same time, increased the formation of cortical actin ring structures (FIG. 7a and FIG. 7b). The analysis of actin cytoskeleton was conducted also for the compounds synthesized in Synthesis Example 5. Both Sac0904 and Sac0902 exerted effects in a concentration-dependent manner on the actin cytoskeleton which is closely related with vascular permeability (FIG. 7c). Both Sac0904 and Sac0902 inhibited the formation of actin stress fibers and, at the same time, increased the formation of cortical actin ring structures (FIG. 7c). Also, Sac1004 prepared in Synthesis Example 6 inhibited the formation of actin stress fibers and increased the formation of cortical actin ring structures (FIG. 7d).

Test Example 4

Effect of Synthesized Derivatives on Stability of Tight Junctions (TJs) at Cell-Cell Contacts (a) Inhibition of Change in TJ Stability Induced by VEGF Vascular permeability is known to be greatly affected by the stability of Tas between vascular cells. According to the previous researches performed by the inventors, Rk1 inhibits permeability between vascular endothelial cells by increasing the stability of TJs at cell-cell contacts.

Confluent HRECs were treated with 10 µg/mL Sac0601 (FIG. 8a, panel A) or Sac0504 (FIG. 8a, panel B) for 1 hour and then with 20 ng/mL. VEGF for 1 hour. Subsequently, the cells were fixed at room temperature for 20 minutes with 4% paraformaldehyde and permeabilized with 0:1% Triton X-100/PBS. Then, the cells were incubated in PBS blocking solution containing 5% normal goat serum and 0.05% Tween-20. The cells were then reacted with anti-occludin antibody (Zymed Laboratories Inc.). The result was visualized with fluorescein-conjugated anti-mouse antibody (Vector Lab.). Also, western blotting was conducted for the cell lysate. The cell lysate was fractionated with SDS-PAGE and then transferred to polyvinyl difluoride membrane. The blocked membrane was reacted with anti-occludin antibody (Zymed Laboratories Inc.) and the immune response band was visualized with the chemiluminescence reagent obtained from Amersham Biosciences, Inc.

Figure 8A:
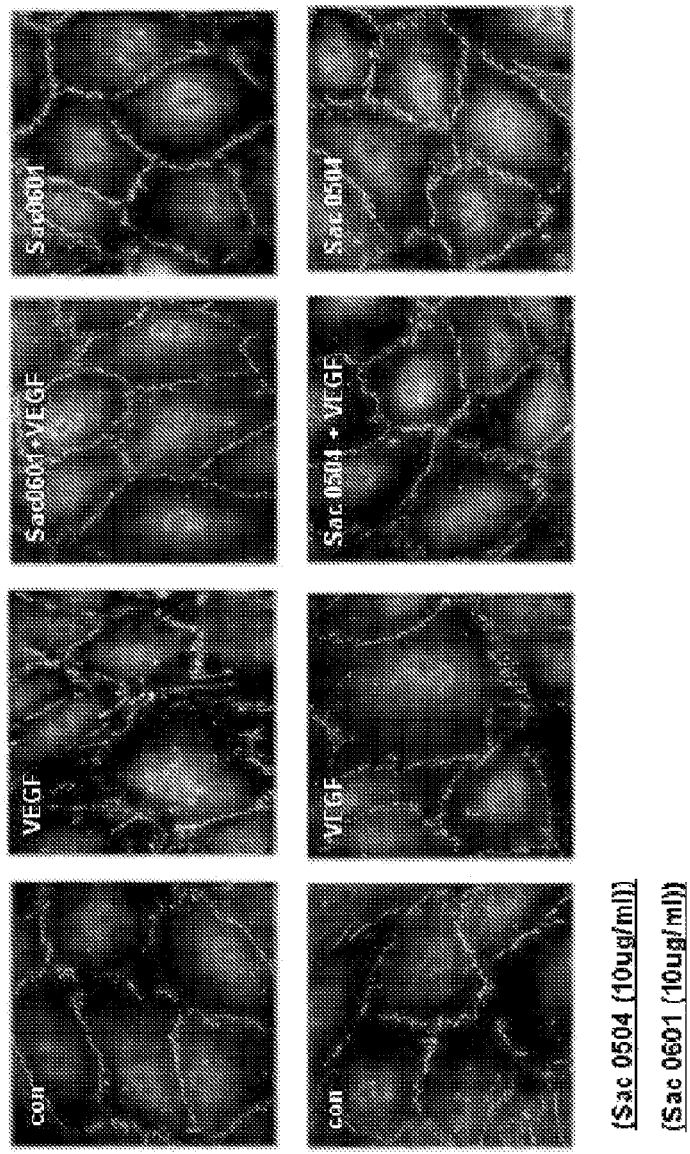
In FIG. 8*a*, confluent HRECs were pretreated with Sac0601 (panel A in FIG. 8*a*) or Sac0504 (panel B in FIG. 8*a*) for 60 minutes before treating with 20 ng/ml. VEGF (1 hr). The cells were then stained with occludin antibody.
Figure 8B:
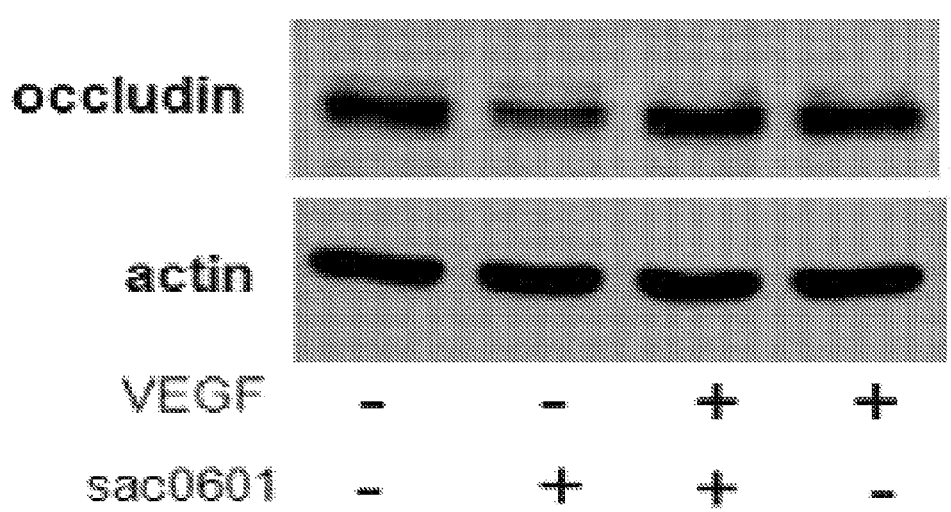
In FIG. 8*b*, confluent HRECs were pretreated with Sac0601 (10 μg/mL) for 60 minutes before treating with 20 ng/mL VEGF (1 hr). Then, cell lysate was subjected to western blotting using anti-occludin antibody.
Figure 8D:
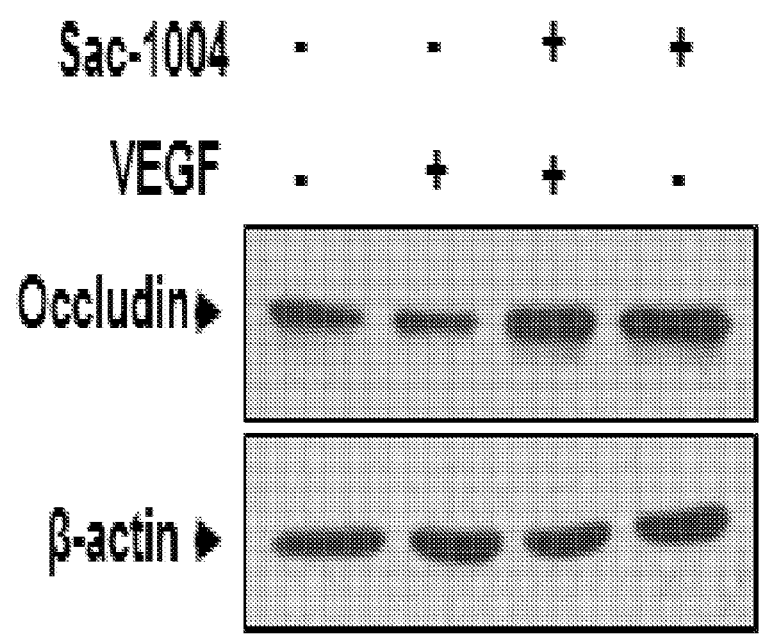

When the HRECs were treated with Sac0601 and Sac0504, the redistribution of TJs into the cytoplasm or its destabilizing at the cell membrane induced by VEGF could be inhibited as for Rk1. In addition, it was confirmed that the stability of TJs between cells is enhanced Sac0601 and Sac0504. It was found that Sac0601 is more effective in enhancing the stability of TJs than Sac0504, Immunostaining revealed that occludin, the representative protein constituting the TJ, is more stably located at the cell-cell contacts by the two compounds (FIG. 8a). Western blotting revealed that treatment with Sac0601 results in decrease of occludin (FIG. 8b). When the HRECs were pretreated with Sac1004, the redistribution of TJs into the cytoplasm or its destabilizing at the cell membrane induced by VEGF could be inhibited and, in addition, the stability of TJs between cells was improved (FIG. 8c). Also, it was confirmed that Sac1004 restores the activity of occludin decreased by VEGF (FIG. 8d).

(b) Restoration of TJ Instability and Change of Cytoskeleton Induced by VEGF

Figure 9A:
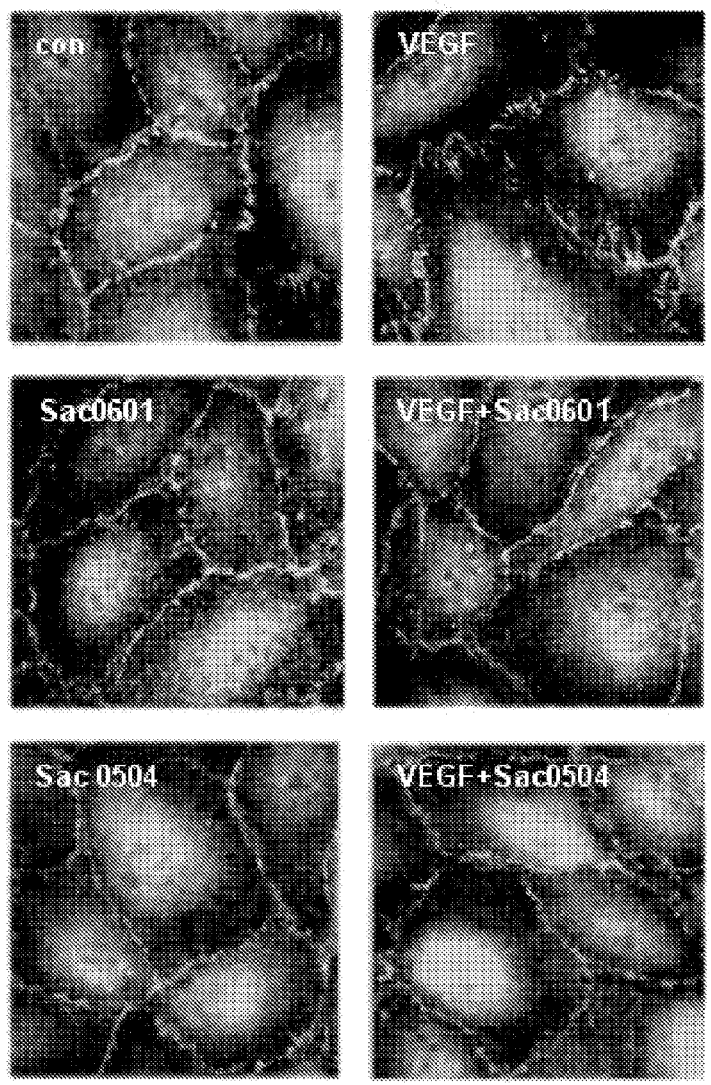
In FIGS. 9*a*-9*b*, confluent HRECs were stimulated with 20 ng/mL VEGF (1 hr) before treating with Sac0504 and Sac0601. The cells were then stained with anti-occludin antibody (FIG. 9*a*) and rhodamine phalloidin (FIG. 9*b*).
Figure 9B:
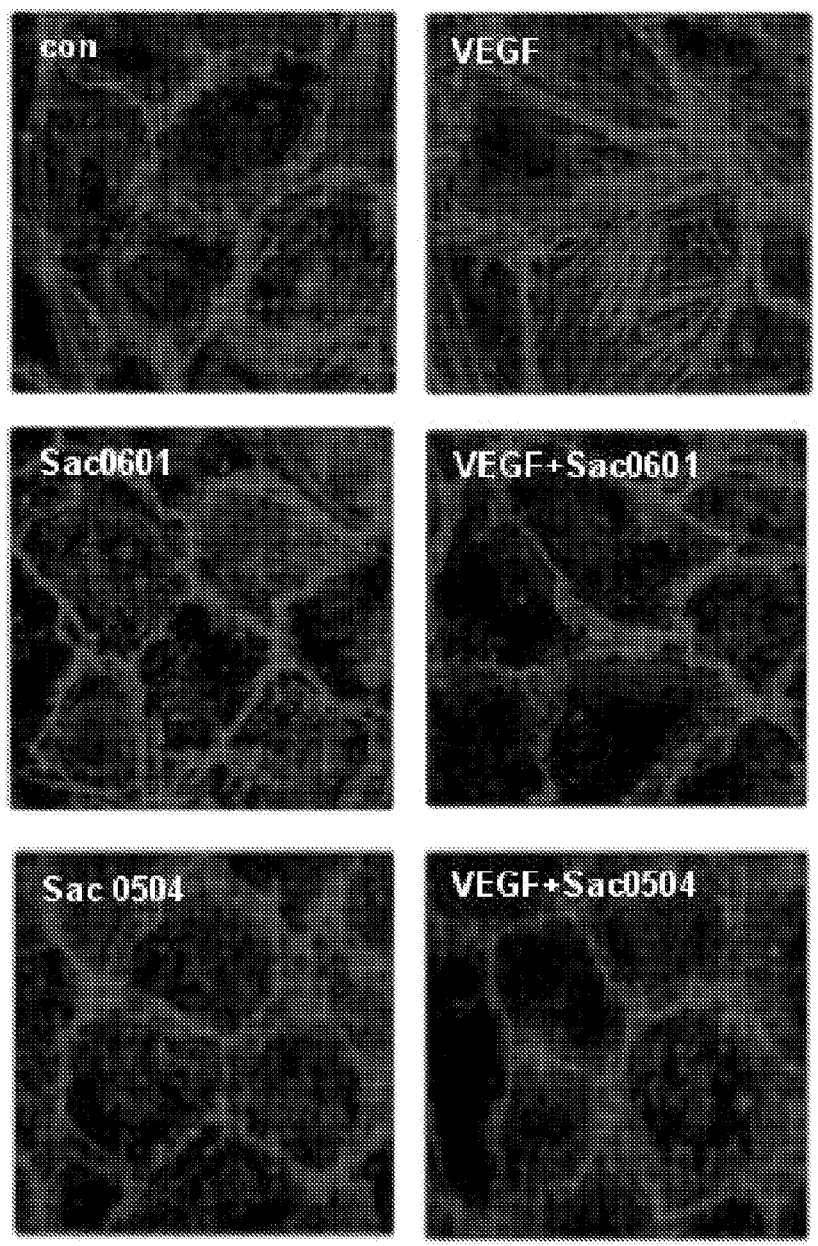

Confluent HRECs were treated with 20 ng/mL. VEGF for 1 hour and then with 10 µg/mL Sac0601 or Sac0504 for 1 hour. Subsequently, the cells were stained with anti-occludin antibody (FIG. 9a) or anti-actin antibody (FIG. 9b) as described above. As a result, it was confirmed that the change in actin structure and TJ stability at the cell-cell contacts induced by VEGF can be restored by Sac0601 and Sac0504.

Test Example 5

Figure 10A:
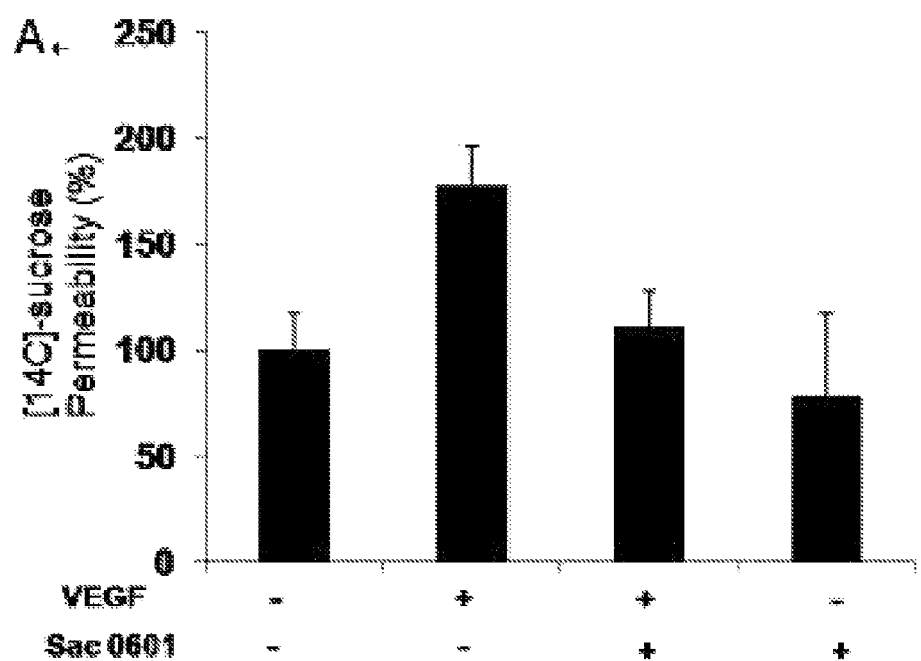
FIGS. 10*a*-10*b* show that Sac0601 (FIG. 10*a*) and Sac0504 (FIG. 10*b*) inhibit the permeability of retinal endothelial cells induced by VEGF. HRECs were seeded on a transwell filter. After reaching confluency, the cells were pretreated with Sac0601 (FIG. 10*a*) and Sac0504 (FIG. 10*b*) for 60 minutes before treating with 20 ng/ml. VEGF (1 hr). The permeability of HRECs was determined by measuring radiation of [$^{14}$C] sucrose (1 μCi/μL) diffused below the transwell using a liquid scintillation counter.
Figure 10B:
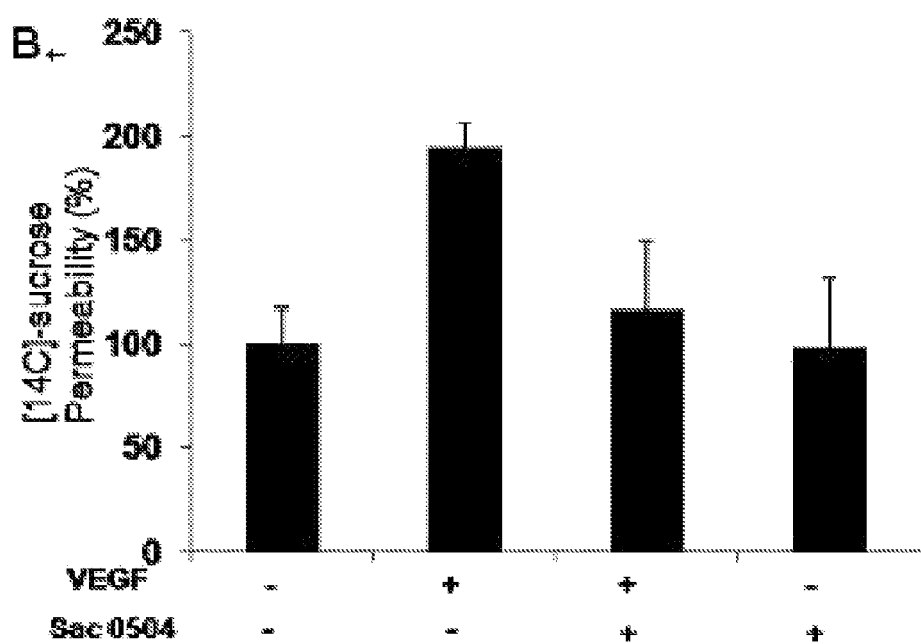
Figure 10C:
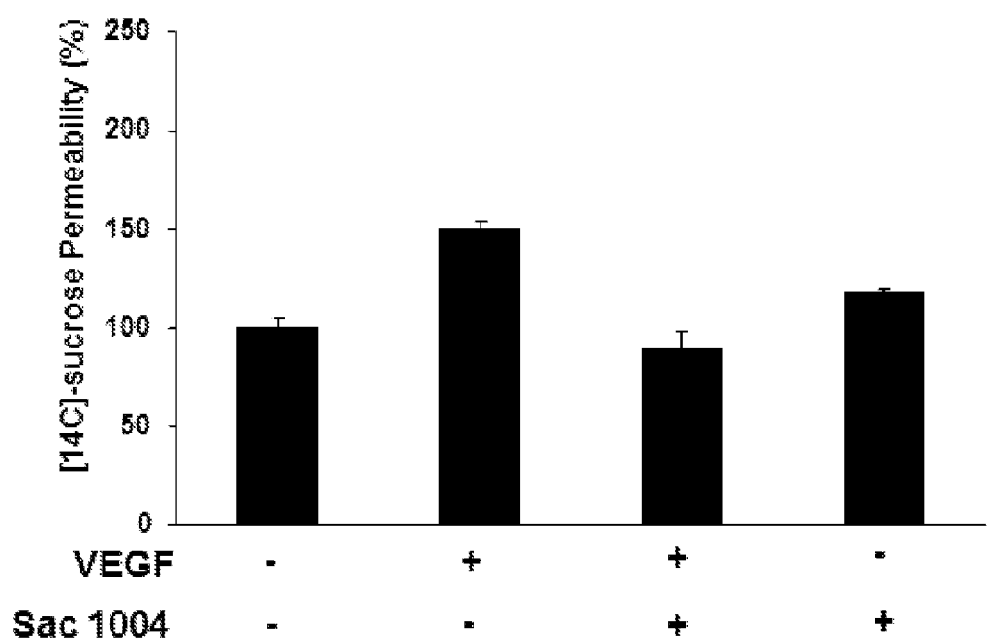

Inhibition of Permeability of Vascular Endothelial Cells by Synthesized Derivatives The effect of Sac0601 and Sac0504 on vascular permeability was analyzed. HRECs were seeded on a transwell filter (Corning Costar). After reaching confluency, the cells were cultured in M199 medium containing 1% FBS for 3 hours and treated with 10 μg/mL. Sac0601 (FIG. 10a) or Sac0504 (FIG. 10b) for 60 minutes, with or without pretreatment with 20 ng/mL VEGF for 60 minutes. Then, [$^3$H]sucrose (1 μCi [0.037 MBq.]/μL or 50 μL (0.8 μCi [0.0296 MBq])/mL, Amersham Pharmacia) were added. 30 minutes later, radiation diffused below the transwell was measured using a liquid scintillation counter (Wallac, PerkinElmer). Measurement was made at least four locations. As a result, it was confirmed that both the compounds maintain retinal vascular integrity by inhibiting permeability of the vascular endothelial cells and protect the cells from increase of vascular endothelial permeability induced by VEGF (FIG. 10a and FIG. 10b). Also, it was confirmed that Sac1004 maintains retinal vascular integrity by inhibiting permeability of the vascular endothelial cells and protect the cells from increase of vascular endothelial permeability induced by VEGF (FIG. 10c).

Test Example 6

Figure 11A:
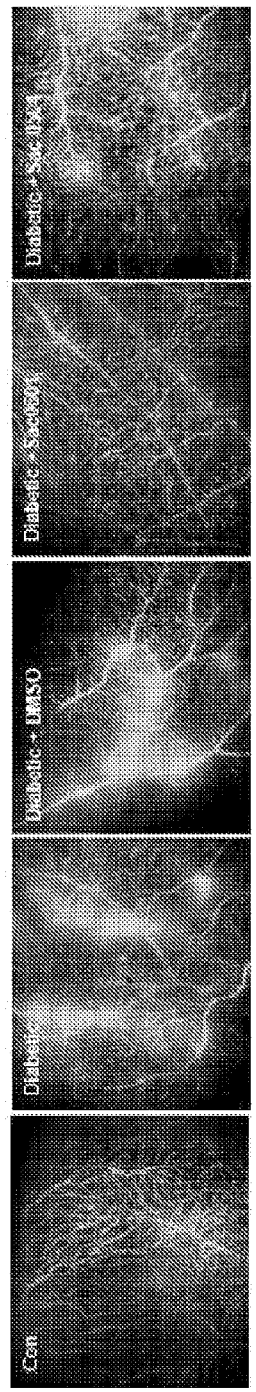
FIGS. 11*a*-11*b* show that Sac0601 completely inhibits and Sac0504 partially inhibits retinal vascular leakage in a diabetic mouse model. 10 μg of Sac0601 or 10 μg of Sac0504 was injected into the vitreous body of one eye of a diabetic mouse. 24 hours after the injection, 100 μL of FITC-dextran (30 mg/mL in filtered DVV) was injected into the left ventricle. Then, the retina was observed under an optical microscope (FIG. 11*a*) and the fluorescence intensity was quantified (FIG. 11*b*).
Figure 11B:
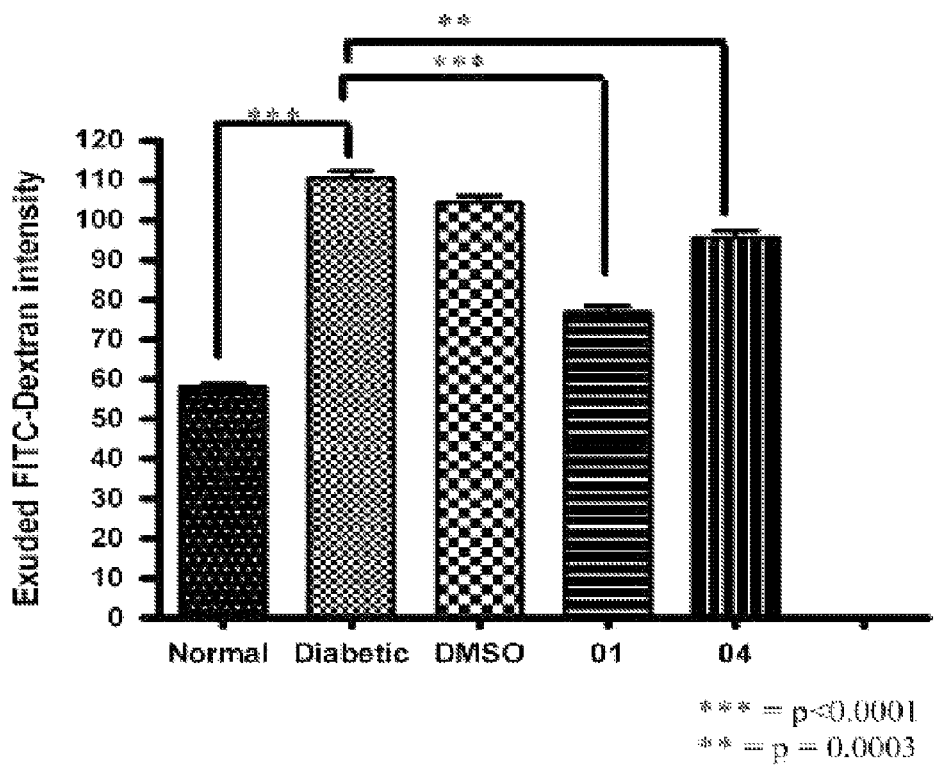
Figure 11C:
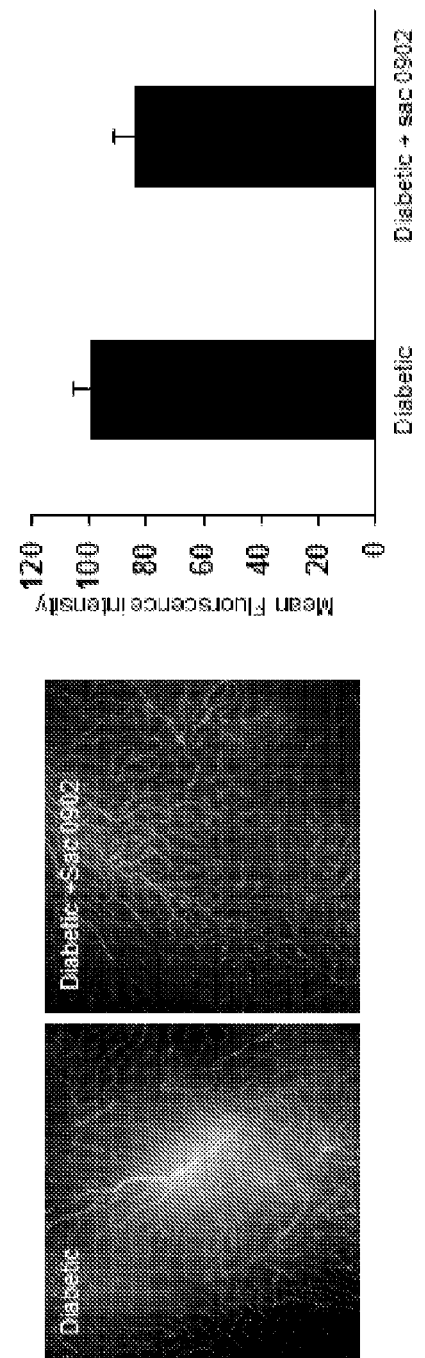
Figure 11D:
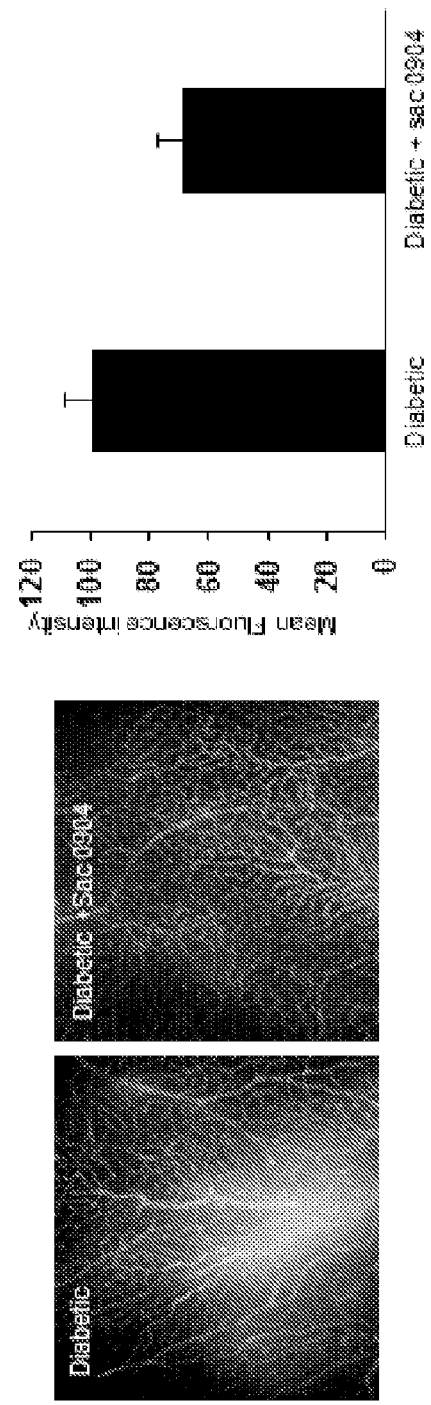
Figure 11E:
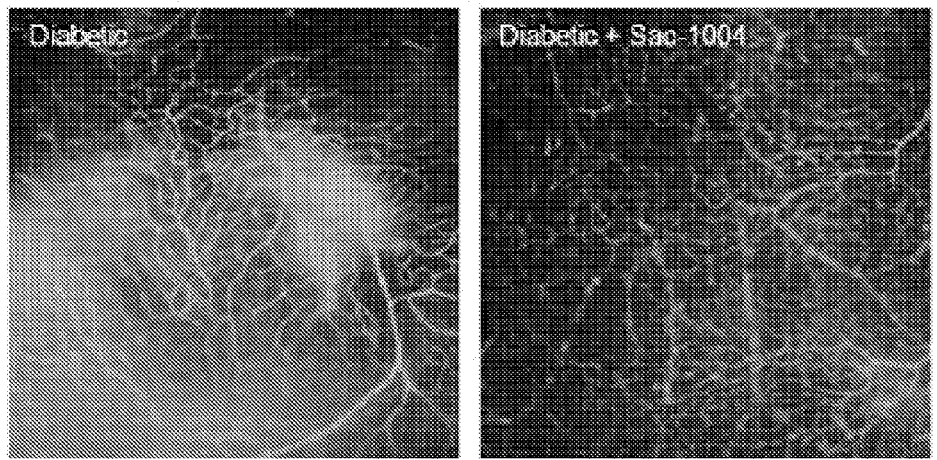
Figure 11F:
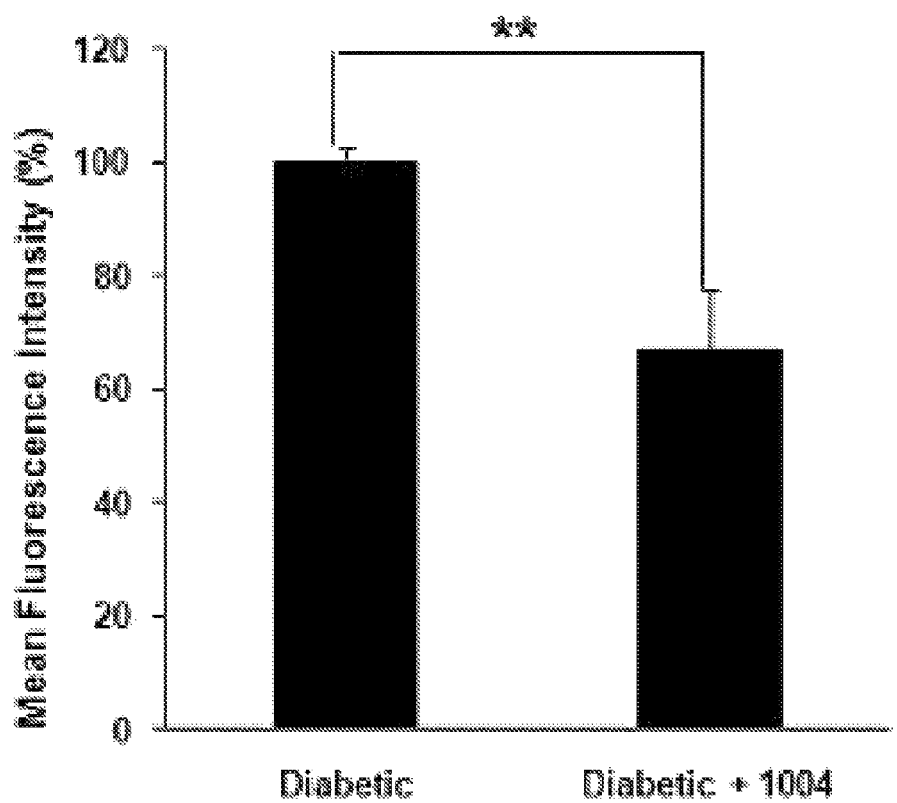

Effect of Synthesized Derivatives on Increased Vascular Permeability in Diabetic Retinopathy For in vivo analysis of the effect of the synthesized Rk1 derivatives on increased vascular permeability in diabetic retinopathy, a diabetic mouse (DM) model was made by injecting streptozotocin to C57/BL6 mouse. Sac 0601 or Sac 0504 (10 μg) was injected into the vitreous body of the mouse. 24 hours later, 40-kDa FITC-dextran (30 mg/mL in PBS, Sigma) was injected into the left ventricle. After waiting for about 2 minutes for circulation of the tracer, the eyes were taken out and fixed immediately in 4% PFA. Then, the retina was taken out and observed under an optical microscope. As seen from FIGS. 11a and 11b, it was confirmed that Sac0601 inhibits the retinal vascular permeability induced in the DM very effectively, whereas Sac0504 inhibits retinal vascular permeability only limitedly. Also, it was confirmed that Sac0904 synthesized in Synthesis Example 5 inhibits the retinal vascular permeability induced in the DM very effectively, whereas Sac0902 inhibits retinal vascular permeability only limitedly (FIG. 11c and FIG. 11d). And, as seen from FIG. 11e and FIG. 11f, Sac1004 synthesized in Synthesis Example 6 inhibits the retinal vascular permeability induced in the DM very effectively.

Test Example 7

Inhibition of Vascular Leakage Induced by VEGF by Synthesized Derivatives (Animal Experiment)

Figure 12A:
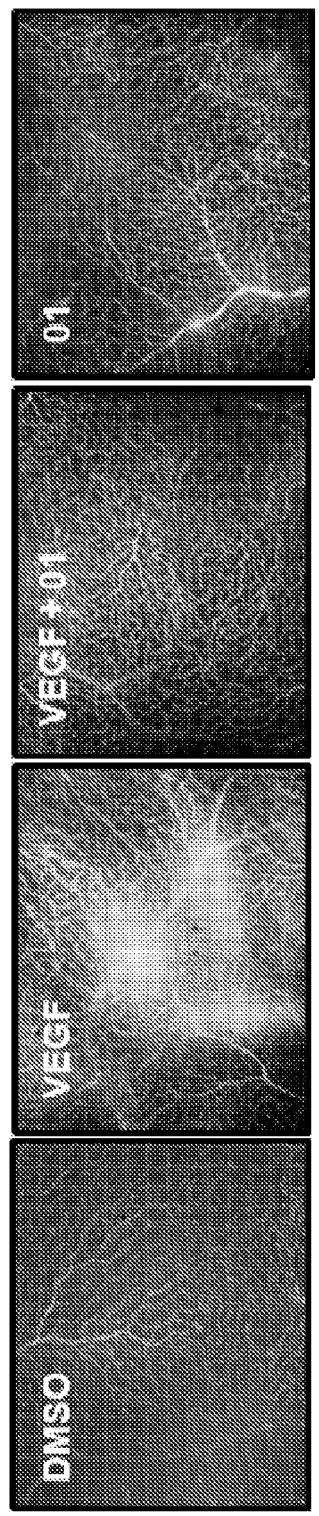
FIG. 12*a*-12*b* show that Sac0601 greatly reduces vascular leakage induced by VEGF in mouse. 01 denotes Sac0601.
Figure 12B:
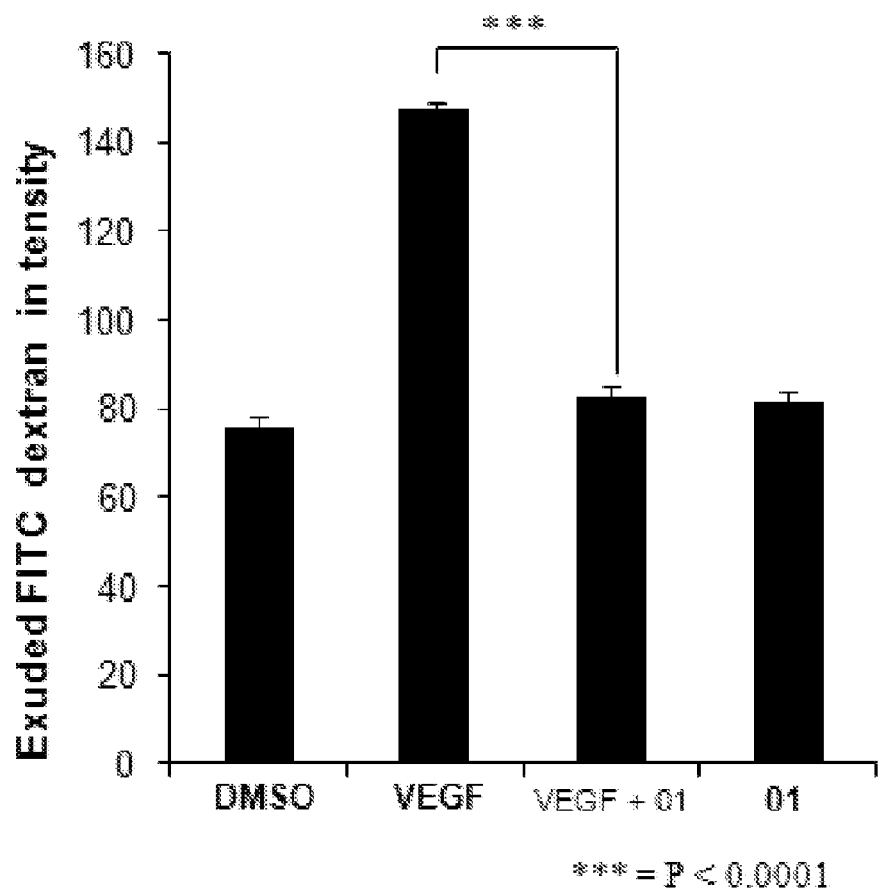

VEGF (50 ng) and Sac0601 (10 μg) were injected into the vitreous body of C57/BL6 mouse. An excipient (DMSO) was injected into the other eye. 24 hours after the injection, 100 μL FITC-dextran (30 mg/mL in PBS, Sigma) was injected into the left ventricle. After waiting for about 2 minutes for circulation of the tracer, the eyes were taken out and fixed immediately in 4% PFA, Then, the retina was taken out and observed under an optical microscope. As seen from FIGS. 12a and 12b, Sac0601 greatly decreases the vascular leakage induced by VEGF.

Those skilled in the art will appreciate that the conceptions and specific embodiments disclosed in the foregoing description may be readily utilized as a basis for modifying or designing other embodiments for carrying out the same purposes of the present disclosure. Those skilled in the art will also appreciate that such equivalent embodiments do not depart from the spirit and scope of the disclosure as set forth in the appended claims.

REFERENCES

1. Erickson K K, Sundstrom J M, Antonetti D A. Vascular permeability in ocular disease and the role of tight junctions. *Angiogenesis* 2007; 10(2): 10347,
2. Maniatis N A, Orfanos S E. The endothelium in acute lung injury/acute respiratory distress syndrome. *Curr Opin Crit Care* 2008 February; 14(1): 22-30,
3. Harhaj N S, Antonetti D A. Regulation of tight junctions and loss of barrier function in pathophysiology. *Int J Biochem Cell Biol,* 2004 July; 36(7): 1206-37,
4. Vandenbroucke E, Mehta D, Minshall R, Malik A B. Regulation of endothelial junctional permeability, *Ann N Y Acad Sci.* 2008 March; 1123: 134-45.
5. Cordenonsi M, D'Atri F, Hammar E, et al. Cingulin contains globular and coiled-coil domains and interacts with ZO-1, ZO-2, ZO-3, and myosin. *J Cell Biol.* 1999 Dec. 27; 147(7): 1569-82.
6. Haskins J, Gu L, Wittchen E S, Hibbard J, Stevenson B R. ZO-3, a novel member of the MAGUK protein family found at the tight junction, interacts with ZO-1 and occludin. *J Cell Biol.* 1998 Apr. 6; 141(1): 199-208.
7. Itoh M, Furuse M, Morita K, Kubota K, Saitou M, Tsukita S. Direct binding of three tight junction-associated MAGUKs, ZO-1, ZO-2, and ZO-3, with the COOH termini of claudins. *J Cell Biol.* 1999 Dec. 13; 147(6): 1351-63.
8. Madara J L. Regulation of the movement of solutes across tight junctions. *Annu Rev Physiol.* 1998; 60: 143-59.
9, Anderson J M, Van Itallie C M. Tight junctions and the molecular basis for regulation of paracellular permeability. *Am J Physiol.* 1995 October; 269(4 Pt 1): G467-75.
10. Mehta D, Malik A B. Signaling mechanisms regulating endothelial permeability. *Physiol Rev.* 2006: January; 86(1): 279-367.
11. McVerry B J, Garcia J G. Endothelial cell barrier regulation by sphingosine 1-phosphate. *J Cell Biochem.* 2004 Aug. 15; 92(6): 1075-85.
12. Garda J G, Liu F, Verin A D, et al. Sphingosine 1-phosphate promotes endothelial cell barrier integrity by Edg-dependent cytoskeletal rearrangement. *J Clin Invest* 2001 September; 108(5): 689-701,
13. Dudek S M, Jacobson J R, Chiang E T, et al. Pulmonary endothelial cell barrier enhancement by sphingosine 1-phosphate: roles for cortactin and myosin light chain kinase. *J Biol Chem.* 2004 Jun. 4; 279(23): 24692-700,
14. Weed S A, Parsons J T. Cortactin: coupling membrane dynamics to cortical actin assembly. *Oncogene,* 2001 Oct. 1; 20(44): 6418-34,
15. Sacha E. Diabetic retinopathy. Current opinion on pathophysiology, diagnostics and therapy, *Przegl Lek.* 2005; 62(4): 238-42.
16. Frank R N. Diabetic retinopathy. N Engl J Med 2004 January: 1; 350(1): 48-58.
17. Gariano R F, Gardner T W. Retinal angiogenesis in development and disease. *Nature.* 2005 December: 15; 438(7070): 960-6.
18. Murata T, Ishibashi T, Khalil A, Hata Y, Yoshikawa H, Inomata H. Vascular endothelial growth factor plays a role in hyperpermeability of diabetic retinal vessels. *Ophthalmic Res.* 1995; 27(1): 48-52.
19. Weis S M, Cheresh D. A. Pathophysiological consequences of VEGF-induced vascular permeability. *Nature.* 2005 Sep. 22; 437(7058): 497-504.

20. Kiefer D, Pantuso T. *Panax ginseng. Am Fam Physician.* 2003 Oct. 15; 68(8): 1539-42.
21. Lee T K, Johnke R M, Allison R R, O'Brien K F, Dobbs L J, Jr. Radioprotective potential of ginseng, *Mutagenesis,* 2005 July; 20(4): 237-43.
22. Kwon S W, Han S B, Park I H, Kim J M, Park M K, Park J H. Liquid chromatographic determination of less polar ginsenosides in processed ginseng. *J Chromatogr A.* 2001 Jul. 6; 921(2): 335-9.
23. Keum Y S, Park K K, Lee J M, et al. Antioxidant and anti-tumor promoting activities of the methanol extract of heat-processed ginseng, *Cancer Lett.* 2000 Mar. 13; 150 (1): 41-8.
24. Brownlee M, Cerami A, Vlassara H. Advanced glycosylation end products in tissue and the biochemical basis of diabetic complications. *N Engl J Med.* 1988 May 19; 318 (20): 1315-21.
25. Bonnardel-Phu E, Wartier J L, Schmidt A M, Avila C, Vicaut E. Acute modulation of albumin microvascular leakage by advanced glycation end products in microcirculation of diabetic rats in vivo. *Diabetes.* 1999 October; 48(10): 2052-8.
26. Wojciak-Stothard B, Ridley A J. Rho GTPases and the regulation of endothelial permeability, *Vascul Pharmacol.* 2002 November; 39(4-5): δ 1.87-99.
27. Miki H, Yamaguchi H, Suetsugu S, Takenawa T. IRSp53 is an essential intermediate between Rac and WAVE in the regulation of membrane ruffling. *Nature* 2000 Dec. 7; 408 (6813): 732-5,
28. Wu N Z, Baldwin A L. Transient venular permeability increase and endothelial gap formation induced by histamine. *Am J Physiol.* 1992 April; 262(4 Pt 2): H1238-47.
29. Ehringer W D, Edwards M J, Miller F N. Mechanisms of alpha-thrombin, histamine, and bradykinin induced endothelial permeability. *J Cell Physiol.* 1996 June; 167(3): 562-9.
30. Wojciak-Stothard B, Potempa S, Eichholtz T, Ridley A J. Rho and Rac but not Cdc42 regulate endothelial cell permeability. *J Cell Sci.* 2001 April; 1.1.4(Pt. 7): 1343-55.
31. Yun T K. Experimental and epidemiological evidence on non-organ specific cancer preventive effect of Korean ginseng and identification of active compounds. Mutat Res, 2003 February-March; 523-524: 63-74.
32. Sengupta S, Toh S A, Sellers L A, et al. Modulating angiogenesis: the yin and the yang in ginseng. *Circulation.* 2004 Sep. 7; 110(10): 1219-25.
33. Yue P Y, Wong D Y, Wu P K, et al. The angiosuppressive effects of 20(R)— ginsenoside Rg3. *Biochem Pharmacol.* 2006 Aug. 14; 72(4): 437-45.
34. Sato K, Mochizuki M, Saiki I, Yoo Y C, Samukawa K, Azuma I. Inhibition of tumor angiogenesis and metastasis by a saponin of *Panax ginseng*(ginsenoside-Rb2. *Biol Pharm Bull.* 1994 May; 17(5): 635-9.
35. Leung K W; et al. Ginsenoside Rb1 inhibits tube-like structure formation of endothelial cells by regulating pigment epithelium-derived factor through the oestrogen beta receptor. *Br. J Pharmacol.* 2007 September; 152(2): 207-15.
36. Min J K, Kim J H, Cho Y L, et al. 20(S)-Ginsenoside Rg3 prevents endothelial cell apoptosis via inhibition of a mitochondrial caspase pathway. *Biochem Biophys Res Commun.* 2006 Oct. 27; 349(3): 987-94.
37. Papapetropoulos A. A ginseng-derived oestrogen receptor beta (ERbeta) agonist, Rb1 ginsenoside, attenuates capillary morphogenesis. *Br J Pharmacol.* 2007 September; 152(2): 172-4.
38. Michel C C, Curry F E, *Physiol Rev.* 1999 July; 79(3): 703-61.
39. Dudek S M, Garcia J G. cytoskeletal regulation of pulmonary vascular permeability. *J Appl Physiol.* 2001 October; 91(4): 1487-500,
40. Garcia J G, Siflinger-Birnboim A, Bizios R, Del Vecchio P J, Fenton J W, 2nd, Malik A B. Thrombin-induced increase in albumin permeability across the endothelium. *J Cell Physiol.* 1986 July; 128(1): 96-104.
41. Liu F, Schaphorst K L, Verin A D, et al. Hepatocyte growth factor enhances endothelial cell barrier function and cortical cytoskeletal rearrangement: potential role of glycogen synthase kinase-3beta. *FASEB J.* 2002 July; 16(9): 950-62.
42. Zeng L, Xu H, Chew T L, et al. HMG CoA reductase inhibition modulates VEGF-induced endothelial cell hyperpermeability by preventing RhoA activation and myosin regulatory light chain phosphorylation. *FASEB J.* 2005 November; 19(13): 1845-7.

What is claimed is:

1. A compound represented by Chemical Formula 1 as a ginsenoside Rk1 or Rg3 analog:

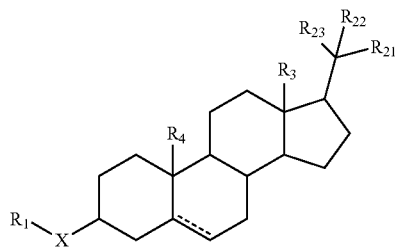

Chemical Formula 1 wherein X is oxygen;
$R_1$ is unsubstituted $C_{3-8}$ heterocycloalkyl containing oxygen as a heteroatom, or $C_{3-8}$ heterocycloalkenyl containing oxygen as a heteroatom, substituted with $C_{2-8}$ alkylcarboxy and $C_{3-8}$ alkylcarboxyalkyl;
$R_{21}$ is $C_{4-10}$ alkylcarboxyalkyl, or $C_{4-10}$ alkenylcarboxyalkyl;
$R_{22}$ is hydrogen;
$R_{23}$ is $C_{1-5}$ alkyl or forms a double bond with the carbon to which $R_{21}$ and $R_{22}$ are bonded together;
$R_{21}$ may form a double bond with the carbon to which $R_{22}$ and $R_{23}$ are bonded together;
$R_{22}$ is nonexistent when $R_{21}$ or $R_{23}$ forms a double bond with the carbon;
$R_3$ and $R_4$ are methyl; and
...... is a double bond.

2. The compound of claim 1, wherein the ginsenoside Rk1 or Rg3 analog is represented by Chemical Formula 2:

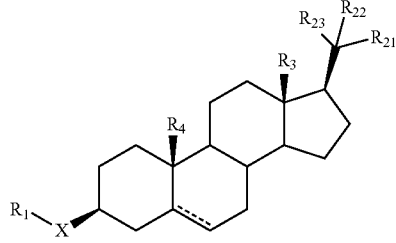

Chemical Formula 2 wherein X is oxygen;
$R_1$ is unsubstituted $C_{3-8}$ heterocycloalkyl containing oxygen as a heteroatom, or $C_{3-8}$ heterocycloalkenyl containing oxygen as a heteroatom, substituted with $C_{2-8}$ alkylcarboxy and $C_{3-8}$ alkylcarboxyalkyl;

$R_{21}$ is $C_{4-10}$ alkylcarboxyalkyl, or $C_{4-10}$ alkenylcarboxyalkyl;

$R_{22}$ is hydrogen;

$R_{23}$ is $C_{1-5}$ alkyl or forms a double bond with the carbon to which $R_{21}$ and $R_{22}$ are bonded together;

$R_{21}$ may form a double bond with the carbon to which $R_{22}$ and $R_{23}$ are bonded together;

$R_{22}$ is nonexistent when $R_{21}$ or $R_{23}$ forms a double bond with the carbon;

$R_3$ and $R_4$ are methyl; and

------- is a double bond.

3. A compound as a ginsenoside Rk1 or Rg3 analog represented by a chemical formula selected from the following Chemical Formulae:

Chemical Formula 40

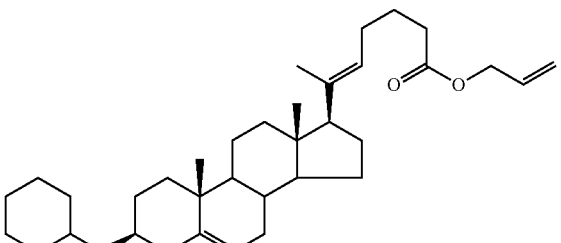

Chemical Formula 41

Chemical Formula 42

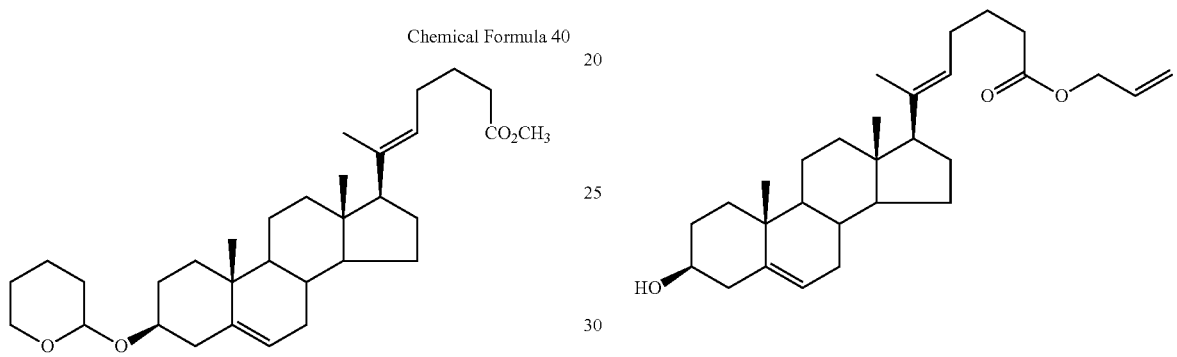

wherein Ac is acetyl

Chemical Formula 43

Chemical Formula 44

Chemical Formula 45

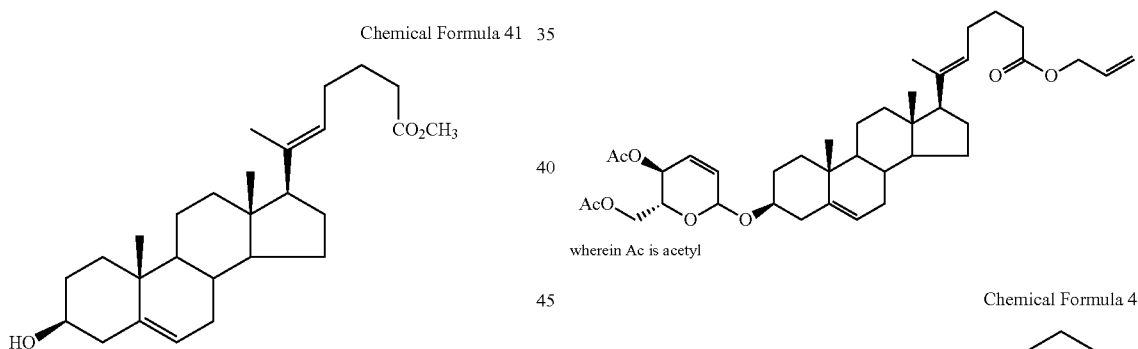

wherein Ac is acetyl

Chemical Formula 46

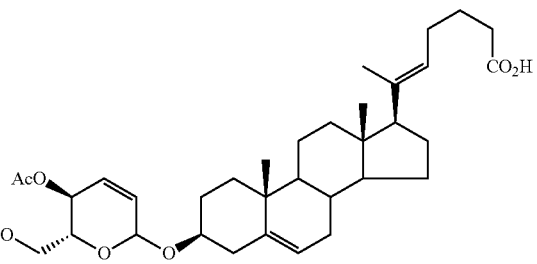

wherein Ac is acetyl.

4. A pharmaceutical composition comprising: (a) a pharmaceutically effective amount of the ginsenoside Rk1 or Rg3 analog of claim 1; and (b) a pharmaceutically acceptable salt.

5. A pharmaceutical composition comprising: (a) a pharmaceutically effective amount of a ginsenoside Rk1 or Rg3 analog selected from the group consisting of the following Chemical Formulae; and (b) a pharmaceutically acceptable salt:

Chemical Formula 4
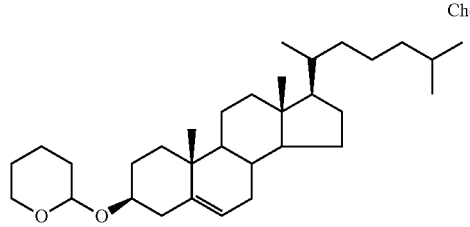
Chemical Formula 10
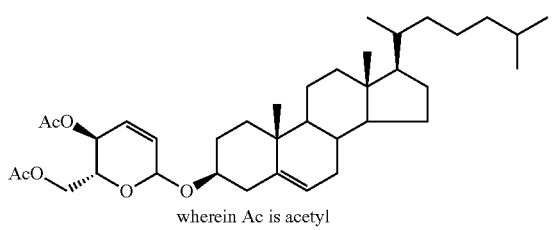
wherein Ac is acetyl
Chemical Formula 12
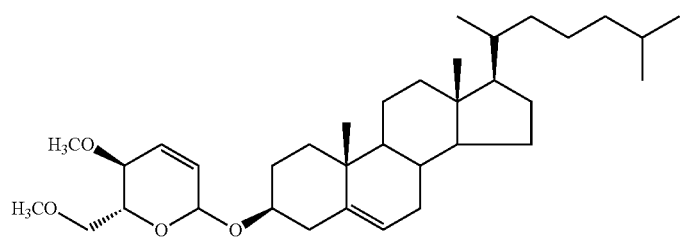
Chemical Formula 34
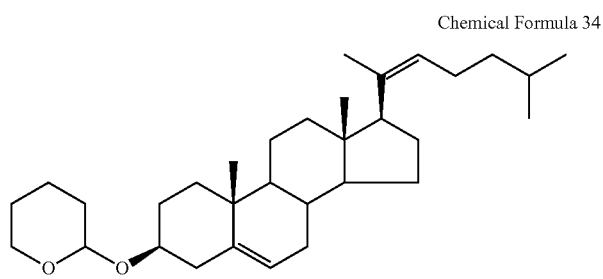
Chemical Formula 35
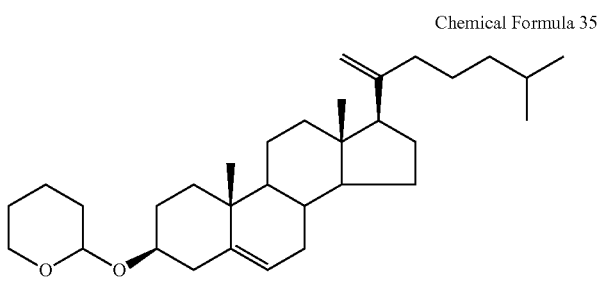
Chemical Formula 36
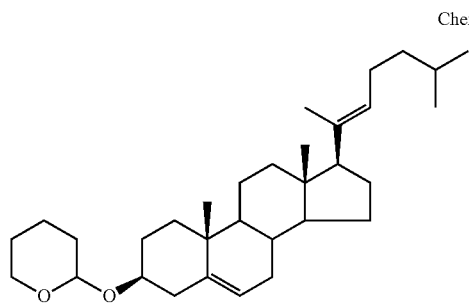
Chemical Formula 37
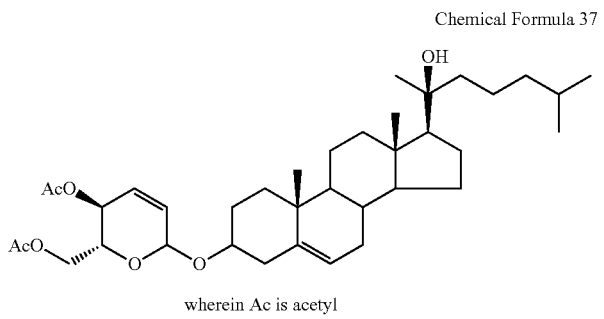
wherein Ac is acetyl
Chemical Formula 38
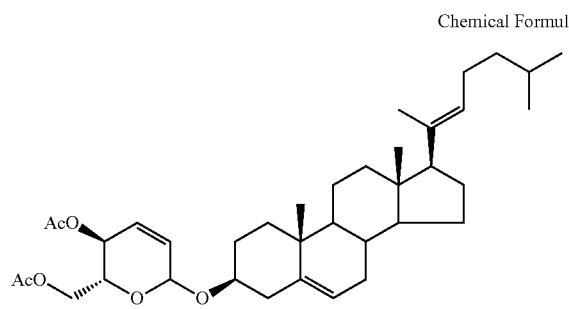
Chemical Formula 39
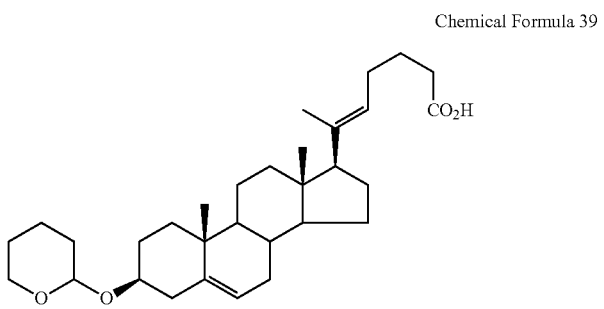

-continued
Chemical Formula 40
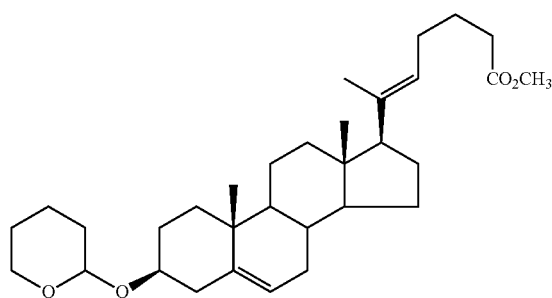
Chemical Formula 41
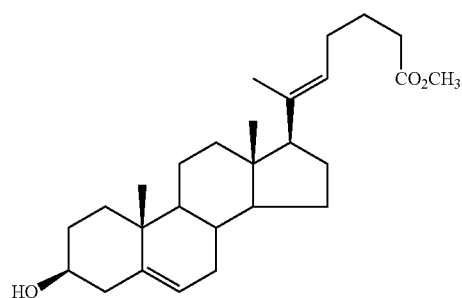
Chemical Formula 42
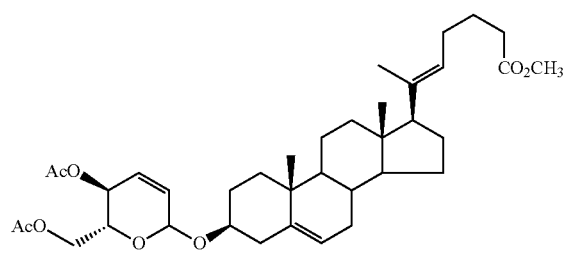
wherein Ac is acetyl
Chemical Formula 43
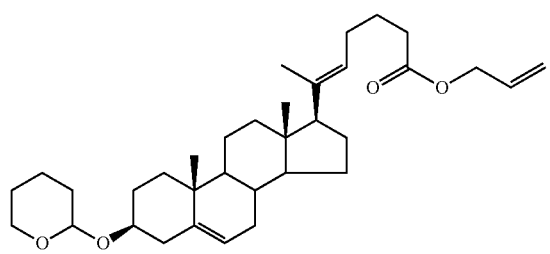
Chemical Formula 44
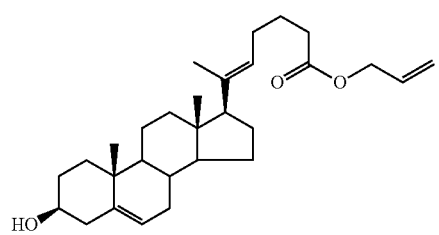
Chemical Formula 45
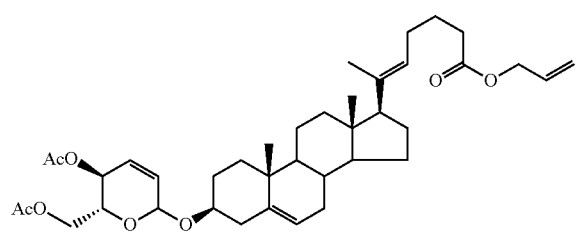
wherein Ac is acetyl
Chemical Formula 46
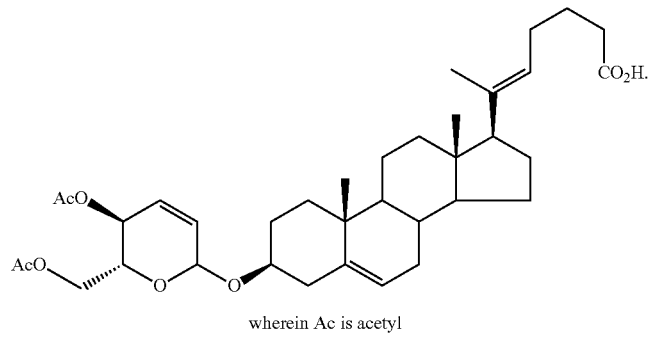
wherein Ac is acetyl
* * * * *